United States Patent
Hanuschik et al.

(10) Patent No.: US 12,279,921 B2
(45) Date of Patent: Apr. 22, 2025

(54) CLEANING DEVICE FOR TEETH

(71) Applicant: Fresh Health Inc., Mountain View, CA (US)

(72) Inventors: Michael Lee Hanuschik, Mountain View, CA (US); Bruce Michael Schena, Menlo Park, CA (US); Gerald Thomas Ryle, San Francisco, CA (US); Angela Junyan Chu, San Francisco, CA (US); Kristina Jenna Cook, San Francisco, CA (US); Kyle Geoffrey Mooney, San Francisco, CA (US); Ryan Christopher Evans, San Francisco, CA (US); Jonathan Riley Cox, Saratoga, CA (US); Stuart Gavin Ruedisueli, Roxbury, MA (US); Andrew Witt, Boston, MA (US); Sophie Katherine Sheeline, San Francisco, CA (US)

(73) Assignee: Fresh Health Inc., Mountain View, CA (US)

( * ) Notice: Subject to any disclaimer, the term of this patent is extended or adjusted under 35 U.S.C. 154(b) by 0 days.

(21) Appl. No.: 18/136,800

(22) Filed: Apr. 19, 2023

(65) Prior Publication Data

US 2023/0372072 A1    Nov. 23, 2023

Related U.S. Application Data

(63) Continuation-in-part of application No. 17/856,717, filed on Jul. 1, 2022, which is a continuation of
(Continued)

(51) Int. Cl.
*A61C 17/02* (2006.01)
*A61C 9/00* (2006.01)
(Continued)

(52) U.S. Cl.
CPC .......... *A61C 17/0211* (2013.01); *A61C 9/004* (2013.01); *A61C 15/00* (2013.01);
(Continued)

(58) Field of Classification Search
CPC ............ A61C 17/0211; A61C 17/0202; A61C 17/0217; A61C 17/00; A61C 17/024; A61C 17/032
See application file for complete search history.

(56) References Cited

U.S. PATENT DOCUMENTS

| 1,825,353 | A | 9/1931 | Johnson |
| 3,379,192 | A | 4/1968 | Warren, Jr. |

(Continued)

FOREIGN PATENT DOCUMENTS

| CN | 103554038 | 2/2014 |
| CN | 203693808 U | 7/2014 |

(Continued)

OTHER PUBLICATIONS

[Meet FRESH], YouTube.com, Posted Oct. 19, 2020 [online], [Site Visited Dec. 2, 2021], URL: https://www.youtube.com/watch?v=YdHCLy2R72l. (Year: 2020).
(Continued)

*Primary Examiner* — Nicholas D Lucchesi
(74) *Attorney, Agent, or Firm* — Van Pelt, Yi & James LLP

(57) ABSTRACT

An oral insert includes a plurality of manifolds and a plurality of fluid nozzles. A manifold switch is coupled to the plurality of manifolds. The manifold switch is configured to select which of the plurality manifolds is to receive fluid from a fluid source.

17 Claims, 26 Drawing Sheets

Related U.S. Application Data application No. 17/066,373, filed on Oct. 8, 2020, now Pat. No. 11,376,105, which is a continuation of application No. 16/024,373, filed on Jun. 29, 2018, now Pat. No. 11,234,801, application No. 18/136,800, filed on Apr. 19, 2023 is a continuation-in-part of application No. 17/495,732, filed on Oct. 6, 2021, which is a continuation of application No. 17/066,383, filed on Oct. 8, 2020, now Pat. No. 11,141,249, which is a continuation of application No. PCT/US2020/028311, filed on Apr. 15, 2020, application No. 18/136,800, filed on Apr. 19, 2023 is a continuation-in-part of application No. 17/698,316, filed on Mar. 18, 2022, which is a continuation of application No. 17/066,390, filed on Oct. 8, 2020, now Pat. No. 11,281,816.

(60) Provisional application No. 62/527,955, filed on Jun. 30, 2017, provisional application No. 62/833,926, filed on Apr. 15, 2019, provisional application No. 62/879,983, filed on Jul. 29, 2019, provisional application No. 63/054,678, filed on Jul. 21, 2020.

(51) Int. Cl.
*A61C 15/00* (2006.01)
*A61C 15/04* (2006.01)
*A61C 17/00* (2006.01)
*A61C 17/16* (2006.01)
*G06T 17/00* (2006.01)
*A61B 6/51* (2024.01)
*A61C 17/028* (2006.01)

(52) U.S. Cl.
CPC ............ *A61C 15/047* (2013.01); *A61C 17/00* (2013.01); *A61C 17/02* (2013.01); *A61C 17/0217* (2013.01); *A61C 17/16* (2013.01); *G06T 17/00* (2013.01); *A61B 6/51* (2024.01); *A61C 9/00* (2013.01); *A61C 9/0053* (2013.01); *A61C 17/0202* (2013.01); *A61C 17/028* (2013.01)

(56) References Cited

U.S. PATENT DOCUMENTS

| | | | |
|---|---|---|---|
| 3,527,218 | A | 9/1970 | Westine |
| 3,731,675 | A | 5/1973 | Kelly |
| 3,840,992 | A | 10/1974 | English |
| 4,164,940 | A | 8/1979 | Quinby |
| 5,082,444 | A | 1/1992 | Rhoades |
| 5,104,315 | A | 4/1992 | McKinley |
| 5,177,827 | A | 1/1993 | Ellison |
| 5,246,367 | A | 9/1993 | Ito |
| 5,273,032 | A | 12/1993 | Borody |
| D346,212 | S | 4/1994 | Hosl |
| D352,104 | S | 11/1994 | Clawson |
| 5,365,624 | A | 11/1994 | Berns |
| D371,242 | S | 7/1996 | Shimatsu |
| D406,405 | S | 3/1999 | Yoshida |
| 6,056,710 | A | 5/2000 | Bachman |
| D438,953 | S | 3/2001 | Frank |
| 6,334,853 | B1 | 1/2002 | Kopelman |
| 6,353,956 | B1 | 3/2002 | Berge |
| 6,402,707 | B1 | 6/2002 | Ernst |
| 6,439,889 | B1 | 8/2002 | Chen |
| 6,475,173 | B1 | 11/2002 | Bachman |
| D467,659 | S | 12/2002 | Horth |
| D505,493 | S | 5/2005 | Ryan |
| 6,893,259 | B1 | 5/2005 | Reizenson |
| 6,896,519 | B2 | 5/2005 | Chen |
| D519,209 | S | 4/2006 | Bublewitz |
| 7,059,853 | B2 | 6/2006 | Hegemann |
| 7,092,107 | B2 | 8/2006 | Babayoff |
| 7,112,065 | B2 | 9/2006 | Kopelman |
| 7,156,661 | B2 | 1/2007 | Choi |
| D574,929 | S | 8/2008 | Causby |
| D625,406 | S | 10/2010 | Seki |
| D636,119 | S | 4/2011 | Worlock |
| 8,102,538 | B2 | 1/2012 | Babayoff |
| 8,241,035 | B2 | 8/2012 | Jones |
| 8,363,228 | B2 | 1/2013 | Babayoff |
| D682,431 | S | 5/2013 | Westerlund |
| 8,534,281 | B2 | 9/2013 | Davies |
| 8,567,408 | B2 | 10/2013 | Roettger |
| 8,617,090 | B2 | 12/2013 | Fougere |
| 8,638,447 | B2 | 1/2014 | Babayoff |
| 8,638,448 | B2 | 1/2014 | Babayoff |
| 8,675,207 | B2 | 3/2014 | Babayoff |
| 8,684,956 | B2 | 4/2014 | McDonough |
| 8,888,727 | B2 | 11/2014 | Boyd |
| 8,936,466 | B2 | 1/2015 | Moffson |
| 9,022,959 | B2 | 5/2015 | Fusi, II |
| 9,022,960 | B2 | 5/2015 | Fougere |
| 9,022,961 | B2 | 5/2015 | Fougere |
| D732,175 | S | 6/2015 | Snyder |
| D735,935 | S | 8/2015 | Burrell |
| 9,101,433 | B2 | 8/2015 | Babayoff |
| 9,216,073 | B2 | 12/2015 | McDonough |
| 9,222,768 | B2 | 12/2015 | Ernst |
| 9,299,192 | B2 | 3/2016 | Kopelman |
| 9,308,064 | B2 | 4/2016 | Binner |
| D757,245 | S | 5/2016 | Lee |
| 9,367,063 | B2 | 6/2016 | Herrman |
| D765,861 | S | 9/2016 | Iijima |
| D767,118 | S | 9/2016 | Hyde |
| 9,579,173 | B2 | 2/2017 | Fougere |
| 9,615,901 | B2 | 4/2017 | Babayoff |
| D787,068 | S | 5/2017 | Sosa |
| D797,278 | S | 9/2017 | Uchida |
| 9,770,643 | B2 | 9/2017 | Hawkins |
| D800,587 | S | 10/2017 | Cho |
| D800,910 | S | 10/2017 | Layzell |
| D801,521 | S | 10/2017 | Hyde |
| 10,195,006 | B2 | 2/2019 | Freiberg |
| 10,215,317 | B2 | 2/2019 | Burkhart |
| D861,176 | S | 9/2019 | Yoon |
| D864,578 | S | 10/2019 | Liu |
| 10,591,898 | B2 | 3/2020 | Wolf |
| 10,595,627 | B1 | 3/2020 | Laurent |
| 10,617,499 | B1 | 4/2020 | Bodin |
| D886,278 | S | 6/2020 | Lin |
| D887,146 | S | 6/2020 | Lander |
| 10,682,211 | B1 | 6/2020 | Barlet |
| 10,716,651 | B2 | 7/2020 | Hyun |
| D893,046 | S | 8/2020 | Jones |
| D899,596 | S | 10/2020 | Papenbrock |
| D901,670 | S | 11/2020 | Tuononen |
| D908,884 | S | 1/2021 | Yamakawa |
| D910,084 | S | 2/2021 | Huang |
| 10,932,555 | B2 | 3/2021 | De Gentile |
| 10,966,804 | B2 | 4/2021 | Ouin |
| 11,141,249 | B2 | 10/2021 | Evans |
| 11,234,801 | B2 | 2/2022 | Hanuschik |
| 11,281,816 | B2 | 3/2022 | Ruedisueli |
| D956,980 | S | 7/2022 | Chu |
| 11,376,105 | B2 | 7/2022 | Hanuschik |
| D962,422 | S | 8/2022 | Evans |
| 11,622,751 | B2 | 4/2023 | Fougere |
| 2007/0184404 | A1 | 8/2007 | Johnki |
| 2009/0145448 | A1 | 6/2009 | Worlock |
| 2009/0208898 | A1 | 8/2009 | Kaplan |
| 2009/0223513 | A1 | 9/2009 | Papania |
| 2009/0229062 | A1 | 9/2009 | Filby |
| 2010/0062397 | A1 | 3/2010 | Brewer |
| 2011/0027746 | A1 | 2/2011 | McDonough |
| 2011/0072605 | A1 | 3/2011 | Steur |
| 2011/0087197 | A1 | 4/2011 | Mombrinie |
| 2011/0117517 | A1 | 5/2011 | Bergheim |
| 2011/0154595 | A1 | 6/2011 | Hill |
| 2011/0185525 | A1 | 8/2011 | Stapelbroek |
| 2011/0318705 | A1 | 12/2011 | Sullivan |

(56) References Cited

U.S. PATENT DOCUMENTS

| | | |
|---|---|---|
| 2012/0021375 A1 | 1/2012 | Binner |
| 2012/0077144 A1 | 3/2012 | Fougere |
| 2012/0189976 A1 | 7/2012 | McDonough |
| 2012/0199141 A1 | 8/2012 | Hackman |
| 2012/0219926 A1* | 8/2012 | Sullivan ............. A61C 17/0211 433/80 |
| 2012/0318289 A1 | 12/2012 | Sahoo |
| 2013/0014331 A1 | 1/2013 | Garner |
| 2013/0081217 A1 | 4/2013 | Jeong |
| 2013/0165828 A1 | 6/2013 | Sullivan |
| 2013/0190608 A1 | 7/2013 | Schmidt |
| 2013/0239978 A1 | 9/2013 | Stubbs |
| 2013/0260332 A1 | 10/2013 | Shapiro |
| 2014/0261464 A1 | 9/2014 | Layzell |
| 2015/0282911 A1 | 10/2015 | Steiner |
| 2016/0235509 A1 | 8/2016 | Freiberg |
| 2016/0236851 A1 | 8/2016 | Leser |
| 2017/0056143 A1 | 3/2017 | Hyun |
| 2017/0056144 A1 | 3/2017 | Levy |
| 2017/0086954 A1* | 3/2017 | De Jager ............. A61M 3/0279 |
| 2017/0165040 A1 | 6/2017 | Wolgin |
| 2017/0373517 A1 | 12/2017 | Johanski |
| 2018/0000573 A1 | 1/2018 | Miller |
| 2018/0098619 A1 | 4/2018 | Pierce |
| 2018/0116773 A1 | 5/2018 | Chen |
| 2018/0140400 A1 | 5/2018 | Hoshino |
| 2018/0344440 A1 | 12/2018 | Dorward |
| 2018/0368957 A1 | 12/2018 | Hyun |
| 2019/0000599 A1 | 1/2019 | Hanuschik |
| 2020/0196994 A1 | 6/2020 | Fougere |
| 2021/0030519 A1 | 2/2021 | Hanuschik |
| 2021/0085436 A1 | 3/2021 | Evans |
| 2022/0265406 A1 | 8/2022 | Evans |

FOREIGN PATENT DOCUMENTS

| | | |
|---|---|---|
| CN | 105919685 | 9/2016 |
| CN | 304416685 | 5/2017 |
| CN | 108742909 | 11/2018 |
| EM | 87233990002 | 10/2021 |
| EP | 00865770 | 9/1998 |
| FR | 2905258 | 3/2008 |
| JP | 2002045378 | 2/2002 |
| JP | 2008515575 | 5/2008 |
| JP | 2013500781 | 1/2013 |
| JP | 2013534846 | 9/2013 |
| WO | 2011014619 | 2/2011 |
| WO | 2016164068 | 10/2016 |
| WO | 2020214697 | 10/2020 |
| WO | 2020223353 | 11/2020 |

OTHER PUBLICATIONS

[Vumblr All-In-One Vacuum Oral Care Device cleans and whitens your teeth], available on thegadgetflow.com, by [Genevieve Healey], Published [May 16, 2019] [online], [site visited Dec. 2, 2021], Internet URL: https://thegadgetflow.com/portfolio/vacuum-oral-care-device/. (Year: 2019).

[Willow Launches Its Tooth Brushing Robot for Kids], available on techcrunch.com, by Romain Dillet posted Apr. 13, 2021 [online], [site visited Dec. 2, 2021], Internet URL: https://techcrunch.com/2021/04/13/willo-launches-its-tooth-brushing-robot-for-kids/. (Year: 2021).

Extended European Search Report issued in European Application No. 18824871.0 on Feb. 8, 2021, 10 pages.

International Preliminary Report on Patentability for International Application No. PCT/US2020/028311, dated Oct. 28, 2021, 9 pages.

International Search Report and Written Opinion for International Application No. PCT/US2021/042256 dated Nov. 15, 2021, 20 pages.

International Search Report and Written Opinion issued in International Application No. PCT/US2018/040459 on Nov. 5, 2018, 12 pages.

International Search Report and Written Opinion issued in International Application No. PCT/US2020/028311 on Aug. 14, 2020, 16 pages.

* cited by examiner

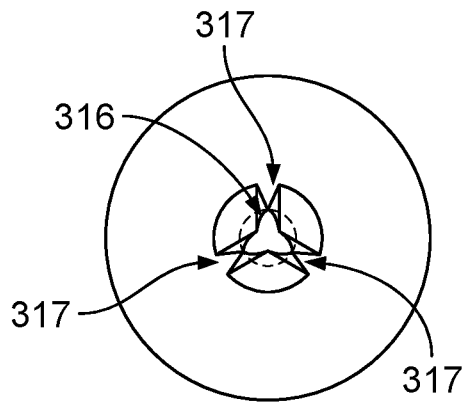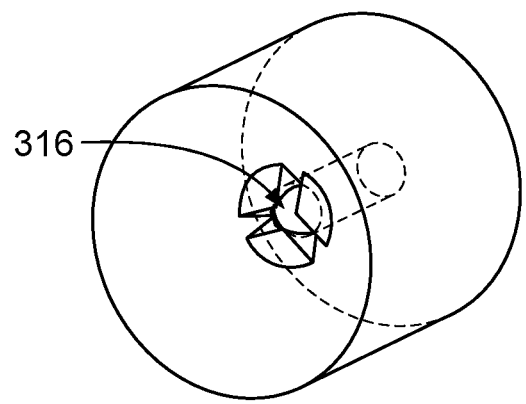
FIG. 3F　　　　　　　　　　　FIG. 3G
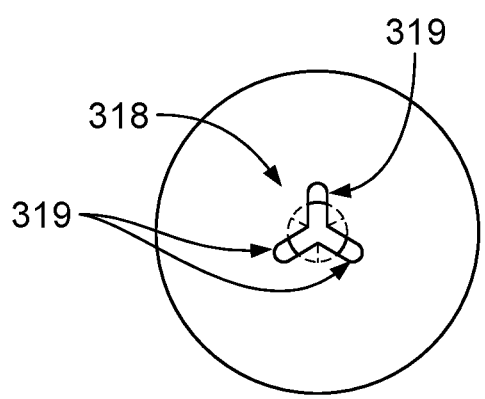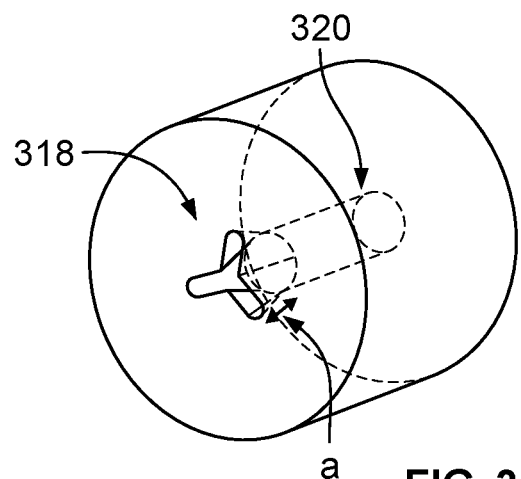
FIG. 3H　　　　　　　　　　　FIG. 3I
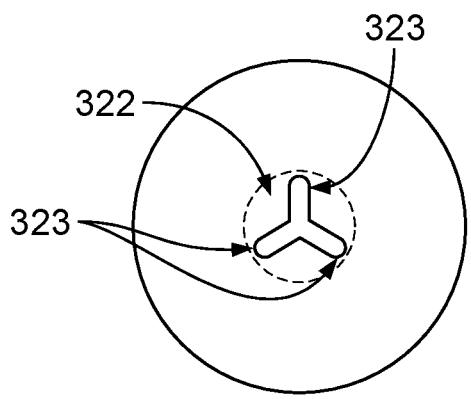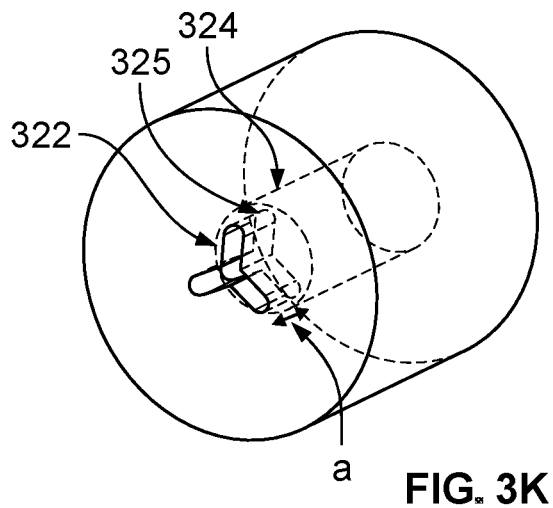
FIG. 3J　　　　　　　　　　　FIG. 3K

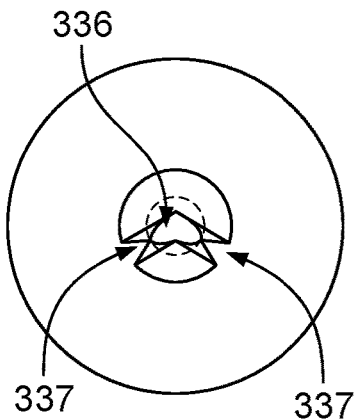
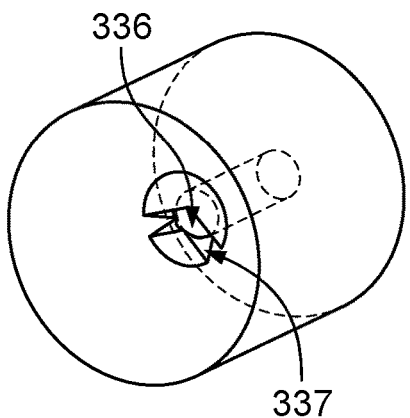
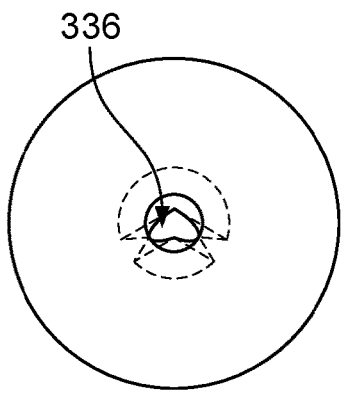
FIG. 3O  FIG. 3P  FIG. 3Q
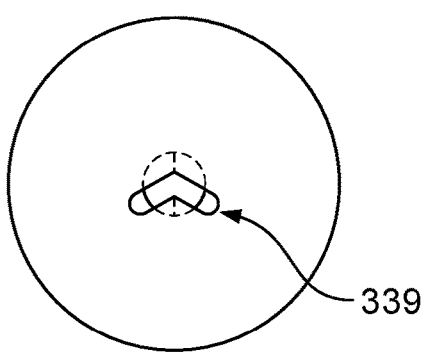
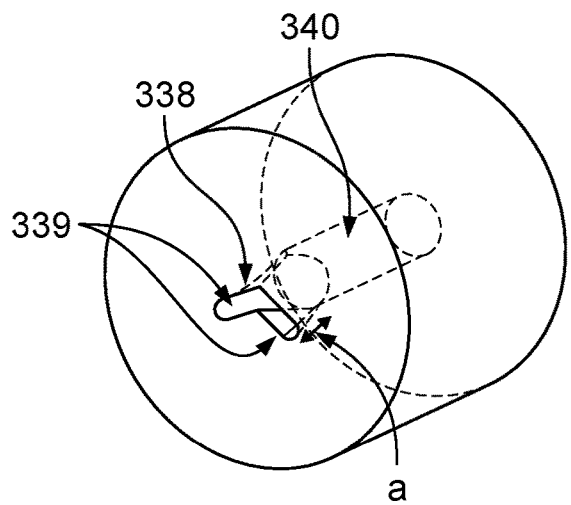
FIG. 3R  FIG. 3S
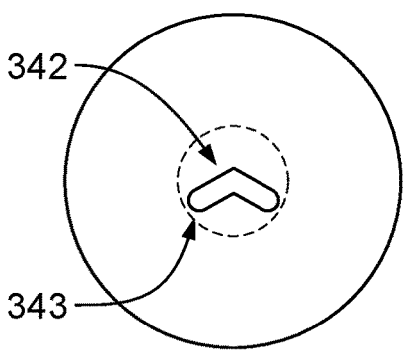
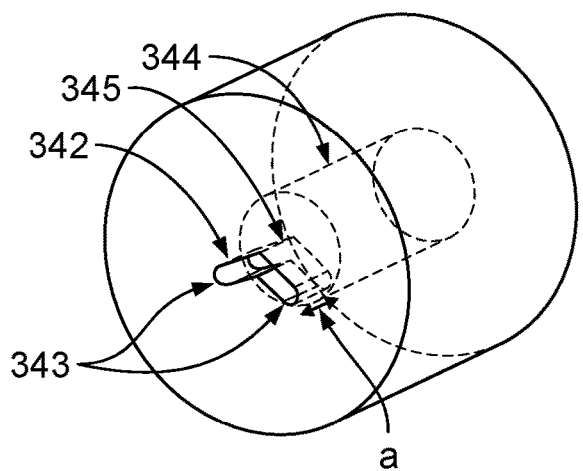
FIG. 3T  FIG. 3U

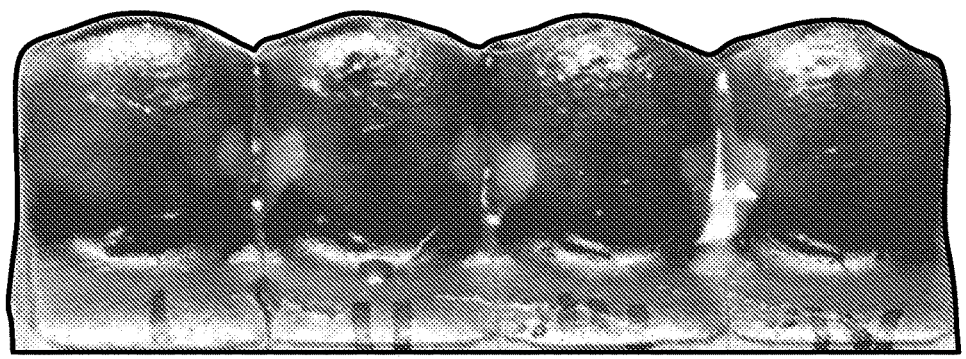
FIG. 4A
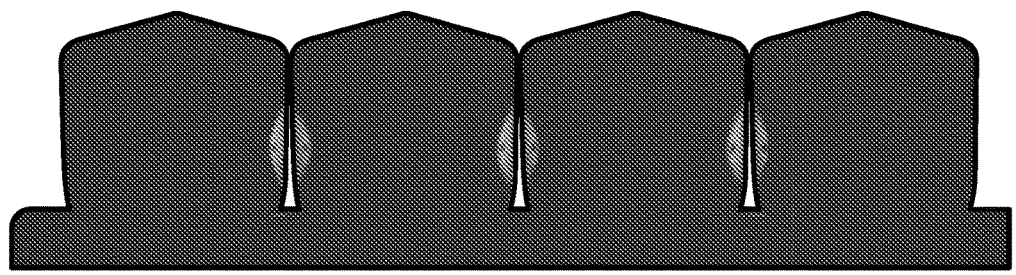
Shear Stress Magnitude (Pa)
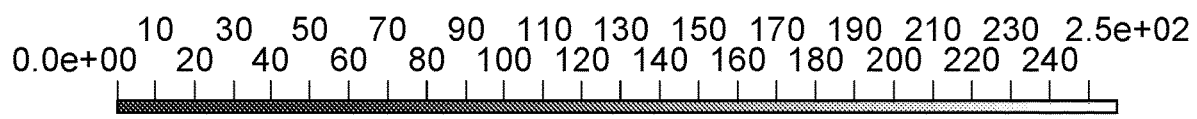
FIG. 4B
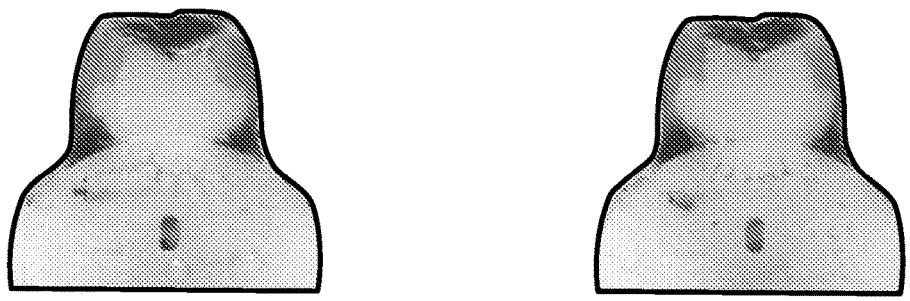
FIG. 4C

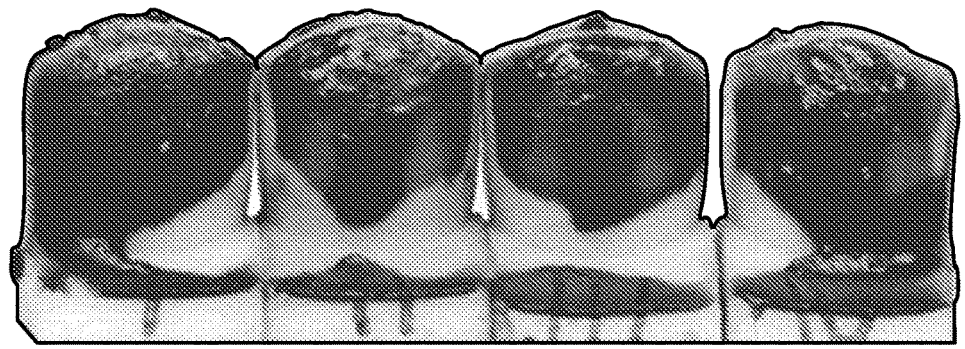
FIG. 6A
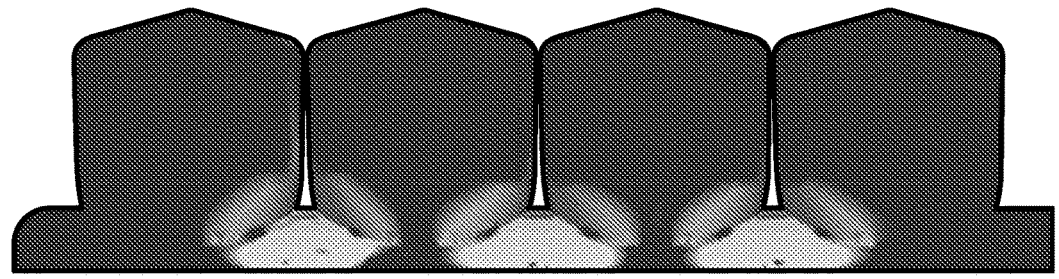
Shear Stress Magnitude (Pa)
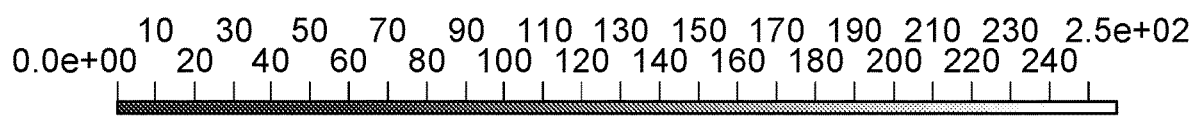
FIG. 6B
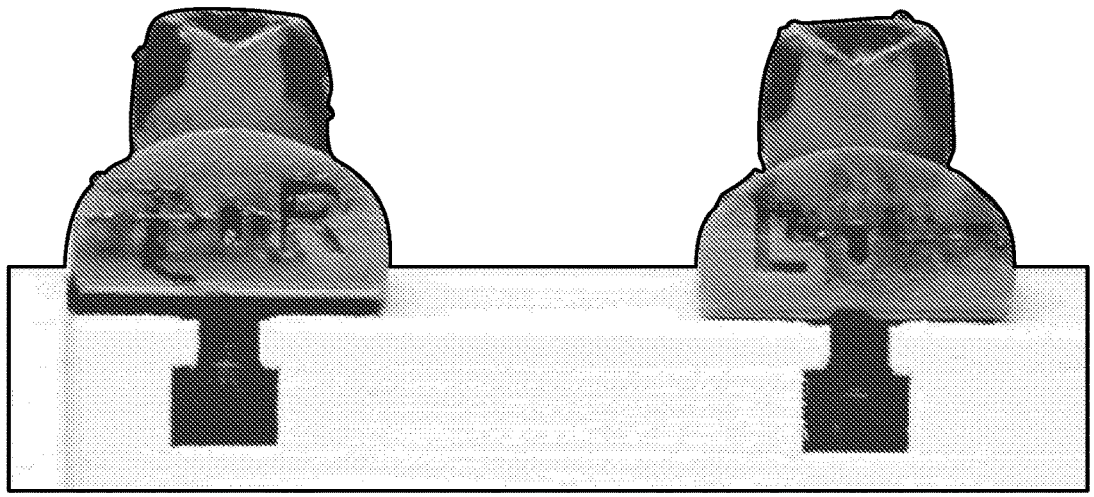
FIG. 6C

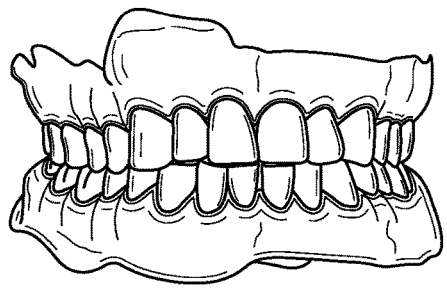

500

502
Obtaining oral structure data comprising the size, shape, and location of a user's teeth and gingiva

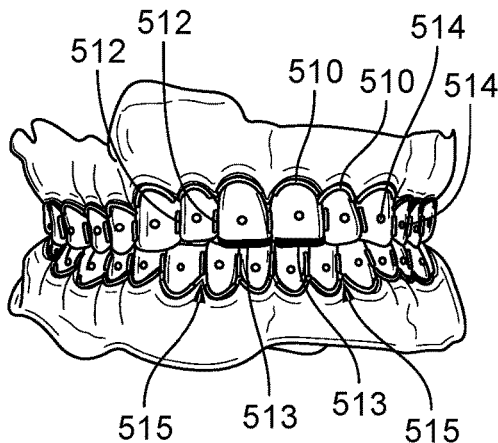

504
Calculating an oral surface map that identifies locations of gingival margins, interproximal features, and contours of the occlusal, facial and lingual surfaces of the teeth

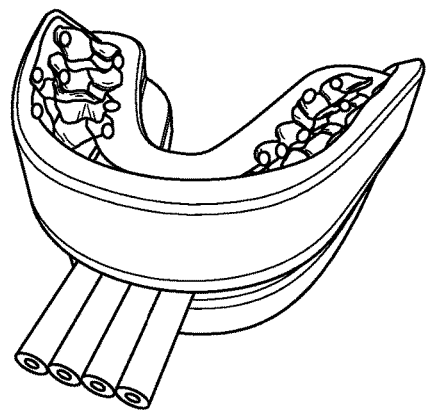

506
Generating an arrangement of fluid openings in an oral insert, wherein the arrangement of fluid openings corresponds to the location of the gingival margin, interproximal features, and contours of the occlusal, facial and lingual surfaces of the teeth

CLEANING DEVICE FOR TEETH

CROSS REFERENCE TO OTHER APPLICATIONS

This application is a continuation in part of U.S. patent application Ser. No. 17/856,717, entitled SYSTEMS AND METHODS FOR PERSONALIZED ORAL IRRIGATION filed Jul. 1, 2022, which is a continuation of U.S. patent application Ser. No. 17/066,373, now U.S. Pat. No. 11,376,105, entitled SYSTEMS AND METHODS FOR PERSONALIZED ORAL IRRIGATION filed Oct. 8, 2020, which is a continuation of U.S. patent application Ser. No. 16/024,373, now U.S. Pat. No. 11,234,801, entitled SYSTEMS AND METHODS FOR PERSONALIZED ORAL IRRIGATION filed Jun. 29, 2018, which claims priority to U.S. Provisional Patent Application No. 62/527,955, entitled SYSTEMS AND METHODS FOR PERSONALIZED ORAL IRRIGATION filed Jun. 30, 2017, each of which is incorporated herein by reference for all purposes.

This application is a continuation in part of U.S. patent application Ser. No. 17/495,732, entitled SYSTEMS AND METHODS FOR PERSONALIZED ORAL CARE filed Oct. 6, 2021, which is a continuation of U.S. patent application Ser. No. 17/066,383, now U.S. Pat. No. 11,141,249, entitled SYSTEMS AND METHODS FOR PERSONALIZED ORAL CARE filed Oct. 8, 2020, which is a continuation of International Patent Application PCT/US20/28311, entitled SYSTEMS AND METHODS FOR PERSONALIZED ORAL CARE filed Apr. 15, 2020, which claims priority to U.S. Provisional Patent Application No. 62/833,926, entitled HYBRID SYSTEMS AND METHODS FOR PERSONALIZED ORAL CARE filed Apr. 15, 2019, and claims priority to U.S. Provisional Patent Application No. 62/879,983, entitled HYBRID SYSTEMS AND METHODS FOR PERSONALIZED ORAL CARE filed Jul. 29, 2019, each of which is incorporated herein by reference for all purposes.

This application is a continuation in part of U.S. patent application Ser. No. 17/698,316, entitled SYSTEMS AND METHODS FOR MANUFACTURING PERSONALIZED ORAL CARE DEVICES filed Mar. 18, 2022, which is a continuation of U.S. patent application Ser. No. 17/066,390, now U.S. Pat. No. 11,281,816, entitled SYSTEMS AND METHODS FOR MANUFACTURING PERSONALIZED ORAL CARE DEVICES filed Oct. 8, 2020, which claims priority to U.S. Provisional Patent Application No. 63/054,678, entitled SYSTEMS AND METHODS FOR MANUFACTURING PERSONALIZED ORAL CARE DEVICES filed Jul. 21, 2020, each of which is incorporated herein by reference for all purposes.

BACKGROUND OF THE INVENTION

Gum disease is a widespread condition that affects public health and quality of life. The tools we use to take care of our teeth are outdated. Toothbrushes have existed since 619 AD and floss has existed since 1819 AD. Brushing and flossing are woefully inadequate for comprehensive oral and dental care. Furthermore, few adults include flossing as part of their regular dental hygiene, which may contribute to high rates of periodontal disease and tooth loss. Poor dental and oral health may contribute to a shortened life span and other ailments.

Clinical studies indicate that water flossers (such as WATERPIK®) may be effective at cleaning in between the teeth and around the gums. However, water flossing can be too messy for some, and it can be time-consuming and challenging to position a water flosser at an optimized cleaning location for each tooth. Given the myriad oral geometries that blossom from the diverse nature of human physiology, achieving sufficient cleaning efficacy with a water flosser may also be difficult.

SUMMARY OF THE INVENTION

Described herein are systems and methods for providing personalized oral irrigation. A system for personalized oral irrigation may comprise a fluid reservoir and a customized oral insert in fluid communication with the fluid reservoir. The oral insert may comprise an arrangement of fluid openings positioned to provide a customized fluid flow over a user's teeth. In some variations, the oral insert may be customized to accommodate a user's oral geometry. Fluid egress from the plurality of fluid openings may clean multiple teeth simultaneously and the location and geometry of the fluid openings with respect to specific and unique structures of the user's mouth may help facilitate expeditious and/or effective cleaning of teeth surfaces. In some variations, the oral insert may comprise a custom arrangement of a plurality of fluid openings or nozzles where each of the nozzles is positioned to target a specific dental feature or structure.

One variation of a customized system for oral irrigation may comprise a fluid reservoir and a customized oral insert in fluid communication with the fluid reservoir. The customized oral insert may comprise one or more oral alignment structures and an arrangement of fluid openings positioned to provide a customized fluid flow path across or in between one or more teeth of a user. The arrangement of fluid openings may be determined based on at least one characteristic of one or more teeth. The one or more oral alignment structures may comprise a plurality of contours that correspond to the one or more teeth. The at least one characteristic may comprise the geometry of at least one tooth. The at least one characteristic may, alternatively or additionally, comprise the size and shape of one or more interproximal regions that may be located between the teeth, and the arrangement of fluid openings may comprise a plurality of openings oriented parallel to corresponding interproximal regions and located within about 0 mm to about 10 mm from the corresponding interproximal region. The at least one characteristic may alternatively or additionally comprise the contours of the planar surfaces of the teeth, and the arrangement of fluid openings may comprise a plurality of openings oriented perpendicular to corresponding planar surfaces and located within about 0 mm to about 10 mm from the corresponding planar surface. The at least one characteristic may alternatively or additionally comprise the size and shape of teeth gingival margins. The arrangement of fluid openings may comprise a plurality of openings oriented at an angle from about 0° to about 90° relative to the tooth's surface at the gingival margin, for example, from about 45° to about 135°, from about 0° to about 45°, from about 35° to about 55°, about 45°, etc. The fluid openings may be located within about 0 mm to about 10 mm from the corresponding gingival margin. Alternatively or additionally, the at least one characteristic may comprise the geometry of other oral and/or dental devices, for example, permanent and removable dental restorations/prosthetics, orthodontic appliances, and the like (e.g., crowns, bridges, implants, braces, retainers, dentures, and the like). One variation of a system may comprise a handle and the oral insert may be coupled to the handle. The handle may comprise a fluid flow management module that regulates fluid ingress to the oral insert. The oral insert may comprise one or more manifolds in fluid communication with the fluid flow management module. The number and geometry of the one or more manifolds may be determined in part based on the arrangement of fluid openings and at least one characteristic of the one or more teeth.

Also disclosed herein are methods of generating an arrangement of fluid openings in an oral insert. One variation of a method may comprise obtaining oral structure data comprising the size, shape, and location of a user's teeth and gums, calculating an oral surface map that identifies locations of gingival margins, interproximal regions, incisal edges, and contours of the occlusal, facial, lingual, mesial and distal surfaces of the teeth, and generating an arrangement of fluid openings in an oral insert, where the arrangement of fluid openings corresponds to the location of the gingival margins, interproximal regions, incisal edges, and contours of the occlusal, facial, lingual, mesial and distal surfaces of the teeth. Obtaining oral structure data may comprise acquiring a 3-D dental scan and/or acquiring X-ray dental image(s), including cone beam computed tomography, acquiring photograph(s) of the teeth, or the like, and processing the images using photogrammetry. Optionally, calculating the oral surface map may comprise identifying the location and geometry of oral and/or dental devices or implants (e.g., orthodontics). Generating an arrangement of fluid openings may comprise identifying a size and shape of one or more interproximal regions that may be located between the teeth and positioning a plurality of openings oriented parallel to corresponding interproximal regions and located within a predetermined distance (e.g., about 0 mm to about 10 mm) from the corresponding interproximal region. Alternatively or additionally, generating an arrangement of fluid openings may comprise identifying occlusal, facial, lingual, mesial and distal surfaces of the teeth and positioning a plurality of openings oriented perpendicular to corresponding teeth surfaces and located within a predetermined distance (e.g., about 0 mm to about 10 mm) from the corresponding teeth surface. Alternatively or additionally, generating an arrangement of fluid openings may comprise identifying the size and shape of teeth gingival margins and positioning a plurality of openings oriented at an angle from about 0° to about 90° relative to the tooth's surface at the gingival margin, for example, from about 45° to about 135°, from about 0° to about 45°, from about 35° to about 55°, about 45°, etc. The fluid openings may be located a predetermined distance (e.g., about 0 mm to about 10 mm) from the corresponding tooth surface or gingival margin.

One variation of a customized system for oral irrigation may comprise a fluid reservoir and a customized oral insert in fluid communication with the fluid reservoir, where the customized oral insert comprises an arrangement of fluid openings positioned to provide a customized fluid flow to one or more teeth of a user. The arrangement of fluid openings is determined based on at least one characteristic of the one or more teeth and/or gingiva. A fluid opening or nozzle may have a multi-lobe shape comprising a first lobe and a second lobe. The first lobe and the second lobe may define a lobe angle therebetween. The lobe angle may correspond with a curvature of a gingival margin of the one or more teeth. In some variations, the first lobe has a first length and the second lobe has a second length, and the first and second lengths may be the same or may be different. The first lobe may have a first width and the second lobe may have a second width, and the first and second widths may be the same or different. Alternatively or additionally, at least one of the first lobe and the second lobe may have a tapered portion such that a width of the lobe decreases along a length of the lobe.

In some variations, the multi-lobe shape may further comprise a third lobe. The first, second, and third lobes may be radially-arranged around a center of the fluid opening. In some variations, the first, second, and third lobes may be radially-symmetric around a center of the fluid opening. The first lobe and the second lobe may define a lobe angle therebetween that corresponds with a curvature of a gingival margin of the one or more teeth, and the third lobe may be approximately aligned along an interproximal space between the teeth.

Optionally, a customized system for oral irrigation may further comprise an oral alignment structure that comprises a plurality of contours that correspond to the one or more teeth.

In some variations, the at least one characteristic may comprise the geometry of each tooth and/or gingival margin. The at least one characteristic may comprise the size and shape of one or more interproximal regions between the teeth, and the arrangement of fluid openings may comprise a plurality of openings oriented at an angle from about 0° to about 90° relative to a long axis of a tooth and may be located within about 0 mm to about 10 mm from interproximal regions on either side of the tooth. Alternatively or additionally, the at least one characteristic may comprise the contours of the surfaces of the teeth, and the arrangement of fluid openings comprises a plurality of openings oriented at an angle from about 0° to about 90° relative to a long axis of a tooth and located within about 0 mm to about 10 mm from a surface of the tooth. In some variations, the at least one characteristic may comprise the size and shape of gingival margins of the teeth, and the arrangement of fluid openings may comprise a plurality of openings oriented at an angle from about 0° to about 90° relative to a long axis of a tooth and may be located within about 0 mm to about 10 mm from a gingival margin of the tooth. Alternatively or additionally, the at least one characteristic may comprise the geometry of oral and/or dental devices or implants. In some variations, the arrangement of fluid openings may comprise a first set of fluid openings on a first region of the oral insert and arranged to provide customized fluid flow to a first set of teeth, and a second set of fluid openings on a second region of the insert opposite the first region of the oral insert and arranged to provide customized fluid flow to a second set of teeth of the user. The first region of the oral insert may be an upper region of the oral insert and the first set of teeth comprises maxillary teeth, and the second region of the oral insert may be a lower region of the oral insert, and the second set of teeth may comprise mandibular teeth.

A customized system for oral irrigation may also comprise a handle where the oral insert is coupled to the handle. The handle may comprise a fluid flow management module that regulates fluid ingress to the oral insert. The oral insert may further comprise one or more manifolds in fluid communication with the fluid flow management module. A number and geometry of the one or more manifolds may be determined based on the arrangement of the fluid openings. The fluid flow management module may comprise a pump in fluid communication with the fluid reservoir. The fluid flow management module may comprise a manifold switcher configured to vary fluid flow from the reservoir to the one or more manifolds of the oral insert. Optionally, the fluid flow management module may comprise an additive-receiving port that is in fluid communication with at least one manifold of the oral insert, the additive-receiving port having an additive cartridge attachment mechanism. The fluid reservoir may be a first fluid reservoir and the system may further comprise a second fluid reservoir, and the fluid flow management module may be configured to vary fluid flow between the first and second fluid reservoirs and the one or more manifolds of the oral insert.

In some variations, the oral insert may be a first oral insert and the system may further comprise a second oral insert comprising a second arrangement of fluid openings, where the first oral insert may be configured to provide customized fluid flow to one or more mandibular teeth of the user and the second oral insert may be configured to provide customized fluid flow to one or more maxillary teeth of the user. The system may further comprise a handle and the first oral insert and the second oral insert may be configured to be coupled to the handle. For example, the first oral insert and the second oral insert may be configured to be simultaneously coupled to the handle. In some variations, the oral insert is a first oral insert and the system further comprises a second oral insert comprising a second arrangement of fluid openings, where the first oral insert is configured to provide customized fluid flow to one or more teeth on a left side of the user and the second oral insert is configured to provide customized fluid flow to one or more teeth on a right side of the user. The oral insert may be a first oral insert and the arrangement of fluid openings is a first arrangement of fluid openings, and the system may further comprise a second oral insert comprising an arrangement of fluid openings. The first arrangement of fluid openings may be located along facial surfaces and/or lingual surfaces and/or occlusal surfaces of the user's teeth, and the second arrangement of fluid openings may be located at interproximal spaces between the user's teeth. The arrangement of fluid openings may correspond to a location of gingival margins, interproximal regions, incisal edges, and/or contours of occlusal, facial, lingual, mesial, and/or distal surfaces of teeth associated with the user.

Also described herein are methods of generating an arrangement of fluid openings in an oral insert. One variation of a method may comprise obtaining oral structure data comprising the size, shape, and location of a user's teeth and gums, calculating an oral surface map that identifies locations of gingival margins, interproximal regions, and contours of the incisal edges, occlusal, facial, lingual, mesial and distal surfaces of the teeth, and generating an arrangement of fluid openings in an oral insert, where the arrangement of fluid openings may correspond to the location of the gingival margins, interproximal regions, incisal edges, and contours of the occlusal, facial, lingual, mesial and distal surfaces of the teeth. Obtaining oral structure data may comprise acquiring a 3-D dental scan, and/or acquiring X-ray dental images. Calculating the oral surface map may further comprise identifying the location and geometry of oral and/or dental devices or implants, for example, dental devices comprise orthodontic appliances. Generating an arrangement of fluid openings may comprise identifying a size and shape of one or more interproximal regions that are located between the teeth, and positioning a plurality of openings oriented at an angle from about 0° to about 90° relative to a long axis of a tooth and located within about 0 mm to about 10 mm from interproximal regions on either side of the tooth. Alternatively or additionally, generating an arrangement of fluid openings may comprise identifying incisal edges and occlusal, facial, lingual, mesial and distal surfaces of the teeth, and positioning a plurality of openings oriented at an angle from about 0° to about 90° relative to a long axis of a tooth and located within about 0 mm to about 10 mm from a surface of the tooth. In some variations, generating an arrangement of fluid openings may comprise identifying the size and shape of gingival margins, and positioning a plurality of openings oriented at an angle from about 0° to about 90° relative to a long axis of a tooth and located within about 0 mm to about 10 mm from the corresponding planar surface.

BRIEF DESCRIPTION OF THE DRAWINGS

Various embodiments of the invention are disclosed in the following detailed description and the accompanying drawings.

FIG. 1F is a bottom view of a mouthpiece, FIG. 1G is a top view of the mouthpiece of FIG. 1F, and FIG. 1H is a front view of the mouthpiece of FIG. 1F.

FIGS. 3F-3G depict a front view and a perspective view, respectively, of one variation of a three-lobed fluid nozzle or fluid opening.

FIGS. 3H-3I depict a front view and a perspective view, respectively, of one variation of a three-lobed fluid nozzle or fluid opening.

FIGS. 3J-3K depict a front view and a perspective view, respectively, of one variation of a three-lobed fluid nozzle or fluid opening.

FIGS. 3O-3P depict a front view and a perspective view, respectively, of one variation of a two-lobed fluid nozzle or fluid opening.

FIG. 3Q depicts a front view of another two-lobed fluid nozzle or opening.

FIGS. 3R-3S depict a front view and a perspective view, respectively, of one variation of a two-lobed fluid nozzle or fluid opening.

FIGS. 3T-3U depict a front view and a perspective view, respectively, of one variation of a two-lobed fluid nozzle or fluid opening.

FIGS. 3V-3AA depict front views of other variations of a three-lobed fluid nozzle or fluid opening.

FIGS. 4A-4C depict the experimental and simulated cleaning results of a sample set of teeth using a circular or round-shaped fluid opening or nozzle. FIG. 4A is a front view of a sample set of teeth, FIG. 4B represents a simulated cleaning result of the teeth using a computational fluid dynamics model, and FIG. 4C is a side view of the sample set of teeth along the interproximal space.

FIG. 5A is a front view of a sample set of teeth, FIG. 5B represents a simulated cleaning result of the teeth using a computational fluid dynamics model, and FIG. 5C is a side view of the sample set of teeth along the interproximal space.

FIGS. 6A-6C depict the experimental and simulated cleaning results of a sample set of teeth using a V-shaped fluid opening or nozzle. FIG. 6A is a front view of a sample set of teeth, FIG. 6B represents a simulated cleaning result of the teeth using a computational fluid dynamics model, and FIG. 6C is a side view of the sample set of teeth along the interproximal space.

FIG. 10 is a flow chart diagram with corresponding graphical representations of one variation of a method for generating a customized oral insert or mouthpiece with a plurality of fluid openings positioned according to oral structure data.

DETAILED DESCRIPTION

Figure 1A:
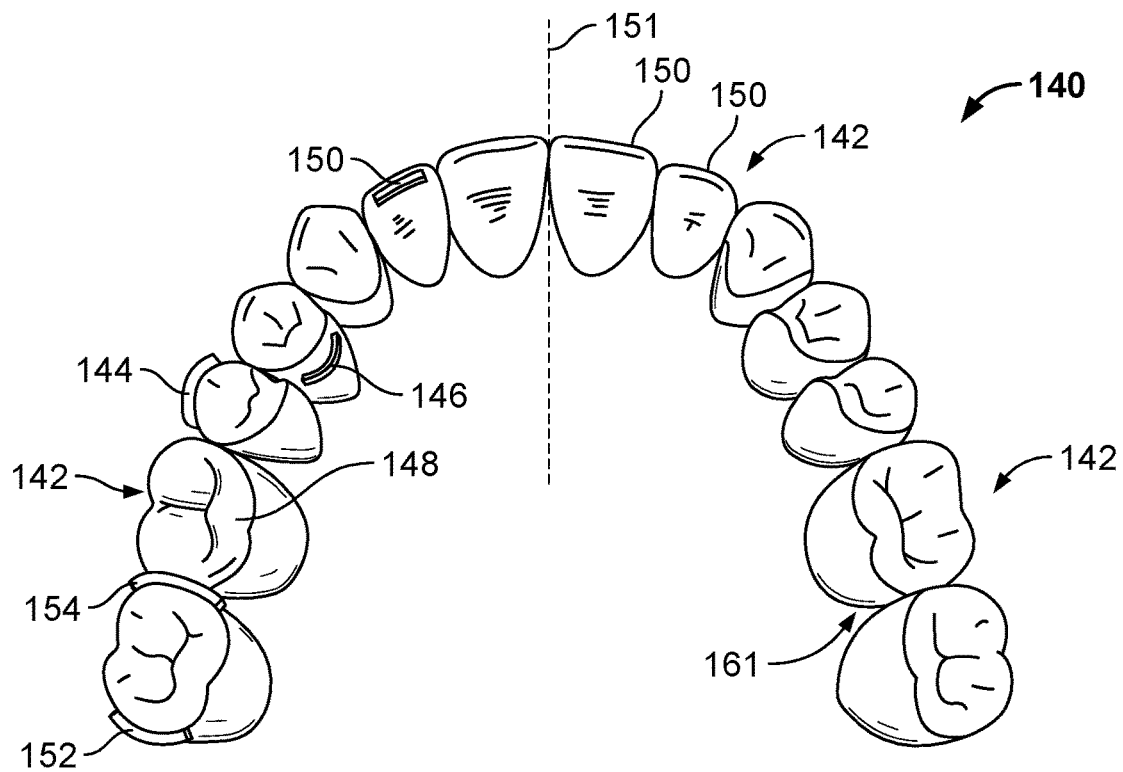
FIG. 1A depicts a top view of the oral anatomy of a user.

The invention can be implemented in numerous ways, including as a process; an apparatus; a system; a composition of matter; a computer program product embodied on a computer readable storage medium; and/or a processor, such as a processor configured to execute instructions stored on and/or provided by a memory coupled to the processor. In this specification, these implementations, or any other form that the invention may take, may be referred to as techniques. In general, the order of the steps of disclosed processes may be altered within the scope of the invention. Unless stated otherwise, a component such as a processor or a memory described as being configured to perform a task may be implemented as a general component that is temporarily configured to perform the task at a given time or a specific component that is manufactured to perform the task. As used herein, the term 'processor' refers to one or more devices, circuits, and/or processing cores configured to process data, such as computer program instructions.

A detailed description of one or more embodiments of the invention is provided below along with accompanying figures that illustrate the principles of the invention. The invention is described in connection with such embodiments, but the invention is not limited to any embodiment. The scope of the invention is limited only by the claims and the invention encompasses numerous alternatives, modifications and equivalents. Numerous specific details are set forth in the following description in order to provide a thorough understanding of the invention. These details are provided for the purpose of example and the invention may be practiced according to the claims without some or all of these specific details. For the purpose of clarity, technical material that is known in the technical fields related to the invention has not been described in detail so that the invention is not unnecessarily obscured.

Described herein are systems and methods for providing personalized oral irrigation. A system for personalized oral irrigation may comprise a fluid reservoir and a customized oral insert in fluid communication with the fluid reservoir. The oral insert may comprise an arrangement of fluid openings positioned to provide a customized fluid flow over a user's teeth. In some variations, the oral insert may be customized to accommodate a user's oral geometry. Fluid egress from the plurality of fluid openings may clean multiple teeth simultaneously and the location and geometry of the fluid openings with respect to specific and unique structures of the user's mouth may help facilitate expeditious and/or effective cleaning of teeth surfaces. In some variations, the oral insert may comprise a custom arrangement of a plurality of fluid openings or nozzles where each of the nozzles is positioned to target a specific dental feature or structure. Also described herein are methods for generating a pattern or arrangement of fluid openings on an oral insert that are customized to a user's teeth and gums, as well as any oral and/or dental devices or implants, for example, permanent and removable dental restorations/prosthetics, orthodontic appliances, etc. (e.g., crowns, bridges, implants, braces, retainers, dentures, and the like). Methods may comprise obtaining oral structure data, identifying particular oral structures (e.g., gingival margins, interdental gingiva, interproximal regions, incisal edges, and contours of the occlusal, facial, lingual, mesial and distal surfaces of the teeth), and generating a pattern or arrangement of fluid openings that correspond to the specific oral structures.

The oral irrigation systems are described in the context of cleaning the teeth and/or disrupting biofilms that may form on or in between the teeth or restorations or around dental appliances, and within the gingival sulcus, but it should be understood that the systems described herein may also be used for the application of medicaments or prophylactics to the oral cavity, teeth whitening, oral disinfection, antiseptic fluids, cleaning fluids, etc.

Figure 1B:
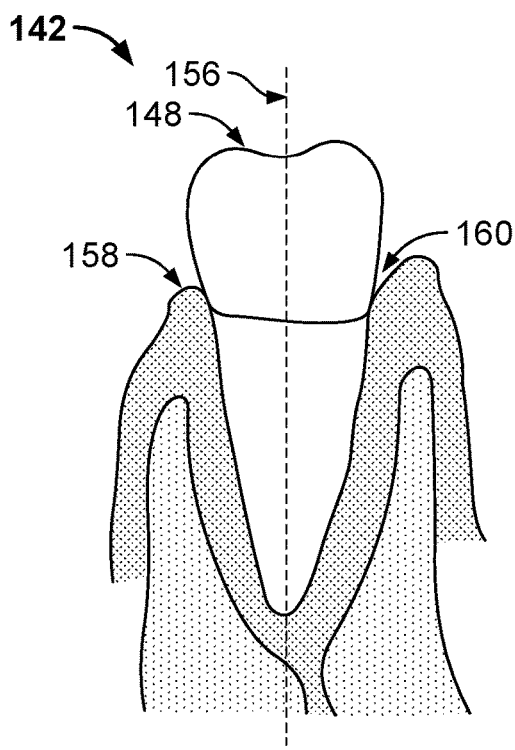
FIG. 1B depicts a partial cutaway side view of a tooth and surrounding gingiva.
Figure 1C:
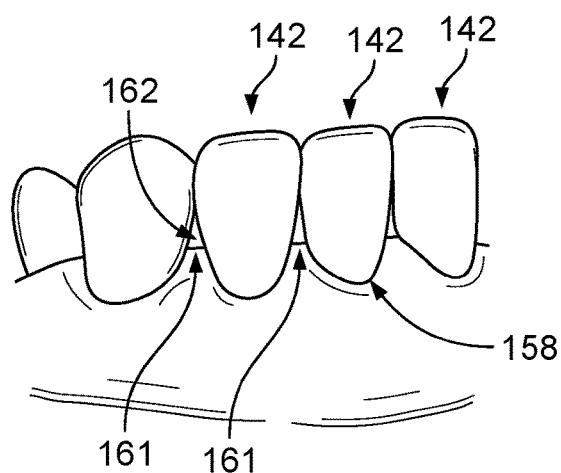
FIG. 1C depicts a side view of teeth and surrounding gingiva.

FIGS. 1A-1C are schematic depictions of oral anatomy and dental structures, illustrating the regions of the oral cavity described herein. FIG. 1A depicts a top view of a set of teeth (140) of the mandible or lower jaw (though similar terminology may be used to refer to the teeth and structures of the maxilla or upper jaw). Each tooth (142) may have a facial surface (144) which is the region of the tooth that contacts the cheeks or lips and a lingual surface (146) which is the region of the tooth that contacts (or is nearest to) the tongue. Facial surfaces may be, for example, the buccal surfaces of the posterior teeth and the labial surfaces of the anterior teeth. Lingual surfaces may also be referred to as the palatal surfaces for maxillary teeth. Posterior teeth may have an occlusal surface (148) and the anterior teeth may have an incisal edge or surface (150). The occlusal (or incisal) surface is the region of the tooth that aids in chewing, and/or faces across from the occlusal (or incisal) surface of the opposing tooth. The surface of a tooth facing away from the arch midline may be referred to as the distal surface (152) while the surface of a tooth facing toward the arch midline (151) may be referred to as the mesial surface (154). FIG. 1B depicts a side view of a single tooth (142), which may have a long axis (156) that extends along the longest dimension of the tooth (142) and/or is substantially perpendicular to the occlusal surface (148) or incisal edge (150) of the tooth. The edge or boundary of the gums (e.g., gingiva, gingival tissue) along the surfaces of the teeth or closest to the occlusal surfaces or incisal edge of the teeth may be referred to as the gingival margin (158). The gingival margin (158) may have one or more curves along the bottom of each tooth, and the radius of curvature and length of the gingival margin for each tooth may vary. A space or region (160) between the gingiva and the surfaces of the tooth may be referred to as a gingival sulcus (160). Interdental gingiva (161) may be the gum tissue located between two adjacent teeth. FIG. 1C depicts a side view of a plurality of teeth (142). The space or gap between each tooth (142) may be referred to as the interproximal space or gap (162), and may be defined by the mesial surface of one tooth and the distal surface of the adjacent tooth, or the mesial surfaces of two teeth, in the case of central incisor teeth. The left side of a user's oral cavity may be the region of the oral cavity that is to the left of the interproximal space between the two central incisors (e.g., to the left of the arch midline), and the right side of a user's oral cavity may be the region of the oral cavity that is to the right of the interproximal space between the two central incisors (e.g., to the right of the arch midline).

Systems

Figure 1D:
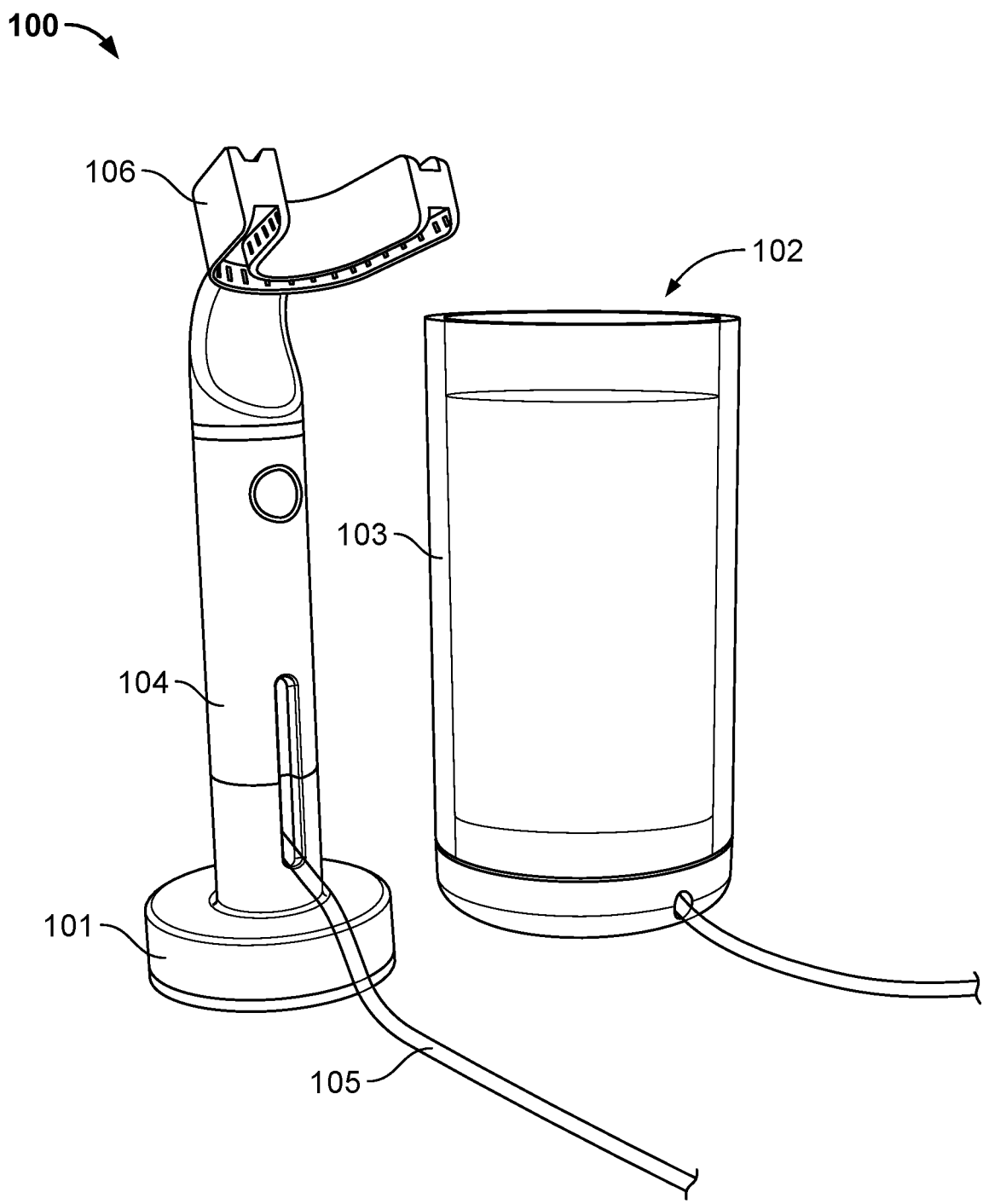
FIG. 1D depicts one variation of a system for providing personalized irrigation.

One variation of a system for personalized oral irrigation is depicted in FIG. 1D. The system (100) may comprise a base station (102) having a fluid reservoir (103), a handle (104), and a customized oral insert or mouthpiece (106) coupled to the handle (104). One or more fluid conduits or tubes (105) may connect the fluid reservoir (103) to the handle (104) and to the mouthpiece (106). The system (100) may optionally comprise a charging station (101) for the handle (104). The handle (104) may comprise one or more control buttons (e.g., a start/stop button, a fluid flow adjustment dial), as may be desirable, which may be positioned variously on the handle for ergonomic or efficient use. Alternatively, or additionally, one or more control buttons may be located on the base station (102). For example, a system may comprise one or more control buttons on the base, and no control buttons on the handle. In other variations, a personalized oral irrigation system may not have a handle at all, and may alternatively comprise one or more fluid conduits or tubes that directly connect the fluid from the base station reservoir to the mouthpiece. The fluid retained in the fluid reservoir of a customized oral irrigation system may be water, saline, a mouth wash or rinse, (e.g., containing fluoride and/or germicidal or other cleaning and/or teeth protective fluids), and/or any other desirable additive. The customized mouthpiece (106) may comprise a plurality of fluid openings or nozzles that are arranged in accordance with the unique geometry of the user's oral cavity, gingival geometry, and dental structures (and any oral and/or dental devices or implants). Examples of oral and/or dental devices or implants may include, but are not limited to, permanent and removable dental restorations/prosthetics, orthodontic appliances, etc. (e.g., crowns, bridges, implants, braces, retainers, dentures, and the like). Each of the fluid openings or nozzles may be positioned to target a specific dental feature. Inside the mouthpiece, the fluid openings or nozzles may be connected to one or more internal manifolds. The inlets of these manifolds may extend from the back of the mouthpiece (or where desirable for ergonomic and/or efficient use) in the form of a standardized connector, to which a handle and/or one or more tubes may be connected.

Customized Oral Insert or Mouthpiece

Figure 1E:
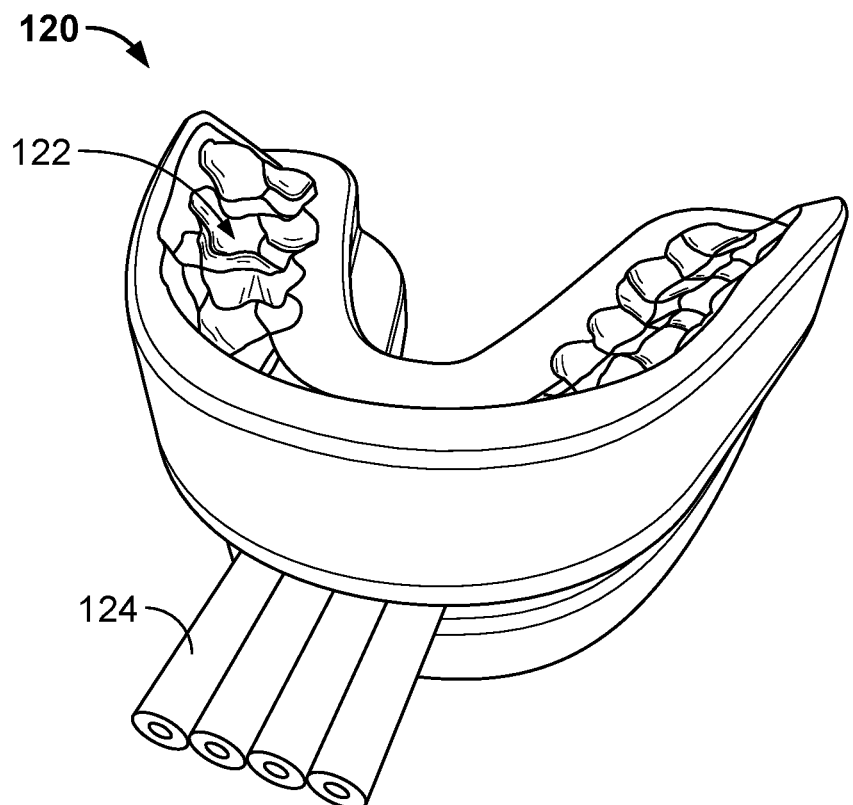
FIG. 1E depicts one variation of a customized mouthpiece or oral insert.

One variation of a customized oral insert or mouthpiece is depicted in FIG. 1E. Mouthpiece (120) may comprise a channel or trough or groove or slot that has one or more contours (122) that correspond with one or more teeth of a user. The contours may be shaped based on optical and/or digital impressions using intraoral scanners or photographs (e.g., 3-D intraoral scans, 3-D scans of a dental impression), photographs, X-rays, physical impressions, intraoral and extraoral radiographs, computed tomography, including cone beam computed tomography, magnetic resonance imaging, ultrasound, and the like. In some variations, a mouthpiece may not have contours corresponding to one or more teeth, but may comprise one or more alignment features to help facilitate correct and consistent placement and alignment of the mouthpiece within the mouth. For example, an oral insert or mouthpiece may comprise a channel or trough or groove or slot defined by two side walls and a bottom wall that are sized to fit around the teeth (e.g., configured to contact facial surfaces, lingual surfaces, and occlusal surfaces of maxillary teeth and/or mandibular teeth). The side walls and bottom wall may have smoothed surfaces and/or contours that may or may not correspond with the anatomical contours of the one or more teeth. In some variations, one or more alignment features may be located within the trough to help seat the teeth within the trough. For example, an alignment feature may comprise protrusions, slots, or recesses that receive and/or articulate with the user's teeth, gums, hard palate, soft palate, other oral structures, and/or may have contours that correspond to one or more teeth. These alignment features may help to ensure that the oral insert is seated in a desired position in the user's mouth. A location of the one or more alignment features is specific to a user, such that, when the oral insert is held in place in the user's mouth, the plurality of fluid nozzles are positioned to target a specific dental feature or structure. For example, the location of the one or more alignment features for a first user is different than the location of the one or more alignment features for a second user because the position of a first plurality of fluid nozzles for the first user is different than the position of a second plurality of fluid nozzles for the second user. This is due to the differences in oral structures between the first and second users.

The location of the one or more alignment features may be determined based on a software model that determines an intersection plane associated with a user's teeth. For the set of teeth associated with the maxilla or upper jaw, the portion of the user's teeth that is above the intersection plane corresponds to an undercut region. The one or more alignment features for an oral insert corresponding to a user's upper jaw is based on a portion of the determined undercut region. For the set of teeth associated with the mandible or lower jaw, the portion of the user's teeth that is below the intersection plane corresponds to an undercut region. The one or more alignment features for an oral insert corresponding to a user's lower jaw is based on a portion of the determined undercut region. The one or more alignment features correspond to some, but not all of the teeth associated with a user. When a user has inserted the oral insert into their mouth, some of their teeth (e.g., molars, premolars, canines, incisors) are in contact with the oral insert. Unlike a sports mouthguard where substantially all of the exterior and bottom surface area of a user's teeth are in contact with the mouthguard, having some of the bottom surface area of the user's teeth in contact with the oral insert provides an opening for fluid within the oral insert to flow from a fluid nozzle to the effluence port. In some embodiments, the surface area of a bottom portion of a user's top teeth that contacts the oral insert is less than a particular percentage (e.g., less than 50%) or a particular amount. In some embodiments, the surface area of a top portion of a user's bottom teeth that contacts the oral insert is less than a particular percentage (e.g., less than 50%) or a particular amount.

Figure 1F:
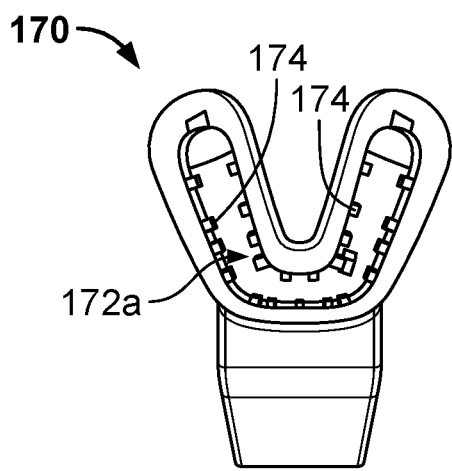
FIGS. 1F-1H depict one variation of a customized mouthpiece or oral insert, where
Figure 1G:
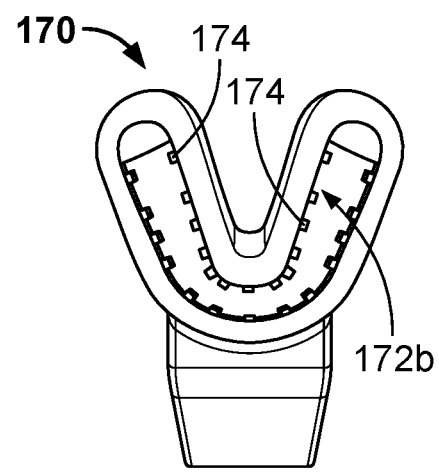
Figure 1H:
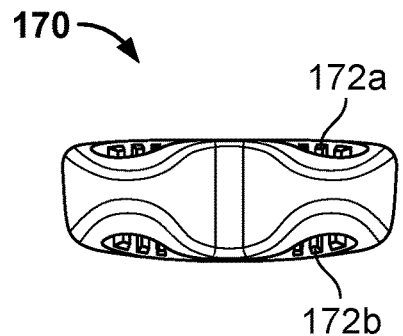

FIGS. 1F-1H depict one variation of an oral insert or mouthpiece (170) comprising a trough (172a and/or 172b) that has a curve that corresponds with the curve of the maxillary teeth or mandibular teeth (i.e., teeth along the curve of the maxilla or mandible). For example, the maxillary (or mandibular) teeth may be located on the maxilla (or mandible) along a curve, and a curved trough of the oral insert may approximate that curve. While some variations of the oral insert may comprise a trough having contours that match the anatomical contours of a user's teeth, in this variation, the interior walls of the trough (172a and/or 172b) may have smooth surfaces and/or contours or features associated with the size, shape, placement and alignment of the fluid openings or nozzles with respect to a user's teeth. For example, a plurality of fluid openings or nozzles (174) may be located within the trough, for example, along the two side walls of the trough for providing fluid flow to the facial and/or lingual surfaces of the teeth. The fluid openings or nozzles (174) may include protrusions (as depicted in FIGS. 1F and 1G) that extend into the space of the trough, or may be flush along or recessed relative to the inner surface of the side walls of the trough. As will be described further below, the fluid openings or nozzles (174) may be positioned at customized locations to direct fluid to specific regions of the teeth. For example, some fluid openings or nozzles may be located across from the interproximal spaces, and/or along the gingival margins. In some variations, the spacing or distance between the fluid openings or nozzles may correspond with the distance between the interproximal spaces or the size and shape of the teeth.

While some oral inserts or mouthpieces may comprise a single trough to fit over either the maxillary teeth or the mandibular teeth, in other variations, an oral insert or mouthpiece may comprise two opposing troughs where one trough accommodates the maxillary teeth and the other trough accommodates the mandibular teeth (i.e., so that both upper (maxillary) and lower (mandibular) teeth may be irrigated simultaneously or in series with a single mouthpiece). For example, as depicted in FIG. 1H, the mouthpiece (170) comprises a first trough (172a) that may be configured to fit over the mandibular teeth (e.g., a lower trough) and a second trough (172b) opposite the first trough that may be configured to fit over the maxillary teeth (e.g., an upper trough). A first set of fluid openings or nozzles may be located within the first trough (172a) to provide customized fluid flow to the mandibular teeth and a second set of fluid openings or nozzles may be located within the second trough (172b) to provide customized fluid flow to the maxillary teeth. In some variations, fluid openings or nozzles may be provided only in regions of the oral cavity for which fluid irrigation or infusion is desired. For example, some variations may comprise separate mouthpieces that each provide fluid flow to a select subset of teeth. This may be useful for applications other than cleaning, for example, the targeted application of medicine, whitening solutions, etc. Any of the fluid openings or nozzles described herein may be used in either or both of the troughs for providing customized fluid flow for each of the mandibular teeth and the maxillary teeth.

Alternatively, or additionally, some systems may comprise two or more of any of the oral inserts or mouthpieces described herein. For example, some systems may comprise a first mouthpiece for providing fluid flow for the maxillary teeth and a second mouthpiece for providing fluid flow for the mandibular teeth. The system may comprise a single base station, and may have either one handle (where the first and second mouthpieces may be removably attached to the handle) or two handles (where the first mouthpiece is attached to a first handle and the second mouthpiece is attached to a second handle). Alternatively or additionally, a system may have a first mouthpiece that has a first set of fluid openings or nozzles that are arranged to provide fluid flow to the interproximal spaces of the teeth (e.g., for a flossing function or effect) and a second mouthpiece that has a second set of fluid openings or nozzles that are arranged to provide fluid flow across the facial and/or lingual and/or occlusal surfaces of the teeth (e.g., for a brushing or surface cleaning function or effect). The first (e.g., flossing function) mouthpiece and the second (e.g., brushing function) mouthpiece may have two troughs for cleaning both the upper teeth and lower teeth simultaneously or in series, as described for the variation depicted in FIGS. 1F-1G. Alternatively, some systems may comprise a first mouthpiece that has two troughs that accommodate the upper and lower teeth on a left side of a user's oral cavity and a second mouthpiece that has two troughs that accommodate the upper and lower teeth on a right side of a user's oral cavity. Similarly, the system may comprise a single base station and one or two handles, as described above.

The oral inserts or mouthpieces described herein may comprise a plurality of fluid openings or nozzles arranged based on the individual geometry of a user's oral cavity and dental structures. Customizing the position of the nozzles with respect to specific dental structures may help facilitate cleaning efficacy. Cleaning efficacy may be achieved by generating a shear stress greater than the critical shear stress (i.e., a shear stress threshold) at which biofilm or residue may be removed from the target surface or feature (e.g., tooth or gum structure). If a nozzle is incorrectly aligned relative to the dental and/or gum structures of a user, fluid jets may be improperly applied to the teeth or gum structures, which may detract from cleaning efficacy and in some cases, may even push debris into a gum pocket (instead of flushing debris out of a gum pocket). The positions of the nozzles in the arrangement of nozzles may be determined by locating the dental or gum feature(s) targeted by the one or more nozzles, orienting the nozzle such that the applied fluid jet moves across or toward the feature such that biofilm or debris on the feature is disrupted or removed, and positioning the nozzle at a location such that fluid from the nozzle strikes the feature in a controlled fashion (e.g., with a consistent flow or pulsatile flow) to overcome the shear stress threshold at which biofilm or residue may be removed from the target surface or feature (e.g., tooth or gum structure). In some variations, customized arrangement of nozzles may take into account any irregular tooth anatomy and/or orthodontic appliances, including supernumerary teeth, missing or unerupted teeth, fusion (when two developing teeth merge into one tooth—usually forming a groove that is prone to decay), germination (when a developing tooth splits into two teeth—usually forming grooves that are prone to decay), partially erupted teeth, and numerous other formation or eruption issues that may cause irregular geometries. The customized fluid opening or nozzle arrangements of the present invention may accommodate and clean the extra surfaces, interproximal regions, gingival margins, ridges, grooves, pits, and fissures that might otherwise be missed by non-customized mouthpieces or devices (i.e., mouthpieces having fluid openings or nozzles that are not arranged based on a user's oral and dental structures).

The oral inserts or mouthpieces described herein may also accommodate changes in dental geometry. For example, a user may have a broken or missing tooth, and/or may have new teeth or restorations. Some variations of a mouthpiece may include one or more shields that may have curves and/or contours that correspond to the surface contours of one or more of the user's teeth. The shields may be mechanically attached or chemically bonded into the space or cavity of the mouthpiece that corresponds to the missing or broken tooth, and may extend from the mouthpiece up to the gingival margin (e.g., a few millimeters over the gingival margin). The shields may help prevent fluid jets intended for the missing or broken tooth from striking the recess where the tooth was previously located. The shields may also be used to shield especially sensitive teeth or gums (e.g., due to tooth decay, retained roots, partially erupted teeth, and/or after a dental procedure) from fluid jets, as may be desirable for user comfort.

While the fluid openings or nozzles are described herein in the context of fluid ingress (i.e., introducing fluid into the oral cavity), it should be understood that one or more of the fluid openings or nozzles may be used for fluid egress (e.g., channeling fluid out of the oral cavity and/or coupled to a suction or vacuum chamber), as may be desirable.

The oral insert or mouthpiece described herein may be manufactured utilizing one or more 3-D Printing (also known as Additive Manufacturing) processes which may include: Stereolithography Apparatus (SLA), Polymer Jetting, Powder Deposition, Binder Jetting, Selective Laser Sintering (SLS), Fused Deposition Modeling (FDM), Fused Filament Fabrication (FFF), Directed Energy Deposition (DED), Direct Metal Laser Sintering (DMLS), Selective Laser Melting (SLM), Electron Beam Melting (EBM), Laminated Object Manufacturing (LOM), Rapid Liquid Printing (RLP), BioPrinting, Self Assembly Printing (also known as 4D printing) or a hybrid system that utilizes a variety of 3D printing processes. Manufacturing may also include a hybrid process that utilizes 3D Printing and robotics, 3D printing and conventional manual milling or Computer Numerically Controlled (CNC) machining, or 3D printing and injection molding or over-molding. Manufacturing may also include a system for varying hardness, flexibility, color, or texture depending upon the process and materials used. Materials may include, UV-curable photopolymers such as 3D Systems™ VisiJet SL Clear™, 3DSystems™ Accura ClearVue™, NextDent™ Model Clear™ or Stratasys™ Med620™, UV curable ceramics, powder polymers, powder metals, powder alloys, powder ceramic, powered organic material, filament-based plastics, filament-based metals, filament-based ceramics, filament-based organic materials, or may be comprised of a variety of plastic, metal, ceramic, organic materials or biological materials that may be grown in a laboratory environment which may be end user specific or manufactured from a specific user's genetic data or cells as a base material. A template for a customized mouthpiece may specify the curves and contours of the mouthpiece to accommodate a user's teeth and oral cavity, as well as the location, number, shape and size of the arrangement of fluid openings or nozzles.

Figure 1I:
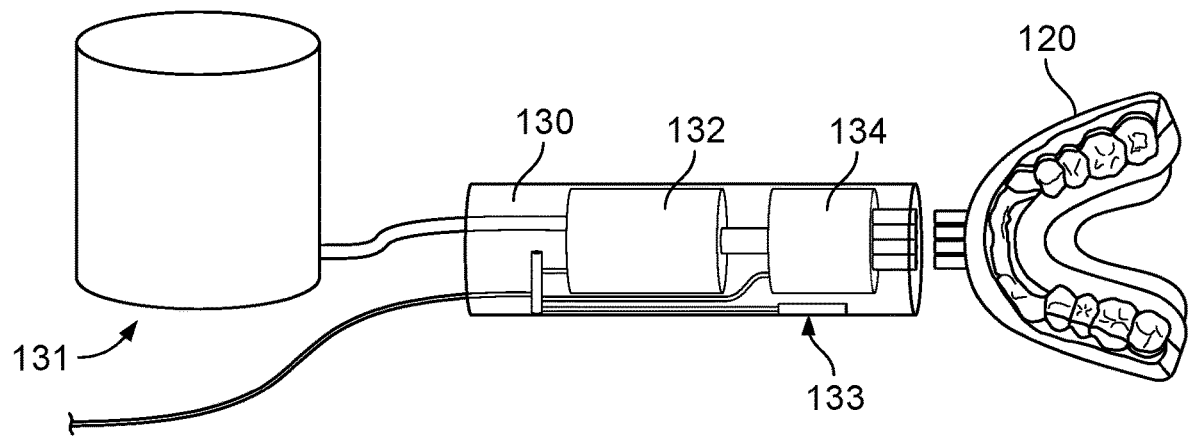
FIG. 1I depicts a fluid flow pathway between a fluid reservoir, handle, and a customized mouthpiece or oral insert.

Mouthpieces (120, 170) may comprise one or more internal fluid cavities or manifolds connected to the fluid openings or nozzles, and the fluid inlets (124) to the manifolds may extend from the mouthpieces (120, 170) to engage with fluid ports of a handle and/or fluid conduits or tubes. One variation of a handle is depicted in FIG. 1I. Handle (130) may comprise a pump (132) and a switching manifold (134), both of which are in fluid connection with the base station reservoir and enclosed within a handle housing. In variations where the oral insert comprises a plurality of manifolds, the switching manifold (134) of the handle may multiplex and/or regulate fluid flow in each of the plurality of manifolds. Handle (130) may also comprise an electronics control board and one or more user inputs or control buttons, which may be in communication with the electronics control board. The electronics control board may receive and/or relay commands to regulate the fluid flow into the handle and to the mouthpiece. Optionally, some variations of a handle or reservoir may comprise one or more heating elements. The heat element may be adjusted by a user (in a pre-programmed or real-time fashion) to set the temperature of the fluid at a comfortable level. In some variations, the temperature of the fluid may be set at levels to improve cleaning efficacy (e.g., higher temperatures may help facilitate removal of hydrophobic food or biofilm residues, such as residues with fatty acids and/or oils, and/or dissolve and/or soften hardened food residues), and/or increase chemical activity of entrained, therapeutic additives. A system may comprise one or more thermal control units (e.g., a heater or chiller) at various locations within the system, for example, in the base of the reservoir (location 131) and/or in the pump (132) and/or switching manifold (134). For example, a heating element may comprise an electrical-resistance type heating element, and/or a cooling element may be a thermoelectric cooler (e.g., a solid-state device such as a Peltier device). The heating and/or cooling element (133) may be located within the handle (130) and may be thermally connected to one or more of the pump and/or switching manifold and/or reservoir. Alternatively or additionally, the fluid may also be heated by thermal energy generated by a pump motor (e.g., pump (132)). The heat byproduct generated by the electric motor (e.g., generated within the copper electrical motor windings) may be used to heat the fluid to a desired and/or beneficial temperature. As the fluid moving through the motor may carry the heat energy away from the motor, this may have the additional benefit of simultaneously cooling the motor itself. In some variations, the fluid may be routed directly through the copper motor windings (i.e., the fluid is in direct contact with the surface of the electrical conductors), or it could be routed through a specifically-engineered "water jacket" (e.g., fluid channels) around, inside, or otherwise in thermal communication with the heat-generating copper motor windings. Alternatively or additionally, heat generated by the electronics (e.g., motor drive semiconductors, computer processor of the base station) may also be used to heat the fluid as it passes through the system.

Described below are examples of fluid opening or nozzle arrangements that are customized to particular dental structures or features. While the position of the fluid openings or nozzles may be tailored to target one dental structure or feature, it should be understood that the position of fluid openings or nozzles may be determined based on optimizing fluid flow and/or biofilm or debris removal from more than one dental structure or feature.

Figure 1J:
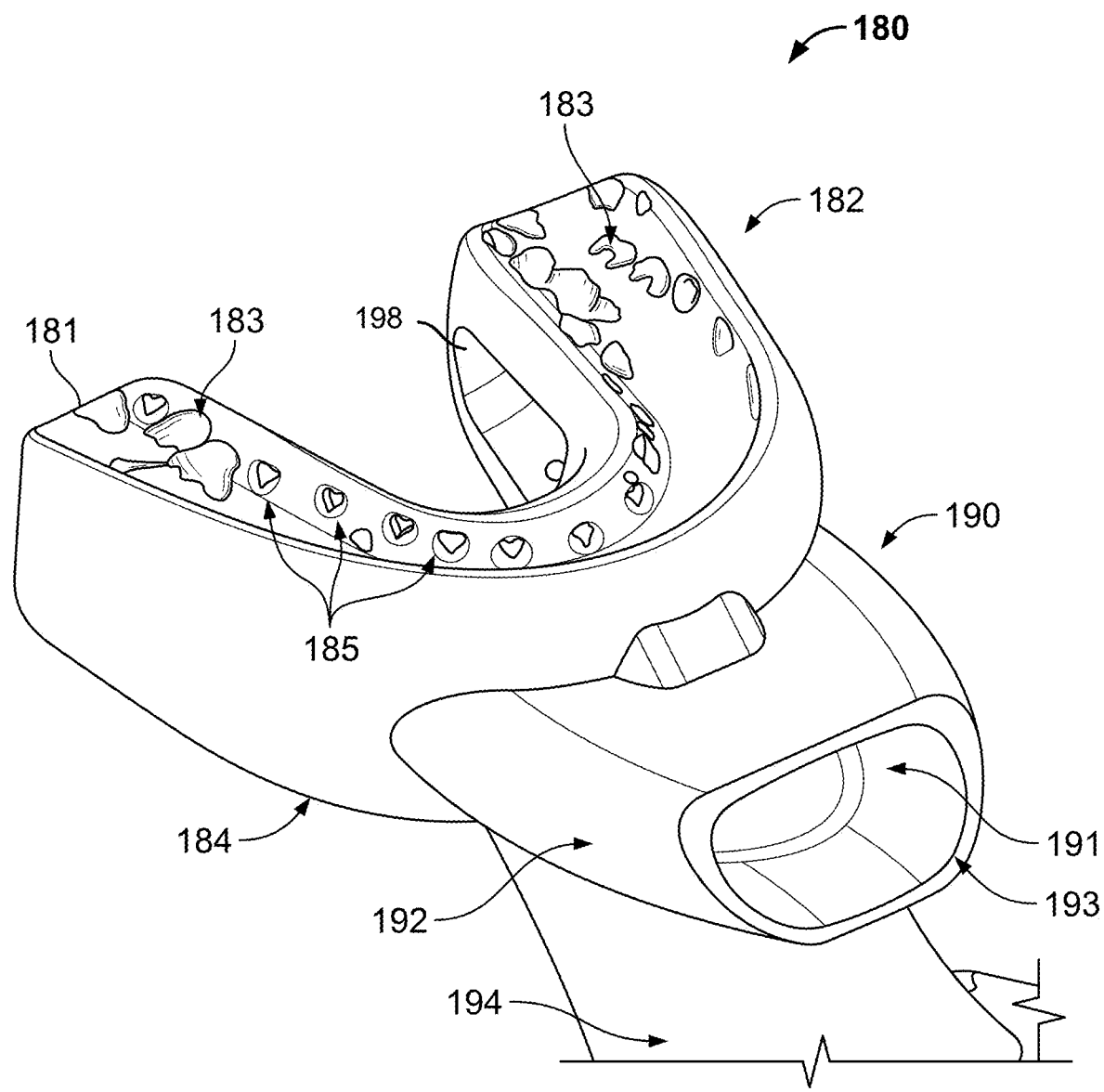
FIG. 1J depicts a perspective view of an oral insert in accordance with some embodiments.

FIG. 1J depicts one variation of an oral insert (180). The oral insert (180) may be made of a rigid material, and may comprise an upper portion (182) having a tray configured to receive a user's upper teeth, a lower portion (184) having a tray configured to receive a user's lower teeth, a plurality of fluid nozzles (186) located in the upper portion and the lower portion, and an effluence conduit (190) located between the upper portion and the lower portion. The trays of the upper and lower portions may comprise one or more alignment features (183), which may comprise protrusions, slots, or recesses that receive and/or articulate with the user's teeth, gums, hard palate, soft palate, other oral structures, and/or may have contours that correspond to one or more teeth. These alignment features may help to ensure that the oral insert is seated in a desired position in the user's mouth. In some variations, one or more of the fluid nozzles (186) may be located in recesses or indentations (185) along the teeth- and/or gingiva-facing surfaces of the upper and lower trays. The recesses (185) and the fluid nozzles (186) may be located at regions of the upper and lower trays that correspond with the interproximal spaces between the user's teeth, and/or at locations that allow the fluid nozzles to direct fluid jets to the interproximal spaces (e.g., that may not necessarily correspond with the locations of the interproximal spaces). The recesses (185) may have a flared or tapered shape, and/or may have one or more concave contours, where the fluid nozzle opening is located at the narrow portion of the recess. The width of the recess may increase as it extends outward from the fluid nozzle opening. The increased width of a flared recess may allow the fluid jet spray to expand unimpeded. In some variations, the central axis of the flared recess may be aligned with the direction of the fluid jet. The effluence conduit (190) may comprise a central port or channel (191) which may extend between a posterior region via posterior opening 198 and anterior region of the oral insert, and may protrude forward at the anterior region as a beak or an elongated spout (192) that terminates at a fluid egress opening (193). The fluid exiting the central port or channel (191) may be provided to a sink or other collection device (e.g., a collector for microbiomes). The central port or channel (191) is configured to have a minimum cross-section area that causes the fluid outputted from effluence conduit (190) to have a particular pressure. The minimum cross-section area is needed to prevent a high back-pressure that would cause discomfort for the user (e.g., a choking feeling) when using oral insert (180). In some embodiments, the particular pressure is 0.05 psi±a threshold pressure. Alternatively or additionally, an effluence conduit may comprise a first side fluid cavity or channel and a second side fluid cavity or channel. The side fluid cavities may funnel into the central port, or may each have their own elongated spouts with separate fluid egress openings. The shape, sizing, and surface contours of the effluence conduit may be configured according to the user's oral anatomy (e.g., size and size of oral cavity, location of teeth, etc.) and configured to promote fluid dynamic efficiency in draining the fluid from the user's mouth. In some variations, the fluid delivered to the user's mouth may be pressurized and/or delivered at a high fluid rate in order to effectively clean their teeth and/or dislodge particles trapped in the interproximal spaces. Because of the increased rate and/or pressure of fluid flow into the oral cavity (i.e., fluid ingress), the effluence conduit of the oral insert may be sized and shaped to allow for fluid egress at the same or greater rate as fluid ingress. The oral insert (180) may also comprise one or more fluid manifolds, which may be a series of branched and/or networked internal fluid channels that distribute the fluid from the handle to the individual fluid nozzles. The fluid manifolds may terminate at a series of manifold openings in a manifold connector port (194) of the oral insert. In some variations, the manifold connector may have one opening per fluid manifold, or may have more than one manifold opening per fluid manifold. When the oral insert is connected to the handle, the fluid regulator components may be configured to fluidically engage with the manifold connector such that the fluid regulator controls the fluid flow into the manifolds. Optionally, the fluid regulator in the handle may further comprise a manifold block having a plurality of fluid channels that are configured to be aligned with the manifold openings in the manifold connector.

Fluid Opening or Nozzle Placement Customized for Teeth Surfaces

Figure 2A:
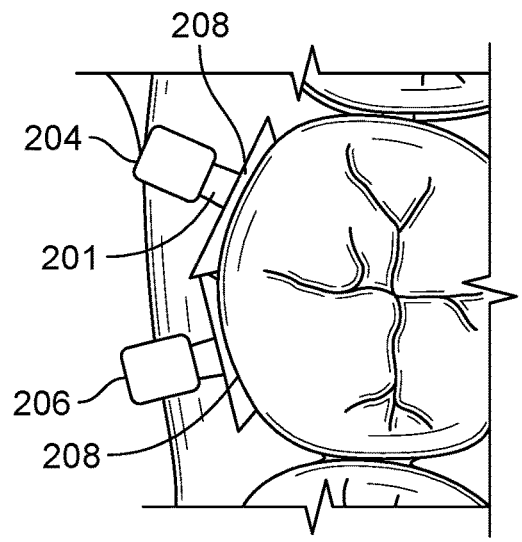
FIGS. 2A-2B are top views of teeth (above the occlusal surface of the teeth) and examples of fluid jets applied by different arrangements of fluid nozzles or openings.

An oral insert and/or mouthpiece may comprise one or more sets of fluid openings or nozzles for removing biofilm or debris from the surface of a tooth (e.g., the contours of the occlusal, facial, lingual, mesial and distal surfaces of the teeth). In one variation, the fluid openings or nozzles for removing biofilms and/or debris from a tooth's surface may be oriented approximately perpendicular to the surface and placed within a predetermined distance (e.g., from about 0 mm to about 10 mm) of the tooth (to overcome a shear stress threshold of greater than approximately 0.014 psi across the target region). Alternatively or additionally, the fluid openings or nozzles may be oriented at any angle between 0° to about 90° relative to the long axis of a tooth, e.g., from about 0° to about 30° (for example, for back molars), from about 35° to about 55°, from about 45° to about 90°, about 45°, etc. FIG. 2A is a diagrammatic representation of fluid openings or nozzles in positions that may provide adequate or consistent fluid flow for removing biofilm or debris (e.g., food residue) from a facial surface or lingual surface of a tooth. As depicted there, fluid openings or nozzles (204) and (206) of an oral insert may each be positioned about 1 mm away (to overcome a shear stress threshold of greater than approximately 0.014 psi across the target region) from the tooth surface (208), for example, the lingual and/or facial surfaces, and oriented such that the fluid jet (201) is approximately perpendicular to the tooth surfaces (208). Alternatively or additionally, the fluid openings or nozzles may be oriented at any angle between 0° to about 90° relative to the long axis of a tooth, e.g., from about 0° to about 30°, from about 35° to about 55°, from about 45° to about 90°, about 45°, etc. In some variations, at least some of the fluid openings or nozzles (204, 206) may be aligned relative to the lingual and/or facial surfaces of the teeth, and/or located between the interproximal spaces of the teeth (i.e., not aligned relative to the interproximal spaces of the teeth). For some variations of an oral insert and/or mouthpiece that is intended to simulate the effect of brushing or cleaning the lingual and/or facial and/or occlusal tooth surfaces, some or all of the fluid openings and/or nozzles may be aligned relative to the lingual and/or facial surfaces and few (if any) fluid openings or nozzles are aligned relative to the interproximal spaces. Nozzles may be located along the mesial or distal sides of teeth if no adjacent tooth is present. In some variations, fluid openings or nozzles may be located at an angle from about 0° to about 90° relative to a long axis of a tooth, e.g., from about 0° to about 30°, from about 20° to about 35°, from about 35° to about 55°, from about 45° to about 90°, about 45°, etc. The shape of the fluid opening may be any shape described herein (e.g., as described further below and depicted in FIGS. 3A-3AA).

Fluid Opening or Nozzle Placement Customized for Interproximal Surfaces

Figure 2B:
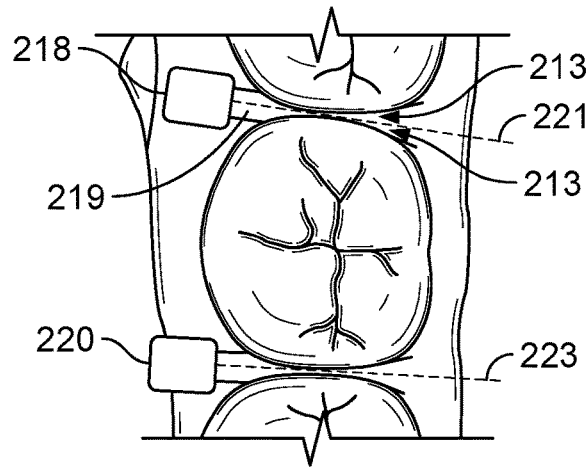

An oral insert and/or mouthpiece may comprise one or more sets of fluid openings or nozzles for removing biofilm or debris from interproximal surfaces. In one variation, the fluid openings or nozzles for removing biofilm and/or debris from a tooth's surface, including supragingival and subgingival regions, may be oriented parallel to the tangents of the interproximal region and positioned within a predetermined distance (e.g., from about 0 mm to about 10 mm) from the interproximal region (to overcome a shear stress threshold of greater than approximately 0.014 psi across the target region). The shape of the opening or nozzle may also be selected such that the resultant fluid jet has a width and height that corresponds with a width and height of the interproximal region, including the shape of the interdental gingiva, allowing for adequate shear stress distribution on the targeted region. FIG. 2B is a diagrammatic representation of fluid openings or nozzles in positions that may provide adequate or consistent fluid flow for removing biofilm and/or debris from interproximal surfaces (213). As depicted there, nozzles (218) and (220) may each be oriented along and/or parallel to a tangent (221) and (223) respectively of the interproximal surfaces (213) of two teeth, such that the fluid jet (219) may be approximately perpendicular to the interproximal tooth surfaces. Alternatively, or additionally, the fluid openings or nozzles may be oriented such that the fluid jet may have any angle between 0° to about 90° relative to the long axis of a tooth, e.g., from about 0° to about 30° (for example, for back molars), from about 35° to about 55°, from about 45° to about 90°, about 45°, etc. In some variations, at least some of the fluid openings or nozzles (218, 220) may be aligned relative to the interproximal spaces between the teeth (i.e., not aligned relative to the lingual and/or facial surfaces of the teeth). For some variations of an oral insert and/or mouthpiece that is intended to simulate the effect of flossing and/or removing residue from the interproximal spaces, some or all the of the fluid openings and/or nozzles may be aligned relative to the interproximal spaces and few (if any) fluid openings or nozzles are aligned relative to the lingual and/or facial surfaces. In some variations, fluid openings or nozzles may be located at an angle from about 0° to about 90° relative to the long axes of the teeth adjacent to the interproximal space, e.g., from about 0° to about 30, from about 35° to about 55°, from about 45° to about 90°, about 45°, etc. The shape of the fluid opening may be any shape described herein (e.g., as described further below and depicted in FIGS. 3A-3AA).

Fluid Opening or Nozzle Placement Customized for Gingival Margins

Figure 2C:
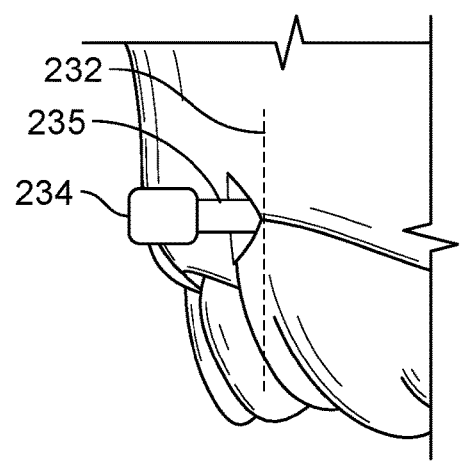
FIG. 2C is a side perspective view of teeth and their gingival margins, and examples of fluid jets applied by different arrangements of fluid nozzles or openings.

An oral insert and/or mouthpiece may comprise one or more sets of fluid openings or nozzles for removing biofilm or debris from gingival margins (including supragingival, and/or subgingival regions, and/or gingival sulci). In one variation, the fluid openings or nozzles for removing biofilms from a tooth's surface may be oriented upwards at any angle from about 0° to about 90°, e.g., about 70° to about 110°, about 90°, relative to the tooth's surface at the gingival margin (or the long axis of the tooth) and placed within about 0 mm to about 10 mm of the gum line (to overcome a shear stress threshold of greater than approximately 0.014 psi across the target region). FIG. 2C is a diagrammatic representation of fluid openings or nozzles in positions that may provide adequate or consistent fluid flow for removing biofilm from a gingival margin. As depicted there, nozzle (234) may be oriented such that the resultant fluid flow (235) is any angle from about 0° to about 90°, e.g., about 70° to about 110°, about 90°, to the surface (represented by the dotted line 232) of the tooth at the gingival margin or long axis of the tooth (e.g., parallel to 232), which may help prevent damage to gingival attachment to the tooth. In some variations, fluid openings or nozzles may be located at an angle from about 0° to about 90° relative to a long axis of a tooth. The shape of the fluid opening may be any shape described herein (e.g., as described further below and depicted in FIGS. 3A-3AA).

Nozzle Design for Customized Fluid Profiles and Coverage

Figure 3A:
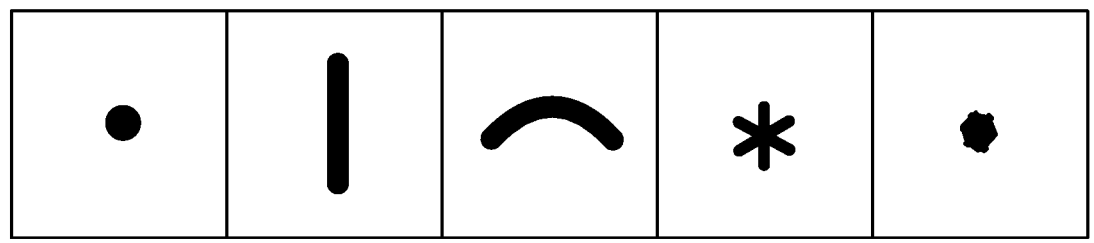
FIG. 3A depicts variations of fluid nozzle or opening shapes.
Figure 3B:
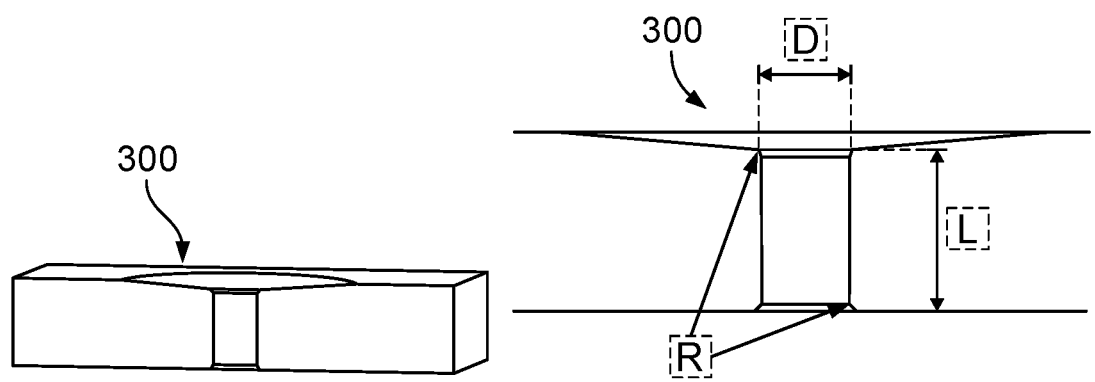
FIG. 3B provides cross-sectional views of one variation of a fluid nozzle or opening.

The shape of the fluid openings or nozzles may be selected to expand the area that is covered by a fluid jet, and/or adjust the fluid pressure or shear stress distribution at a local tooth surface. Examples of fluid opening or nozzle shapes (as viewed along the fluid path, face-on, along the central axis of the opening) are depicted in FIG. 3A. A fluid opening may be shaped as a circle (where the diameter may be adjusted per a user's oral geometry), a line (which may be located in alignment with an interproximal space and may have a length that corresponds with a dimension, e.g., length, of an interproximal space), a curve or arc (where the length and radius of curvature may be adjusted per the length and curvature of the user's gingival margins, which may vary on a tooth-by-tooth basis). A fluid opening may also have a multi-linear and/or multi-lobular radial shape and/or an irregular shape that may be tailored according to the geometry of the user's dental geometry. In some variations, identified dental or oral structures may be mapped to specific opening or nozzle shapes. Optionally, the lengths and contours of each nozzle could be adjusted to match individual oral features of the user and/or to tune the fluid coverage area to accommodate individual oral features. Alternatively, or additionally, the shape of a fluid opening or nozzle may be selected from a library of tunable designs and/or tuned to match individual oral features. For example, as depicted in FIG. 3B, tunable parameters of a circular or spot shaped nozzle (300) may include, but are not limited to, orifice diameter (D), length (L), and fillet radii (R). For example, the diameter (D) may be from about 0.2 mm to about 1.5 mm. Alternatively or additionally, the size and shape of a fluid opening or nozzle may be determined by defining the desired fluid jet coverage area, the resultant shear stress, fluid jet velocity, pressure or flowrate, and iterating through variations of tunable parameters to arrive at a completely custom nozzle geometry. For example, fluid jets from the nozzles may generate shear stresses of greater than approximately 0.014 psi on the targeted region, pressures from about 10 psi to about 150 psi, and flowrates from about 0.3 l/min to about 20 l/min.

Figure 3C:
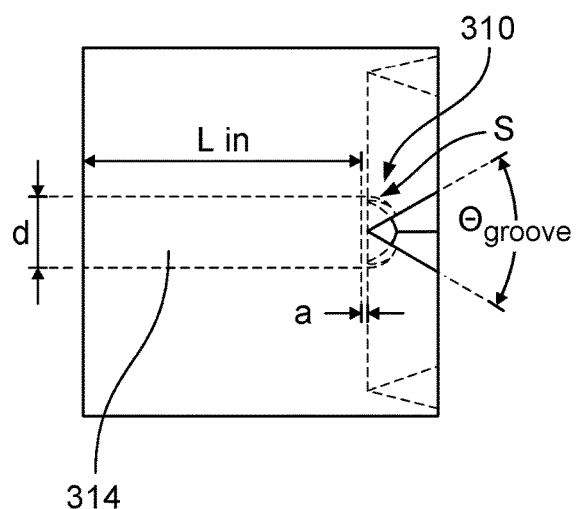
FIGS. 3C-3E depict a cross-sectional view, a front view, and a perspective view, respectively, of one variation of a three-lobed fluid nozzle or fluid opening.

FIGS. 3C-3AA depict various fluid opening or nozzle shapes and geometries that may be used in an oral insert or mouthpiece, alone or in combination with fluid openings of different shapes and sizes, as may be desirable. A fluid opening or nozzle may be connected to an internal manifold within the oral insert or mouthpiece via a channel or lumen. The channel or lumen may be shaped as a cylinder and may have a length (Lin) and a diameter (d). The length (Lin) may be from about 20 mm to about 20 mm, and the diameter (d) may be from about 2 mm to about 5 mm. A first end of the channel may connect to an internal manifold while the second end of the channel may terminate in an opening (i.e., fluid opening) having a size and shape that may be customized to the user's teeth. In some variations, there may be a curved surface(S) disposed over at least a portion of the fluid opening. For example, the curved surface(S) may be defined as a hemisphere with a diameter d, or as an ellipsoid where one of its semi-axes is of a length d/2. In some variations, the fluid opening may have a multi-lobular shape having N lobes and where the lobes have an angular distribution ($\Phi_1 \ldots \Phi_{N-1}$). In some variations, there may be N number of V-grooves with a specified groove angle ($\theta_{groove}$) and an offset (a) of the V-grooves. The number and orientation of the lobes may be customized based on oral anatomy and desired fluid flow profile over that oral anatomy. For example, the diameter (d), groove angle ($\theta_{groove}$), and groove offset (a) may be adjusted to attain a fan jet that increases in width as it travels outward from the fluid opening with a desired fluid sheet thickness (e.g., dimension or extent of the fan jet that is perpendicular to its travel direction) and spray angle (e.g., angular span of the fan jet). For example, diameter (d) may be from about 2 mm to about 5 mm as described above, groove angle ($\theta_{groove}$) may be from about 10° to about 170°, and groove offset (a) may be from about 0 mm to about 3 mm. The customization of these parameters may facilitate the customization of a fluid flow profile according to the geometry of the oral features (e.g., facial, lingual, and/or occlusal surfaces, and/or interproximal spaces and/or gingival margins) of any individual tooth or group of teeth that are desired to be irrigated or cleaned. For example, when the fluid openings and/or nozzles are targeting interproximal regions and gingival margins of the tooth, the angular distribution of the lobes ($\Phi_1 \ldots \Phi_{N-1}$) may be determined by the angle of the interdental gingiva. The dimensions of the nozzle or fluid openings described above may be adjusted based on the geometry of the gingival margins adjacent to the targeted interproximal space and/or the desired depth of penetration into the gingival sulcus to attain a spray angle and sheet thickness that removes biofilm and debris from the interproximal space.

Fluid openings with a three lobe multi-lobe shape may be suitable for directing fluid through interproximal spaces to facilitate a flossing effect and/or to remove debris or residue from between teeth. The lobes may be arranged to correspond with the vertical and/or horizontal extent or dimension of an interproximal space and interdental gingiva. For example, to the extent that the shape of the interproximal space between most teeth can be approximated by a triangle, one or more lobes may approximate the vertical dimension or height of the triangle (i.e., the vertical dimension of the interproximal space that is parallel to the long axis of the tooth), and one or more lobes may approximate the horizontal dimension of the triangle (i.e., the horizontal dimension of the interproximal space that is perpendicular to the long axis of the tooth). In some variations, the fluid opening may have a multi-lobe shape where the lobes are radially arranged around a center of the fluid opening. Angular separation between lobes may be uniform (e.g., three lobes with angular separation of 120° between each, four lobes with angular separation of 90° each, etc.) or may vary (e.g., three lobes where two lobes have an angular separation of 180° and the third lobe has an angular separation of 90° from the other two, i.e., T-shaped). In some variations, the lobes may not be radially symmetric (e.g., two lobes having a 120° angle between them). Widths of each of the lobes may be the same or different from each other, depending on the geometry of the interproximal space between the individual teeth. Each lobe may have a width (i.e., the dimension that is perpendicular to the radial axis) and the width may be uniform across the length of the lobe or may vary across the length of the lobe. For example, some multi-lobe fluid openings may have lobes that taper outward (e.g., width decreases away from the center of the opening) or inward (e.g., width decreases toward the center of the opening).

Figure 3D:
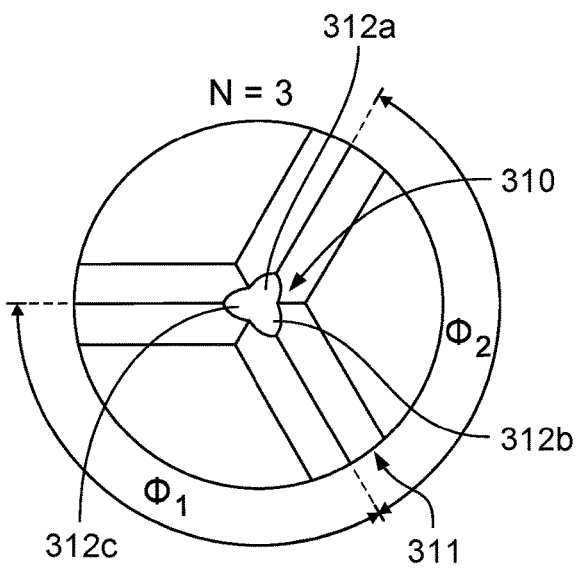
Figure 3E:
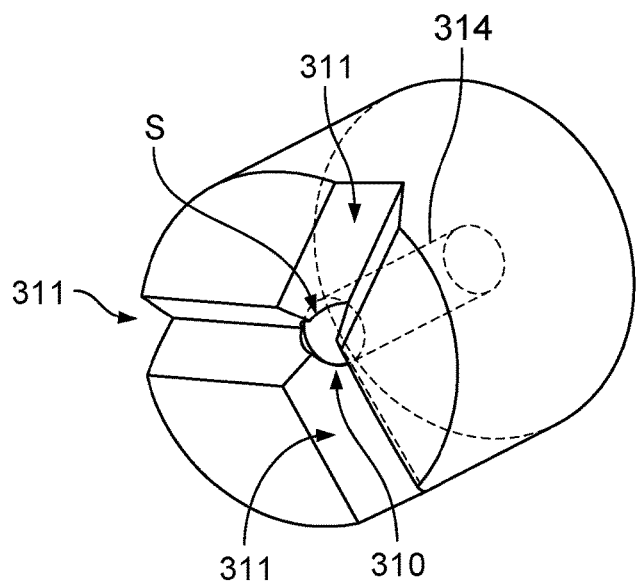

FIGS. 3C-3K depict variations of fluid openings with a three-lobed or tri-lobal shape. FIGS. 3C-3E depict one variation of a nozzle or fluid opening (310) having first, second, and third lobes (312a, 312b, 312c) that are arranged in a radially symmetric fashion (i.e., angular distribution is such that $\Phi_1$=120°, $\Phi_2$=120°). The fluid opening (310) may be at one end of a channel or lumen (314), which may have a length Lin and diameter d as described above. The three-lobed or tri-lobal shape may be referred to as a Y-shaped nozzle. In the variation of FIGS. 3C-3E, the Y-shaped nozzle may comprise three V-grooves (311) that create the three-lobed shape of the fluid opening and may also create a curved surface(S) disposed over at least a portion of the fluid opening (310). The Y-shaped nozzle may generate a tri-lobal, fan-like, sheet spray. Optionally, fluid may also flow along the channels or grooves created by the V-grooves. This may help the oral insert or mouthpiece to direct flow into the interproximal space and/or along the gingival margins, including subgingival regions, and more evenly distribute flow and shear stress coverage.

FIGS. 3F-3K depict other variations of a three-lobed or Y-shaped fluid opening or nozzle. FIGS. 3F-3G depict one variation of a fluid opening (316) that has three lobes similar to the opening (310), but with V-grooves (317) that are shorter than the V-grooves (311). The lobes of the fluid openings (310) and (316) may be wider than they are long. FIGS. 3H-3I depict one variation of a fluid opening (318) that has three lobes where the lobes (319) are longer than they are wide (e.g., lengths of the lobes may be from about 2 to about 6 times greater than the width). The fluid opening (318) may also be spaced apart from the inner channel (320) by a distance (a), where the distance (a) may be from about 0.25 mm to about 10 mm. The inner channel diameter may taper outward from the diameter (d) of the cylindrical portion (i.e., the diameter of the circumscribing circle containing the cross-section of the fluid path increasing along the distance (a)) such that the interior walls of the inner channel meet the tips of the lobes (319), for example, such that the channel leading up to the fluid opening is defined by a loft between the multi-lobed fluid opening and a circular cross section upstream of the fluid opening. In variations where the length between the tips of the fluid opening lobes is less than the diameter (d) of the inner channel (e.g., the largest dimension of the fluid opening is less than the diameter (d) of the inner channel), the diameter of the inner channel may taper inward from the diameter (d) of the cylindrical portion (i.e., the diameter of the circumscribing circle containing the cross-section of the fluid path decreasing along the distance (a)) such that the interior walls of the inner channel meet the tips of the lobes. FIGS. 3J-3K depict one variation of a fluid opening (322) that has three lobes where the lobes (323) are also longer than they are wide. The fluid opening (322) may also be spaced apart from the inner channel (324) by a distance (a), where the distance (a) may be from about 0.25 mm to about 10 mm. However, in contrast to the fluid opening (318), the end of the inner channel diameter (324) terminates with a shape that matches the shape of the fluid opening (322). The distance (a) between the Y-shaped cylindrical end portion (325) and the fluid opening (322) may be from about 0.25 mm to about 10 mm. In some variations, the fluid opening or nozzle (322) may be designed without any V-grooves, but instead may be designed by translating the fluid opening by a fixed distance up to the inner channel, which may be manufactured by extrusion methods. While certain design or manufacturing methods are described herein as examples of generating fluid openings with particular shapes, it should be understood that any design or manufacturing methods may be used as desired, e.g., extrusion techniques, any 3-D printing techniques, laser cutting techniques, and/or conventional machining (i.e., subtractive geometry creation) methods.

Figure 3L:
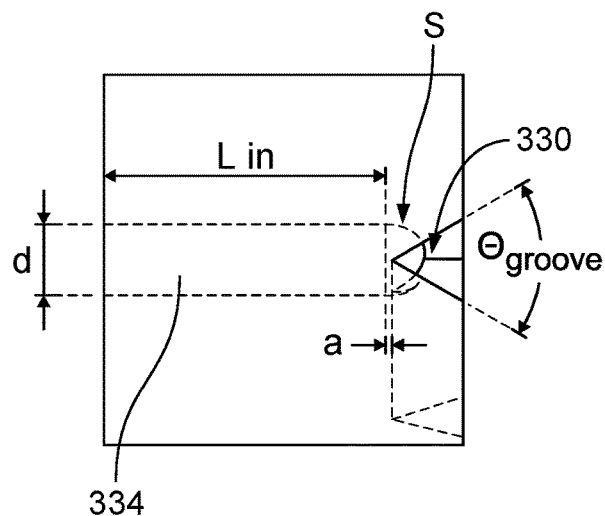
FIGS. 3L-3N depict a cross-sectional view, a front view, and a perspective view, respectively, of one variation of a two-lobed fluid nozzle or fluid opening.
Figure 3M:
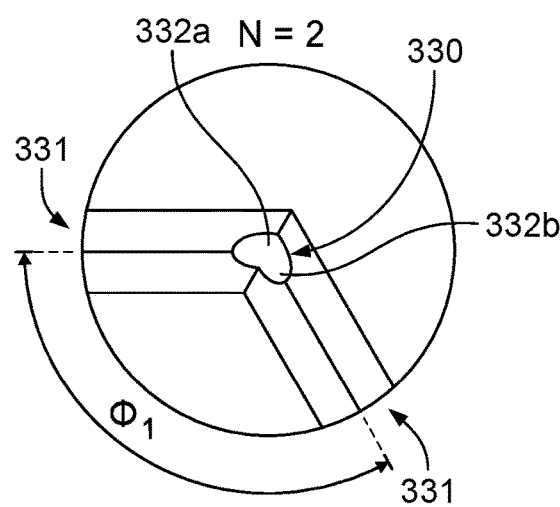
Figure 3N:
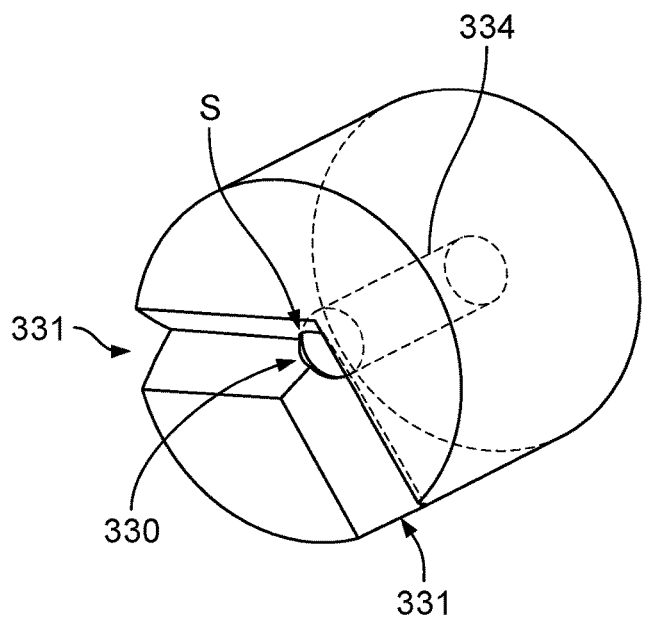

FIGS. 3L-3U depict variations of fluid openings with a two-lobed or bi-lobal shape. FIGS. 3L-3N depict one variation of a nozzle or fluid opening (330) having first and second lobes (332a, 332b) that are arranged in a bilaterally symmetric fashion (i.e., angular distribution is such that $\Phi_1=120°$). The fluid opening (330) may be at one end of a channel or lumen (334), which may have a length Lin and diameter d as described above. The two-lobed or bi-lobal shape may be referred to as a V-shaped nozzle. In the variation of FIGS. 3L-3N, the V-shaped nozzle may comprise two V-grooves (331) that create the two-lobed shape of the fluid opening and may also create a curved surface(S) disposed over at least a portion of the fluid opening (330). The V-flat nozzle contains two V-grooves, generating a bi-lobal fan sheet spray. This may help to direct fluid flow along the gingival margin and may help to increase shear stress coverage in the supragingival and subgingival regions, while still maintaining adequate or substantial coverage of the interproximal space. Optionally, fluid may also flow along the channels or grooves created by the V-grooves. The angle at which the V-shaped nozzles direct fluid to a user's oral anatomy may be specific to the oral anatomy of the user.

FIGS. 3O-3U depict other variations of a two-lobed or V-shaped fluid opening or nozzle. FIGS. 3O-3Q depict one variation of a fluid opening (336) that has two lobes similar to the opening (330), but with V-grooves (337) that are shorter than the V-grooves (331). The lobes of the fluid openings (330) and (336) may have widths that are similar to (or greater than) their lengths. FIGS. 3R-3S depict one variation of a fluid opening (338) that has two lobes where the lobes (339) are longer than they are wide (e.g., lengths of the lobes may be from about 2 to about 6 times greater than the width). The fluid opening (338) may also be spaced apart from the inner channel (340) by a distance (a), where the distance (a) may be from about 0.25 mm to about 10 mm. The inner channel diameter may taper outward from the diameter (d) of the cylindrical portion (i.e., the diameter of the circumscribing circle containing the cross-section of the fluid path increasing along the distance (a)) such that the interior walls of the inner channel meet the tips of the lobes (339), for example, such that the channel leading up to the fluid opening is defined by a loft between the multi-lobed fluid opening and a circular cross section upstream of the fluid opening. In variations where the length between the tips of the fluid opening lobes is less than the diameter (d) of the inner channel (e.g., the largest dimension of the fluid opening is less than the diameter of the inner channel), the diameter of the inner channel may taper inward from the diameter (d) of the cylindrical portion (i.e., the diameter of the circumscribing circle containing the cross-section of the fluid path decreasing along the distance (a)) such that the interior walls of the inner channel meets the tips of the lobes. FIGS. 3T-3U depict one variation of a fluid opening (342) that has two lobes where the lobes (343) are also longer than they are wide. The fluid opening (342) may also be spaced apart from the inner channel (344) by a distance (a), where the distance (a) may be from about 0.25 mm to about 10 mm. However, in contrast to the variation depicted in FIGS. 3R-3S, the end of the inner channel diameter (344) terminates with a shape that matches the shape of the fluid opening (342). The distance (a) between the V-shaped cylindrical end portion (345) and the fluid opening (342) may be from about 0.25 mm to about 10 mm. In some variations, the fluid opening or nozzle (342) may be designed without any V-grooves, but instead may be designed by translating the fluid opening by a fixed distance up to the inner channel, which may be manufactured by extrusion methods. While certain design or manufacturing methods are described herein as examples of generating fluid openings with a particular shape, it should be understood that any design or manufacturing methods may be used as desired, e.g., extrusion techniques, any 3-D printing techniques, and/or laser cutting techniques.

Figure 3V:
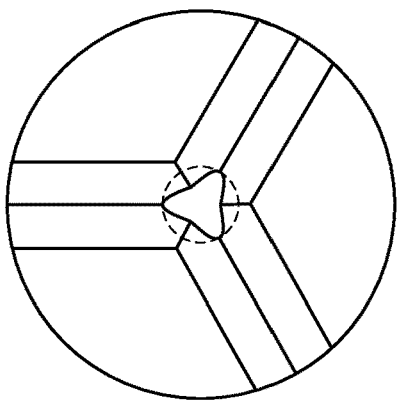
Figure 3W:
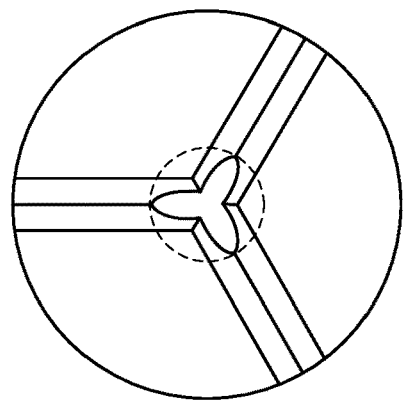
Figure 3X:
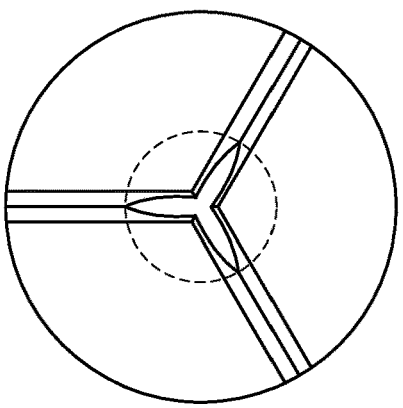
Figure 3Y:
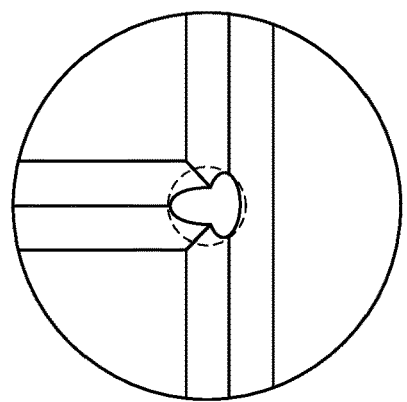
Figure 3Z:
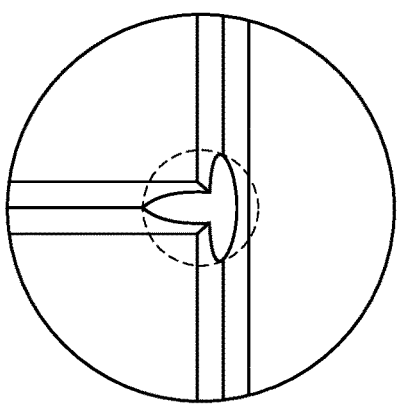
Figure 3A:
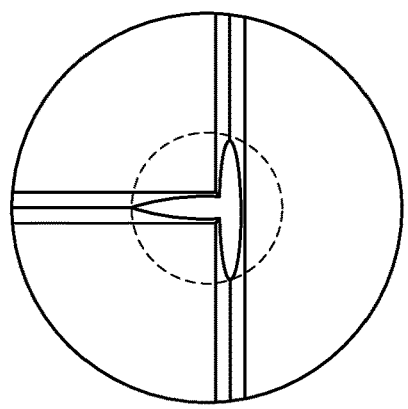

FIGS. 3V-3AA depict additional variations of fluid openings or nozzles having a three-lobe or tri-lobal shape, but with varying values for the angles $\Phi_{lobe}$, $\theta_{groove}$, and diameter (d). These variants may be selected from a design library and tuned to match an individual user's oral features, and/or may help to increase shear stress coverage across target regions or surfaces of the teeth. FIG. 3V depicts one variation of a fluid opening with three lobes that are radially symmetric and the widths of the lobes may be substantially constant as the lobes extend outward, and may have a curved lobe ending. FIG. 3W depicts one variation of a fluid opening with three lobes that are radially symmetric and the widths of the lobes may taper or narrow as the lobes extend outward, and may have a pointed lobe ending. The lengths of the lobes may be about 1.5 to about 2.5 times the widths of the lobes. FIG. 3X depicts one variation of a fluid opening with three lobes that are radially symmetric and the widths of the lobes may taper or narrow as the lobes extend outward, and may have a pointed lobe ending. The lengths of the lobes may be about 3 to about 5 times the widths of the lobes. FIG. 3Y depicts one variation of a fluid opening with three lobes where two of the lobes are about 180° from each other and the third lobe is about 90° from the other two lobes (e.g., forming a T-shape). The third lobe may have a length that is greater than or equal to the lengths of the first and second lobes. FIG. 3Z depicts one variation of a fluid opening with three lobes that are arranged similarly to the fluid opening in FIG. 3Y (i.e., T-shaped), however, the widths of the lobes may taper or narrow as the lobes extend outward, and may have a pointed lobe ending. The lengths of the lobes may be about 1.5 to about 2.5 times the widths of the lobes. FIG. 3AA depicts one variation of a fluid opening with three lobes that are arranged similarly to the fluid opening in FIG. 3Y (i.e., T-shaped), and the widths of the lobes may taper or narrow as the lobes extend outward, and may have a pointed lobe ending. The lengths of the lobes may be about 3 to about 5 times the widths of the lobes.

While the fluid openings or nozzles of FIGS. 3V-3AA are depicted as having V-grooves, it should be understood that in other variations, there may not be V-grooves. While certain design or manufacturing methods are described herein as examples of generating fluid openings with particular shapes, it should be understood that any design or manufacturing methods may be used as desired, e.g., extrusion techniques, any 3-D printing techniques, and/or laser cutting techniques.

Experimental Results

Figure 5A:
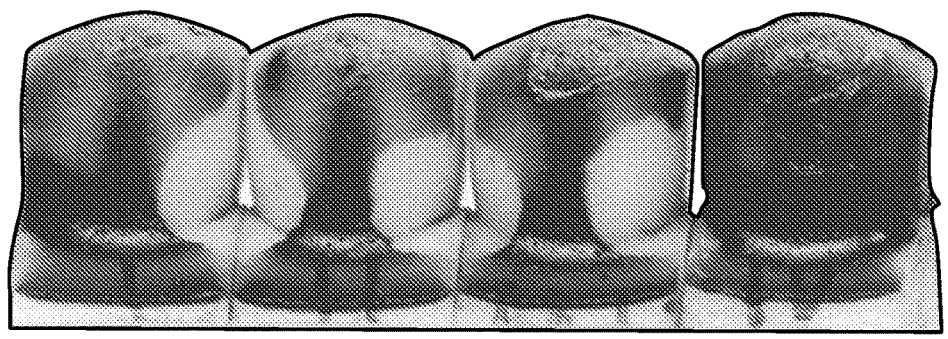
FIGS. 5A-5C depict the experimental and simulated cleaning results of a sample set of teeth using a Y-shaped fluid opening or nozzle.
Figure 5B:
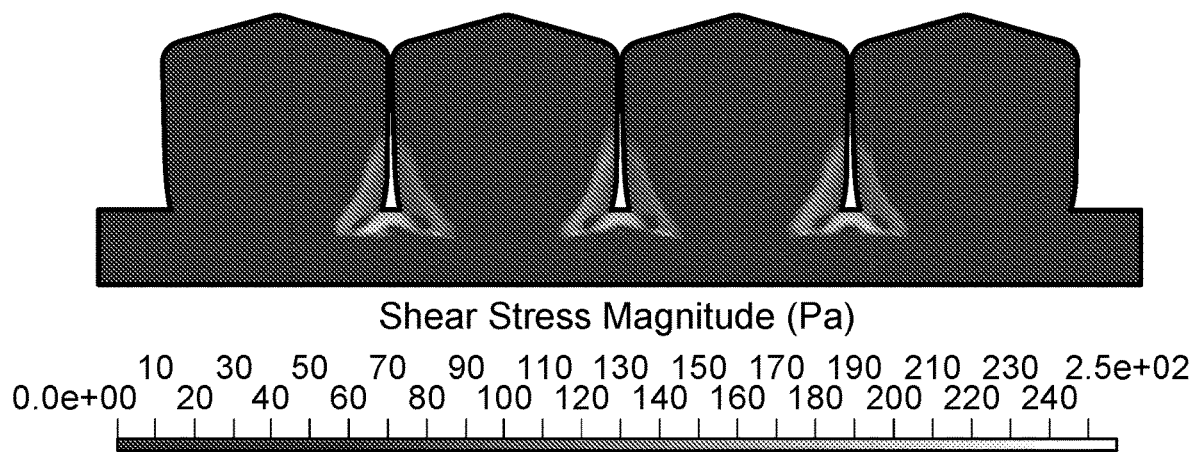
Figure 5C:
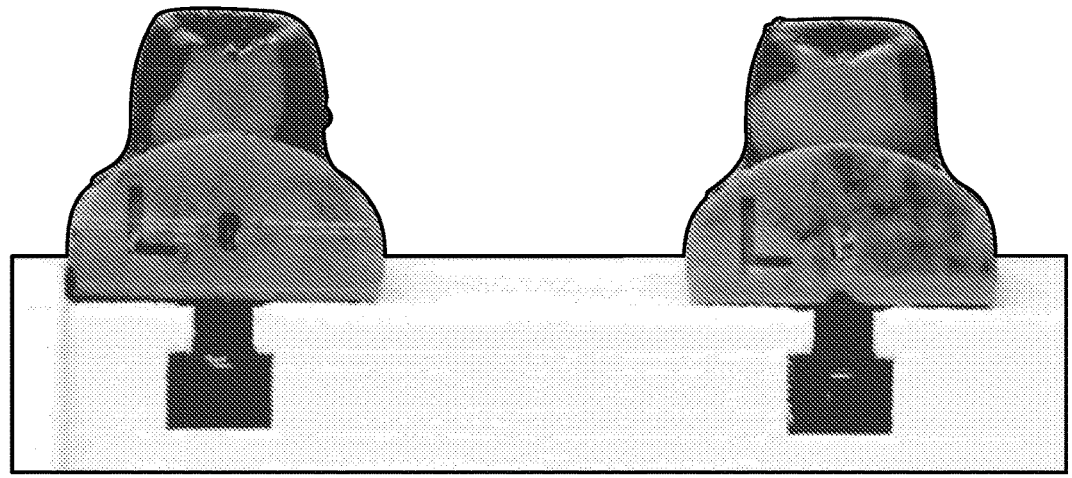

Experimental results have demonstrated that the fluid opening or nozzle shape affects and/or impacts the area that is cleaned. FIGS. 4A-4C depict the experimental and simulated cleaning results of a sample set of teeth using a circular or round-shaped fluid opening or nozzle, FIGS. 5A-5C depict the experimental and simulated cleaning results of a sample set of teeth using a Y-shaped fluid opening or nozzle (e.g., the fluid opening of FIGS. 3C-3E), and FIGS. 6A-6C depict the experimental and simulated cleaning results of a sample set of teeth using a V-shaped fluid opening or nozzle (e.g., the fluid opening of FIGS. 3L-3N). For each of the experiments for FIGS. 4A, 5A, 6A (front view) and 4C, 5C, 6C (side view, depicting the surface of the teeth along the interproximal space), a biofilm mimicking surrogate was applied over a set of four teeth models arranged in a row and fluid introduced to the teeth through a fluid opening or nozzle having a round shape, Y-shape, and V-shape. In all test cases, nozzles were positioned perpendicular to the long axis of the teeth. The average flow rate and time evaluated across nozzle designs were consistent for all experiments. FIGS. 4B, 5B, 6B are computational fluid dynamics (CFD) models of the fluid flow from openings or nozzles having a round shape, Y-shape, and V-shape, respectively, depicting the shear stress profiles or patterns from each of these nozzle shapes. The simulation employed the same nozzle geometry as the experiments. In the simulation, the nozzles were aligned (e.g., aimed) at the interproximal spaces of the four teeth to match the experiments. Simulation results were calculated using a finite volume method based steady-state incompressible flow solver. Momentum, pressure, and mass continuity solution residuals were reduced to below a normalized value of 1e-5 to ensure adequate numerical convergence. Material properties of pure water at 20° C. (room temperature) was assumed. Simulation nozzle inlet mass flow rates were set to the measured mass flow rates from the corresponding experiments above. Teeth, gum, and experimental apparatus surfaces were treated as no-slip, no-penetration walls with outlet surfaces surrounding the lower portion of the gum surfaces to allow for drainage of injected fluid. For turbulence modeling, the k-epsilon two equation model was used.

As may be seen in FIGS. 4A and 4C, a stationary, round nozzle may remove or clean the surrogate along the interproximal spaces, however, a round nozzle does not appear to clean the surrogate from the gingival margin, and also appears to clean little, if any, surrogate from the facial and lingual surfaces of the teeth. These experimental results are consistent with the simulation results depicted in FIG. 4B. In a customized oral insert or mouthpiece, round nozzles or fluid openings may be placed at locations that align with the interproximal spaces of a user's teeth. For example, an oral insert may comprise round nozzles or fluid openings that are aligned relative to the interproximal spaces of the teeth and located toward the top or occlusal surfaces of the teeth (as opposed to being located toward the bottom along the gingival margins).

As may be seen in FIGS. 5A and 5C, a stationary Y-shaped nozzle may remove or clean the surrogate along both the interproximal spaces and large portions of the facial and lingual surfaces, as well as regions along the gingival margin, however, a Y-shaped nozzles does not appear to clear the surrogate along the entire length of the gingival margin. These experimental results are consistent with the simulation results depicted in FIG. 5B. In a customized oral insert or mouthpiece, Y-shaped nozzles or fluid openings may be placed at locations that align with the interproximal spaces of a user's teeth. For example, an oral insert may comprise Y-shaped nozzles or fluid openings that are aligned relative to the interproximal spaces of the teeth and located toward the bottom along the gingival margins of the teeth (as opposed to being located toward the top toward the occlusal surfaces). The length of the lobes of a particular Y-shaped fluid opening for a particular tooth may be selected to approximate the height of the interproximal region and the length of gingival margins of that tooth and/or adjacent teeth. In some variations, the Y-shaped lobe may be oriented such that a first lobe may be oriented vertically along the vertical extent of an interproximal space between a first and second tooth, the second lobe may be oriented along the gingival margin of the first tooth, and the third lobe may be oriented along the gingival margin of the second tooth. The length of the second lobe may be about half the length of the gingival margin of the first tooth (and/or may approximate the entire length of the gingival margin of the first tooth) and the length of the third lobe may be about half the length of the gingival margin of the second tooth (and/or may approximate the entire length of the gingival margin of the second tooth). The length of the first lobe that may be aligned along a vertical extent (e.g., dimension parallel to the long axis of the tooth, or height) of an interproximal space may approximate the height of the interproximal space.

As may be seen in FIGS. 6A and 6C, a stationary V-shaped nozzle may remove or clean the surrogate along both the interproximal regions and the gingival margins. The V-shaped nozzle appears to clear more surrogate from the interproximal space than the Y-shaped nozzle, thereby effecting a "flossing" effect (i.e., cleaning the interproximal spaces and along the gingival margins). These experimental results are consistent with the simulation results depicted in FIG. 6B. In a customized oral insert or mouthpiece, V-shaped nozzles or fluid openings may be placed at locations that align with the interproximal spaces of a user's teeth. For example, an oral insert may comprise V-shaped nozzles or fluid openings that are aligned relative to the interproximal spaces of the teeth and the interdental gingiva and located toward the bottom along the gingival margins of the teeth (as opposed to being located toward the top toward the occlusal surfaces). The length of the lobes of a particular V-shaped fluid opening for a particular tooth may be selected to approximate the length of gingival margins of that tooth and/or adjacent teeth, and may approximate the geometry of the interdental gingiva. In some variations, the V-shaped lobe may be oriented such that a first lobe may be oriented along the gingival margin of a first tooth and the second lobe may be oriented along the gingival margin of a second tooth adjacent to the first tooth. The length of the jet generated by the second lobe may be about half the length of the gingival margin of the first tooth (and/or may approximate the entire length of the gingival margin of the first tooth) and the length of the jet generated by the third lobe may be about half the length of the gingival margin of the second tooth (and/or may approximate the entire length of the gingival margin of the second tooth).

An oral insert or mouthpiece may comprise one or more fluid openings or nozzles with a variety of shapes to address and clean different areas of the teeth. That is, different nozzle shapes may be combined on an oral insert to achieve both "flossing" effects and "brushing" effects (i.e., to floss, brush, or otherwise clean the facial, lingual, mesial, distal, and occlusal surfaces and the incisal edges). For example, an oral insert may comprise a plurality of V-shaped nozzles or Y-shaped nozzles aligned relative to the interproximal spaces and/or along the gingival margins/interdental gingiva to facilitate a flossing effect, and a plurality of round nozzles aligned relative to the facial and/or lingual surfaces of teeth to facilitate a brushing effect. Y-shaped and/or V-shaped nozzles may also be aligned relative to the facial and/or lingual surfaces of teeth. Alternatively, a plurality of round nozzles may be aligned relative to an interproximal space but located toward the top or occlusal surfaces of the teeth, while a plurality of V-shaped and/or Y-shaped nozzles may be aligned relative to the interproximal space but located toward bottom or gingival margins of the teeth. In some variations, all (or nearly all) of the fluid openings or nozzles of a mouthpiece may be the same one type to facilitate a single function (e.g., a mouthpiece with all V-shaped nozzles or Y-shaped nozzles may be a flossing mouthpiece, a mouthpiece with all rounded nozzles may be a brushing mouthpiece). A system may comprise a first "flossing" mouthpiece (e.g., with nearly V-shaped and/or Y-shaped nozzles) and a second "brushing" mouthpiece (e.g., with nearly all round nozzles). Any combination of any of the nozzles or fluid openings described herein may be combined with any number of oral inserts or mouthpieces (e.g., in the same or different troughs of a mouthpiece, etc.), as may be desirable.

Manifold Customization

Figure 7A:
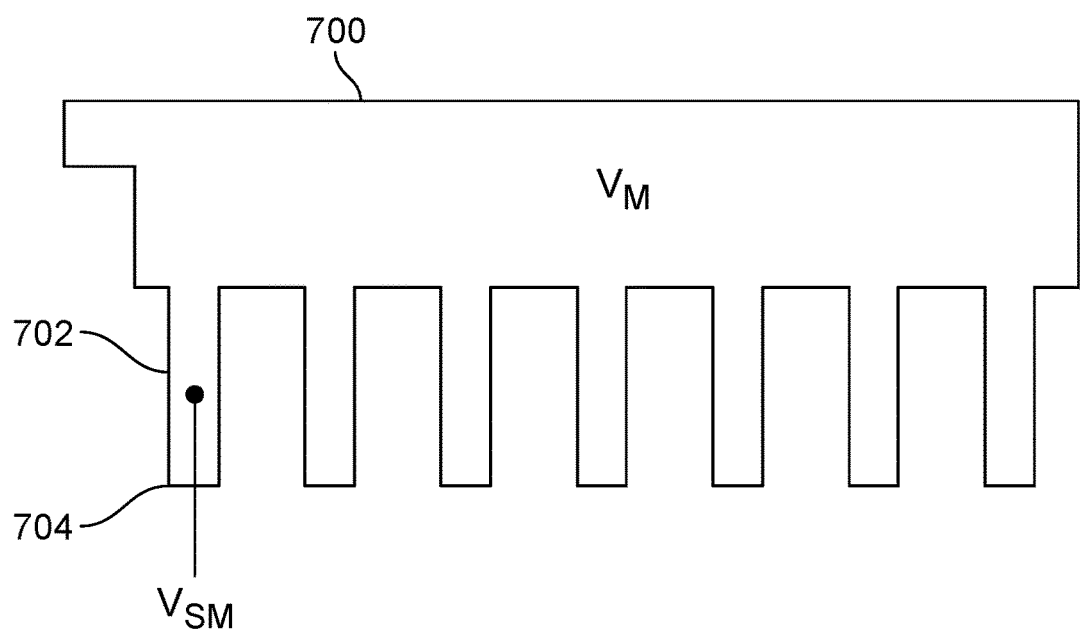
FIGS. 7A-7B are schematic depictions of variations of manifold configurations.
Figure 7B:
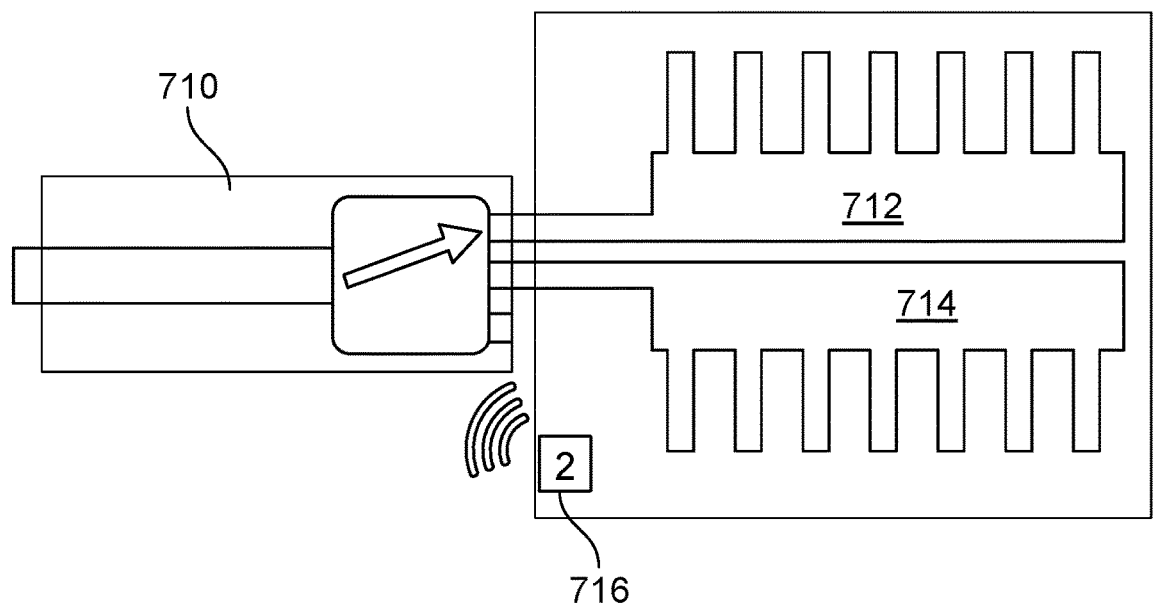

As described above, an oral insert or mouthpiece may comprise one or more manifolds in fluid connection with the plurality of fluid openings or nozzles. FIGS. 7A-7B are schematic depictions of one variation of a manifold arrangement that may be used with any of the oral irrigation systems described herein. An individual manifold may regulate fluid flow to a set of nozzles, and may adjust the fluid flow to those nozzles separately from the fluid flow to a different set of nozzles (which may be connected to a different manifold). In some variations, the one or more manifolds of a mouthpiece may be connected to a single fluid inlet (e.g., via a conduit from the handle or base station reservoir). Manifolds may facilitate fluid ingress or egress, as may be desirable. A manifold may have several parameters that can be tuned to control the fluid velocity at each nozzle, including, but not limited to a volume of main manifold (700) ($V_M$) and/or a volume of each sub-manifold (702) ($V_{SM}$) that feeds a nozzle (704). One or more nozzles may be configured to release fluid into the oral cavity should the pressure in the manifold exceed a threshold fluid pressure. These release nozzles may have larger apertures than the non-release nozzles and may be placed such that they simply irrigate the oral cavity while relieving excess manifold pressure. The parameters of the main manifold (700) and/or the sub-manifolds (702) may be selected by iterating through different values and simulating the fluid flow through the manifolds and the nozzles until a desired flow rate, flow profile, or shear stress distribution is attained. In some variations, evolutionary algorithms (e.g., machine learning or artificial intelligence) may be used to permute and simulate the manifold and nozzle geometry to arrive at a set of manifold and nozzle parameters and geometries that meet the desired fluid flow characteristics.

Figure 15:
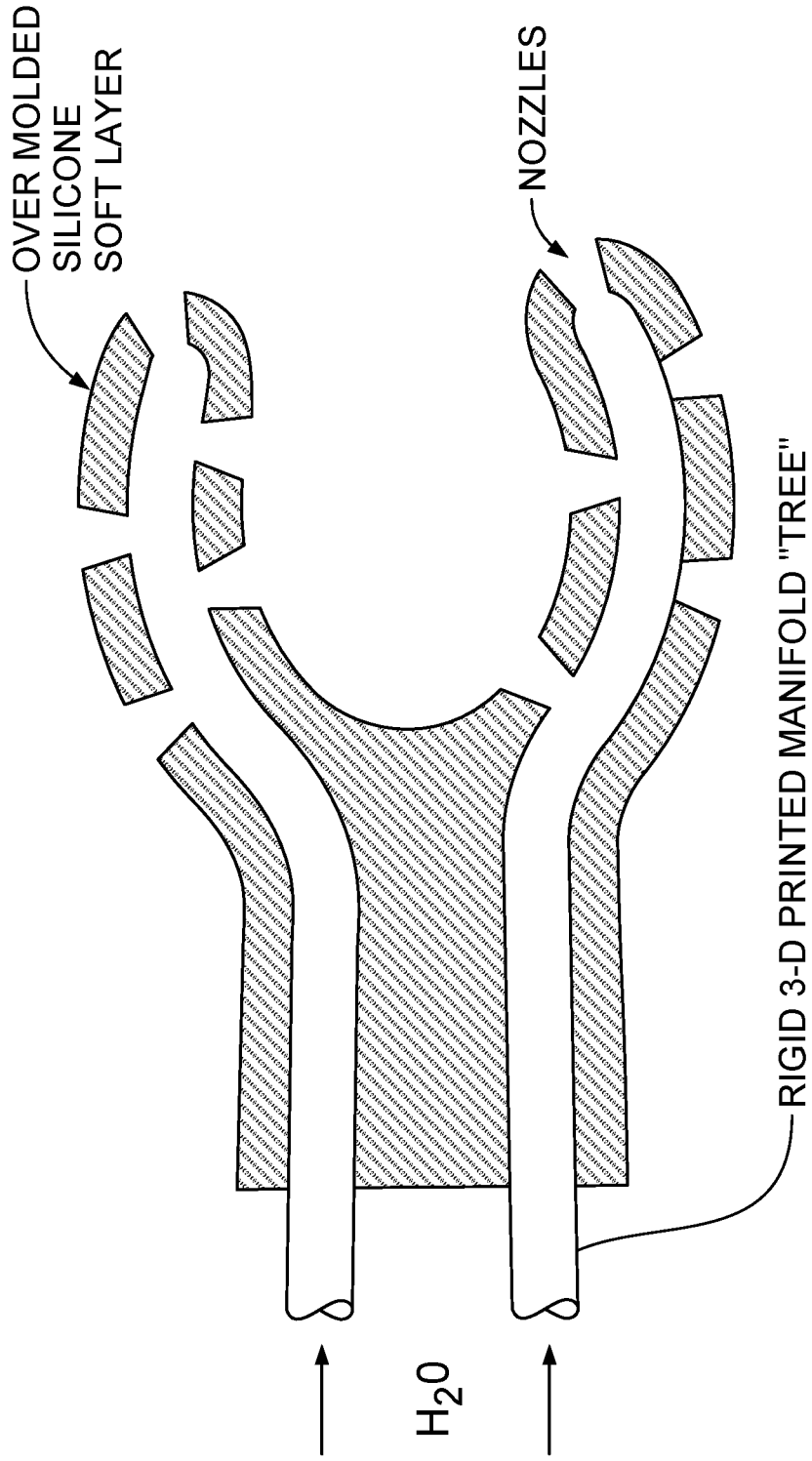
FIG. 15 depicts manifolds including nozzles that are 3D printed within an oral insert and then over molded with a layer in accordance with some embodiments.

In some embodiments, as seen in FIG. 15, the manifolds including the nozzles are 3D printed within an oral insert and then over molded with a layer, e.g., medical grade Silicone, for softness in the mouth.

Manifold Count Customization

In some variations, fluid openings or nozzles may be distributed across a customizable number of manifolds within an oral insert or mouthpiece in order to accommodate differently-sized mouths and to manage the amount of fluid flowing into the mouth simultaneously. In some variations, a base station (710) may direct fluid into each manifold (712) and (714) in phases during the cleaning cycle. A customized mouthpiece may comprise, for example, an embedded RFID chip (716), or any similar identification technology, that communicates, to the base station, the number of manifolds present in the mouthpiece. This may allow the base station (710) to only direct fluid to existing manifolds. The base station may direct a constant or pulsing (e.g., from about 1 Hz to about 25 Hz), but user-adjustable, flow into each manifold of the mouthpiece. For example, control buttons on the handle and/or base station may allow a user to adjust the fluid pressure to a comfortable level. Fluid pressure may also be reduced for pediatric mouthpieces, or for those with orthodontic appliances. The RFID chip in the mouthpiece may store patient-specific data that may be transmitted to a RFID reader in the base station, and optionally, the base station may recommend a fluid flow mode based on patient-specific data (e.g., age, size, preferred fluid flow parameters, compliance metrics, etc.). In some variations, the base station may automatically adjust fluid pressure depending on the size of the person's mouth, the number of manifolds in their unique mouthpiece, size and shapes of the manifolds, and the like.

Multi-Reservoir and/or Multi-Manifold Variations

Figure 8A:
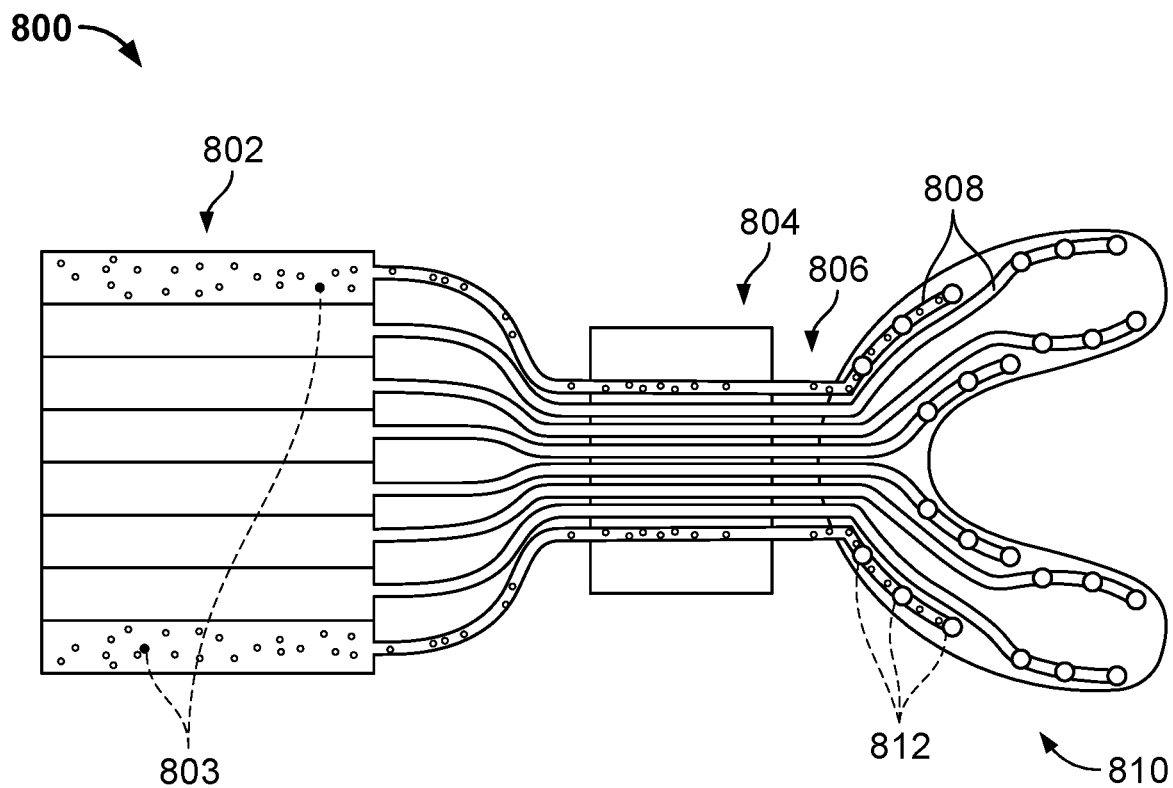
FIGS. 8A-8B are schematic depictions of variations of manifold and fluid reservoir configurations.

Some oral irrigation systems may comprise multiple fluid reservoirs and a multi-piston pump to independently control the flow of fluid from each of the fluid reservoirs through their respective manifolds. In this variation, additives may be included in some reservoirs for infusion to certain regions of the oral cavity while limiting exposure of those additives to other regions of the oral cavity. FIG. 8A depicts one variation of a system (800) comprising a plurality of separate fluid reservoirs (802), a multi-piston pump (804) that has separate fluid conduits (806) that are each in communication with a separate fluid reservoir, and a plurality of manifolds (808) in the mouthpiece (810) that are each in communication with a corresponding fluid conduit (806). Each manifold (808) may provide fluid to a plurality of fluid openings or nozzles (812). The use of multiple reservoirs with a multi-piston pump may facilitate the delivery of customized additives to each independent mouthpiece manifold. For example, additives (803) introduced into a subset of reservoirs (802) may be introduced only in the corresponding subset of manifolds (808) and fluid openings (812).

Figure 8B:
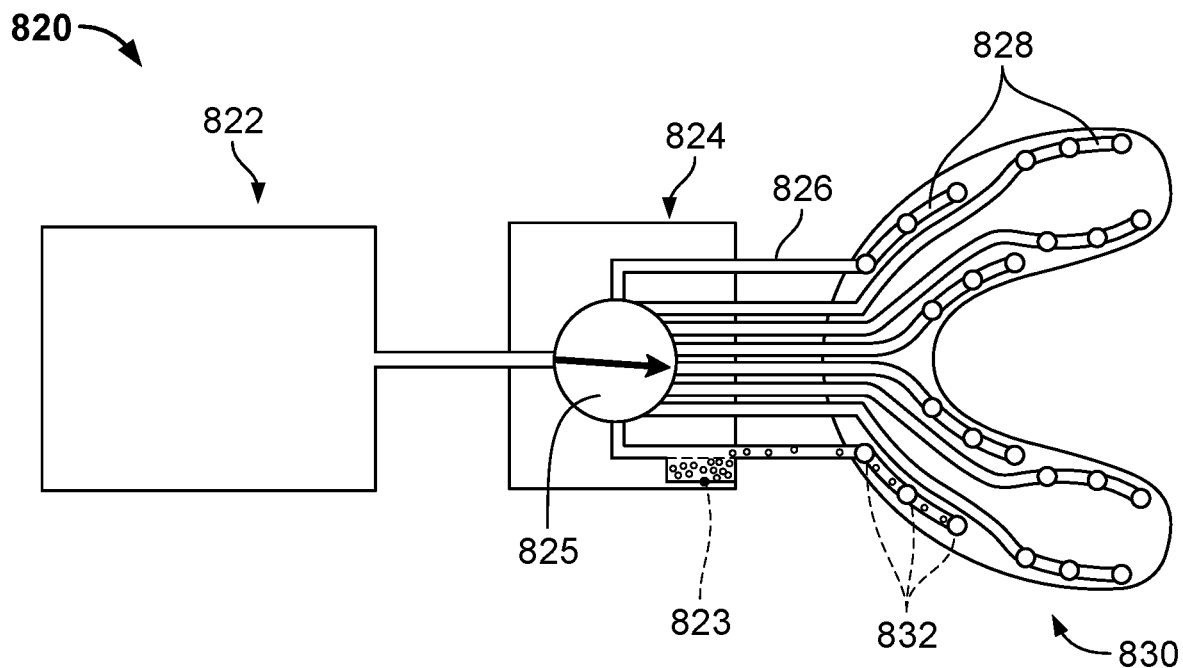

Alternatively or additionally, some systems may comprise a single fluid reservoir and a single-piston pump. In-line injections of additives to certain fluid conduits in the pump with a manifold-switch design may facilitate delivery of additives to one manifold and not another. For example, as depicted in FIG. 8B, a system (820) may comprise a single fluid reservoir (822) and a pump (824) that has a switching manifold (825) that alternates connectivity between the fluid reservoir and the separate fluid conduits (826) that are in communication with separate manifolds (828) of a mouthpiece (830) having a plurality of fluid openings or nozzles (832). An additive may be introduced to an individual manifold (828) via a cartridge (823) inserted into the desired manifold in the mouthpiece or handle. This cartridge may last multiple uses (e.g., the entire lifetime of the mouthpiece, one or more months, three months, etc.), and may facilitate a slow, controlled delivery of the additive. This may be achieved using the Venturi effect, in conjunction with a check valve, and/or via diffusion through a permeable membrane, and/or erosion of a solid additive.

The ability to direct therapeutic flow to specific areas of the mouth may provide an additional opportunity for user-specific customization. These customization settings may be provided to the device via software updates provided wirelessly, via a wired connection, or could be provided in non-volatile electronic memory (e.g., ROM, EEPROM, OTPROM, or similar) located within the periodically-replaceable mouthpiece. If located in a memory device in the mouthpiece, the information may be transmitted to the device via electrical contacts, RF or optical signals, or a similar method. This user-specific information may also be provided to the device via the reading of non-electronic storage means, for example, a QR code, bar code, or other similar means.

Manifold Operation

Figure 9A:
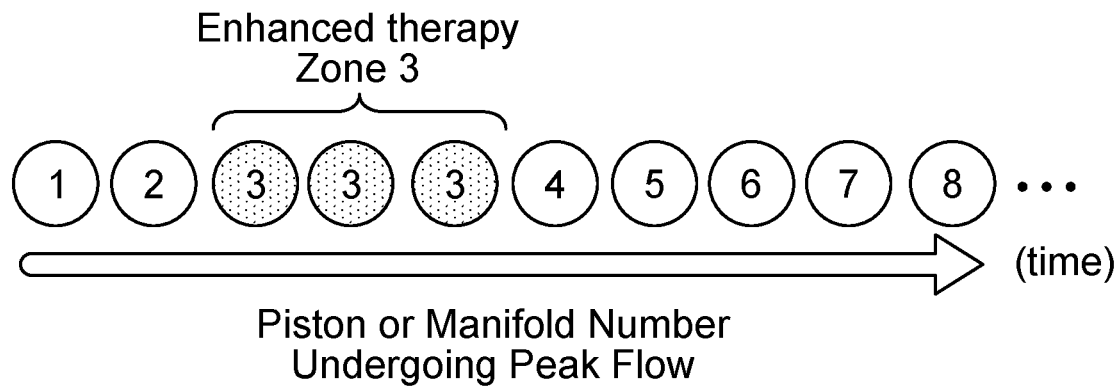
FIGS. 9A-9B are schematic depictions of manifold control methods.
Figure 9B:
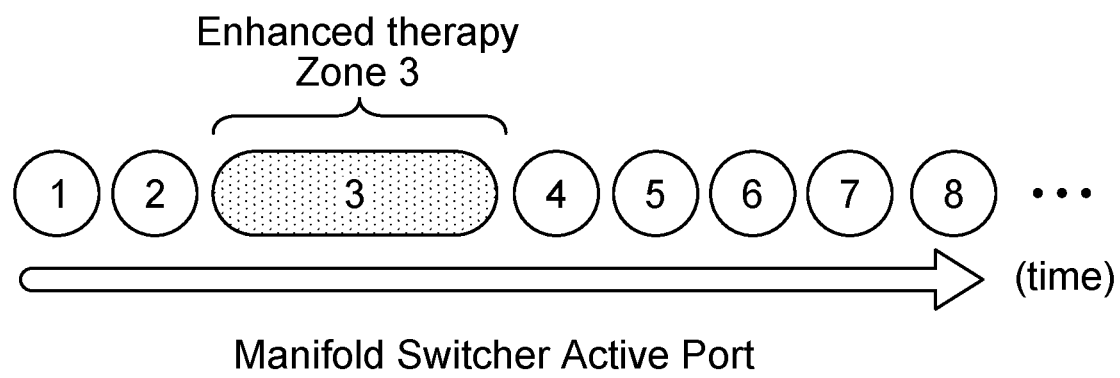

FIG. 9A is a schematic representation of one example of a method for controlling a manifold to provide oral irrigation with any of the systems described herein. As an example, an 8-piston pump may deliver fluid flow to 8 independent manifolds (which may in turn connect to one or more associated nozzles) that could be controlled in such a way as to deliver additional flow to a specific tooth, or group of teeth. One piston may be fired repeatedly several times in a row to deliver additional flow to a manifold before continuing to fire the rest of the pistons. Some variations may comprise multiple, separate, single-piston pumps, each connected to a different manifold, and increased flow to one portion of the oral cavity (e.g., the portion of the oral cavity corresponding to the fluid openings or nozzles associated with manifold 3) may be attained by driving one piston pump faster than the rest. Alternatively or additionally, a single-piston pump (or any type of pump) may be used in conjunction with a multi-channel manifold switcher (e.g., as described above in FIG. 8B), where the switcher may be programmed to "dwell" longer on a particular fluid conduit or manifold. This may direct additional flow to a specific manifold, to the corresponding set of nozzles to provide irrigation to a specific tooth or set of teeth (e.g., to deliver enhanced therapy to that tooth or teeth). For example, the manifold switcher in its baseline state may be programmed to direct one cycle of the piston pump to each manifold. To provide enhanced therapy to a particular region of the oral cavity, the manifold switcher may be programmed to pause on one manifold (i.e., provide fluid communication from the reservoir to a particular conduit or manifold) for more than one cycle of the piston pump before continuing to cycle through the remainder of the manifolds.

Methods

FIG. 10 depicts one variation of a method for creating a custom oral insert or mouthpiece comprising an arrangement or pattern of fluid openings that are tuned to the unique geometry of a user's mouth. Method (500) may comprise obtaining (502) oral structure data comprising the size, shape, and location of a user's teeth and gums. Obtaining oral structure data may comprise acquiring optical and/or digital impressions using intraoral scanners or photographs (e.g., 3-D intraoral scans, 3-D scans of a dental impression), photographs, X-rays, physical impressions, intraoral and extraoral radiographs, computed tomography, including cone beam computed tomography, magnetic resonance imaging, ultrasound, and the like. These measurements may be taken across the surface(s) of each tooth (e.g., lingual, facial, occlusal surfaces), in the interproximal regions, and spanning the gingival margin, including about 10 mm of the gingiva. The measurements may be accurate to within 0.25 mm.

Method (500) may then comprise identifying teeth surfaces (e.g., lingual, facial, occlusal surfaces), gingival margins, and/or interproximal features. For example, method (500) may comprise calculating (504) an oral surface map that identifies locations of gingival margins (510), interproximal spaces (512), incisal edges (513), and contours of the occlusal, facial, lingual, mesial and distal of the teeth (for example, in FIG. 10, facial surfaces are indicated with a circular dot (514)).

Method (500) may then comprise generating (506) an arrangement of fluid openings in the trough(s) of the oral insert. The location of fluid openings in the trough(s) (i.e., top and bottom troughs, right and left troughs, etc.) may correspond to the location of the gingival margins, interdental gingiva, interproximal regions, incisal edges, and contours of the occlusal, facial, lingual, mesial and distal surfaces of the teeth. The openings or nozzles may be located and/or oriented as described above. For example, each surface, gingival margin, and interproximal feature may be identified in the model (in step (504)) and one or more nozzles may be placed in a trough of the mouthpiece with any orientation, distance and nozzle shape, as described above, to provide adequate shear stress distribution across the feature. Fluid openings or nozzles may be located along the side walls and/or bottom wall of the mouthpiece trough. In some variations, fluid openings or nozzles disposed along the side walls may be positioned to apply fluid flow to facial and/or lingual surfaces and/or interproximal spaces and/or gingiva, while the fluid openings or nozzles located along the bottom wall may be positioned to apply fluid flow to the occlusal surfaces and/or incisal edges of the teeth. Fluid openings or nozzles on the bottom wall of the trough may face the occlusal surface and/or incisal edge of a tooth, and may be angled with respect to the long axis of the tooth, e.g., from about 0° to about 30°, from about 35° to about 55°, from about 45° to about 90°, about 45°, etc. Nozzles may have a maximum coverage area and if a dental feature is determined to be too large for the maximum fluid coverage area attainable by a single nozzle, multiple nozzles can be placed for that dental feature to provide complete fluid coverage. In some variations, V-shaped and/or Y-shaped fluid openings or nozzles may be located on the mouthpiece such that they align with the identified interproximal spaces (512), and/or interdental gingiva (515), and may be located toward the bottom of the teeth, along the gingival margins (510). The diameter of the inner fluid channel, groove angle, and the dimensions and shape of the fluid openings or nozzles may be adjusted to correspond with the geometry and positioning of interproximal spaces, teeth surfaces, and/or gingiva. For example, multiple V-shaped and/or Y-shaped nozzles may be disposed along the length of a gingival margin if the spread or width of fluids from a single nozzle is insufficient to cover the entire length of the gingival margin. For taller crowns, round nozzles may be aligned relative to the identified interproximal spaces (512), but toward the top surfaces (e.g., occlusal surfaces and/or incisal edges) of the teeth in order to extend the coverage achieved by the V-shaped and/or Y-shaped nozzles. The diameter of the round nozzle and/or the lengths, widths, angular distribution, and/or rotational orientation of a multi-lobe shaped nozzle may be selected based on the dimensions of the lengths, heights, widths, and curvature of the gingival margins, interproximal spaces, facial and/or lingual surfaces, and/or occlusal and/or incisal surfaces. In some variations, the largest dimension of a fluid opening (e.g., diameter for a round opening, distance between opposing lobe tips for a multi-lobular opening, etc.) may be selected to approximate or correspond to the width of the interproximal space along the gingival margin and/or interdental gingiva. A dimension of the fluid opening or nozzle (e.g., width, length, diameter) may be selected to approximate or correspond with the length and/or curvature of the gingival margin of a tooth. For example, in some variations, the method (500) may comprise calculating an average length and/or radius of curvature (ROC) of all of the gingival margins of a user's teeth, and this average length or ROC may be used to size the Y-shaped or V-shaped lobes such that the resulting jets span approximately half the average length of the gingival margins. For example, individual teeth having gingival margins that have lengths that are greater than one standard deviation from the average gingival margin length could have their corresponding nozzle dimensions or shapes adjusted to accommodate the unique or individual length of their gingival margin. Alternatively or additionally, a customized oral insert or mouthpiece may comprise fluid openings or nozzles that have a multi-lobe structure, where the arrangement of the lobes is selected to align with the grooves on the occlusal surfaces of the teeth. In some variations, the position and/or orientation of fluid openings or nozzles may be determined by the volume of the oral cavity in the proximity of the target tooth or teeth. That is, for regions of the oral cavity where the user's cheeks, tongue, and/or other oral anatomical structures constrain the space around the tooth or teeth, fluid openings or nozzles have a limited range of angular orientations. For example, for regions of the oral cavity where the distance between the surface of a teeth and the cheek, tongue, or other oral structure is less than or equal to about 7 mm, the nozzles may be positioned at an angle from about 0 degrees to 35 degrees from the long axis of a tooth. For regions of the oral cavity where the distance between the surface of a tooth and the cheek is more than about 7 mm, the nozzles may be positioned at an angle from about 0 degrees to about 90 degrees, e.g., from about 40 degrees to about 80 degrees, about 45 degrees, about 60 degrees, etc.

In addition to anatomical data of the oral cavity, user input may also be used in the customization of the oral insert. For example, the user may indicate areas of tooth or gum sensitivity, and the oral insert may comprise fluid openings or nozzles in the corresponding area that provide indirect fluid flow, and/or less shear stress to those teeth. A fluid opening shape that provides more diffuse fluid irrigation may be positioned in the oral insert at regions that overlay the sensitive teeth or gums. For example, the oral insert may have fluid openings with larger diameters or dimensions to reduce the fluid pressure to those areas, and/or may have fewer fluid openings in those areas. Optionally, the user may also indicate areas where food debris tends to accumulate (e.g., perhaps due to user preferred chewing motions or patterns), and an oral insert may comprise fluid openings or nozzles that particularly target and direct fluid of higher pressure to increase the shear stress applied to those areas. For example, multiple fluid openings may be oriented and angled at one area (e.g., an interproximal space that is particularly large or prone to accumulate debris) to flush that area from multiple angles with a greater cumulative pressure or shear stress coverage than may be applied by a single fluid opening.

Optionally, a customized mouthpiece design may be evaluated to identify any design errors. In some variations, a verification check may comprise a manual or automated Design Rules Check (DRC) to ensure that all mouthpiece features meet a predetermined set of rules or criteria. One example of a rule check may comprise ensuring that no walls are too thin for the mouthpiece material. A more advanced check may include a manual or automated Finite Element Analysis (FEA) of the mouthpiece design. The customized mouthpiece design may also be verified to evaluate efficacy of biofilm and/or debris removal. A manual or automated Computational Fluid Dynamics (CFD) simulation can be run to ensure that each fluid nozzle produces the desired fluid velocity and coverage. If this simulation shows areas where the desired fluid velocity and coverage have not been achieved, the corresponding nozzles can be adjusted and the simulation re-run. This iterative cycle could be manual or automated with software.

Figure 11:
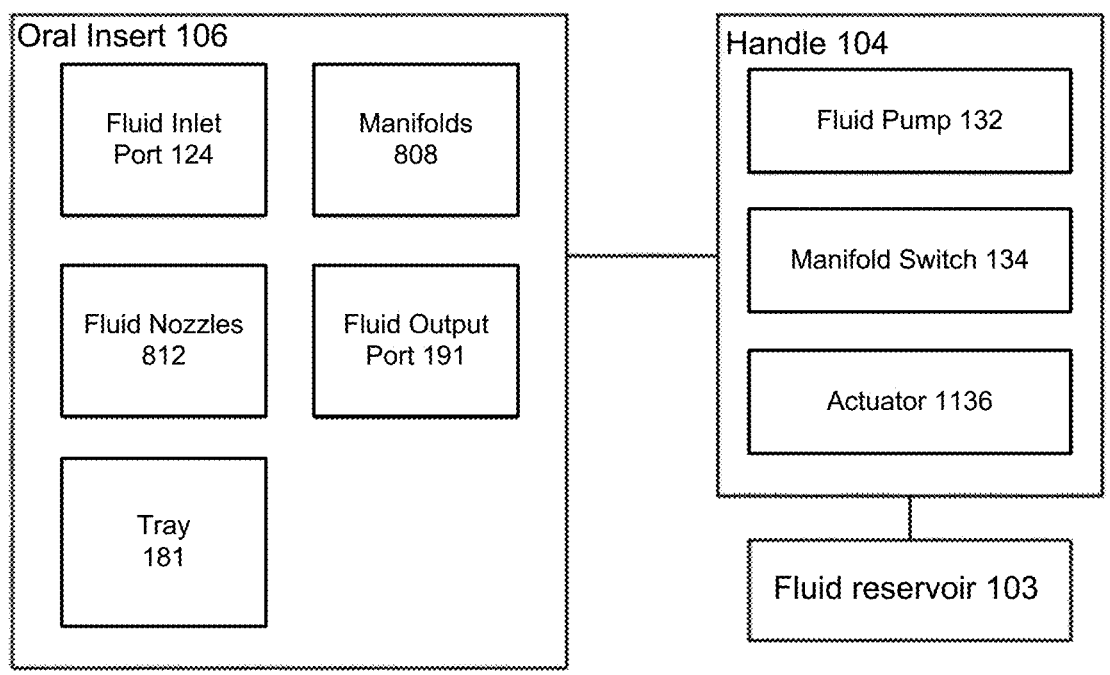
FIG. 11 depicts a block diagram of an oral care system (1100) in accordance with some embodiments.

FIG. 11 depicts a block diagram of an oral care system (1100) in accordance with some embodiments. In the example shown, oral care system (1100) comprises an oral insert (106), handle (104), and fluid reservoir (103). The oral insert (106) may be releasably engaged with the handle (104) and fluid reservoir (103). A user may use the handle (104) to manipulate and position the oral insert (106) within the oral anatomy. The oral insert (106) may be configured to be in fluid communication with the fluid reservoir (103). The oral insert (106) may output a predetermined volume of fluid received from the fluid reservoir (103). The fluid structures defined by the oral insert (106) may comprise a fluid inlet port (124), a set of manifolds (808), a set of nozzles (812), and a fluid outlet port (e.g., effluence port) (191). The oral insert (106) may define a tray (181) configured to retain teeth (e.g., upper teeth, lower teeth). In some variations, the tray (181) may be configured such that at least a portion of the tray (181) corresponds to a shape of the user's teeth.

The oral insert (106) may be configured to receive fluid from the fluid reservoir (103) at the fluid inlet port (124). The fluid inlet port (124) may be configured to be in fluid communication with the set of manifolds (808) and the set of nozzles (812). In one embodiment, the oral insert (106) includes a set of 8 manifolds where each manifold includes 8 nozzles. Fluid output from the set of nozzles (812) may be directed at the user's oral anatomy, for example, through the interproximal spaces between the teeth. A nozzle may be positioned at any location on a manifold. However, the nozzle position is specific to the oral structure of a user. After the fluid passes through and/or irrigates the user's oral anatomy, the fluid may then be guided to the fluid outlet port (191) to exit the user's oral cavity. In some variations, fluid may flow sequentially into the fluid inlet (124) and through the set of manifolds (808) and then the respective nozzles (812). The set of nozzles (812) may be configured to output fluid toward oral anatomy. The fluid outlet port (191) may then receive the fluid (e.g., effluence) and channel it away from the oral anatomy.

In some variations, the oral insert (106) may be configured to receive fluid from the handle (104) and/or fluid reservoir (103). In some variations, the handle (104) may comprise one or more of a fluid pump (132), manifold switch (134), and actuator (1136). For example, the fluid inlet port (124) may be coupled to the fluid pump (132). The fluid pump (132) may be configured to output pressurized fluid to the oral insert (106). The fluid pump (132) is configured to output pressurized fluid such that a flow rate of the pressurized fluid at each of the fluid nozzles (812) is the same flow rate within a predetermined tolerance. The fluid pump (132) is configured to provide a particular flow rate of fluid having a particular amount of pressure. In some variations, the handle (104) may comprise a manifold switch (134) configured to select and route fluid into one or more of the manifolds (808). For example, the manifold switch (134) may be configured to output fluid sequentially to each manifold at a predetermined rate. This may allow control of fluid flow rates to increase user comfort by preventing an excess volume of pressurized fluid from entering and exiting a user's mouth. In some embodiments, manifold switch (134) is configured to sequentially output fluid in an overlapping manner where fluid is continually provided to at least two of the manifolds (808) when switching between the manifolds (808). For example, at t1, manifold switch (134) may be configured to output fluid to a first manifold. At t2, manifold switch (134) may be configured to output a first portion of the fluid to the first manifold and a second portion of the fluid to a second manifold. At t3, manifold switch (134) may be configured to output the fluid to the second manifold. This prevents the fluid pump (132) from entering a deadhead state. Manifold switch (134) is configured to switch between the manifolds (808) at a rate that prevents user discomfort when oral insert 106 is inserted in the user's mouth and pressurized fluid is being directed to the user's oral anatomy. In some embodiments, the switching rate is between 8 Hz and 30 Hz. A switching rate below 8 Hz (e.g., 2 Hz-4 Hz) may cause the user's head to shake when using oral care system (1100). A switching rate above 30 Hz may generate a buzzing sound that some users may consider to be objectionable. In some embodiments, manifold switch (134) is comprised of mechanical channels that are driven by an electric motor (not shown). In some embodiments, manifold switch (134) is a fluid-flow driven turbine. Manifold switch (134) is configured to provide a pulsatile flow of fluid received from fluid reservoir (103). The handle (104) may comprise an actuator (1136) configured to operate one or more of the fluid pump (132) and manifold switch (134).

In some variations, the fluid reservoir (103) may be configured to hold a predetermined volume of fluid. For example, the fluid reservoir (103) may be configured to hold enough fluid for at least one cleaning cycle. Additionally or alternatively, the fluid reservoir (103) may be configured to couple to a fluid source to supply and/or augment the fluid held by the fluid reservoir (103).

Additionally or alternatively, the oral care system (1100) may comprise one or more temperature control elements (e.g., heater, chiller). For example, one or more of the handle (104) and fluid reservoir (103) may comprise one or more of a heating element and a cooling element. In some variations, a heating element may be configured to control a temperature of the fluid. In some variations, the fluid may be set at a predetermined range of temperatures to improve cleaning efficacy (e.g., higher temperatures may help facilitate removal of hydrophobic food or biofilm residues, such as residues with fatty acids and/or oils, and/or dissolve and/or soften hardened food residues), and/or increase chemical activity of entrained, therapeutic additives. In some variations, a heating element may comprise an electrical-resistance type heating element, and/or a cooling element may be a thermoelectric cooler (e.g., a solid-state device such as a Peltier device).

Figure 12A:
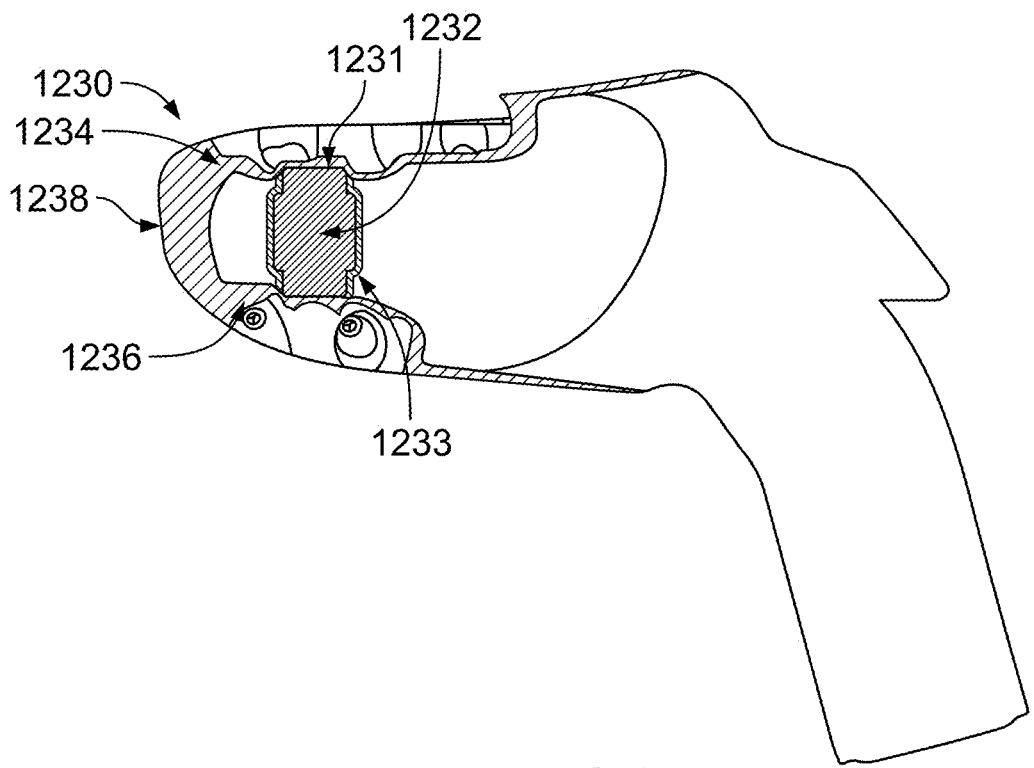
FIG. 12A depicts a cross-sectional view of an oral insert in accordance with some embodiments.
Figure 12B:
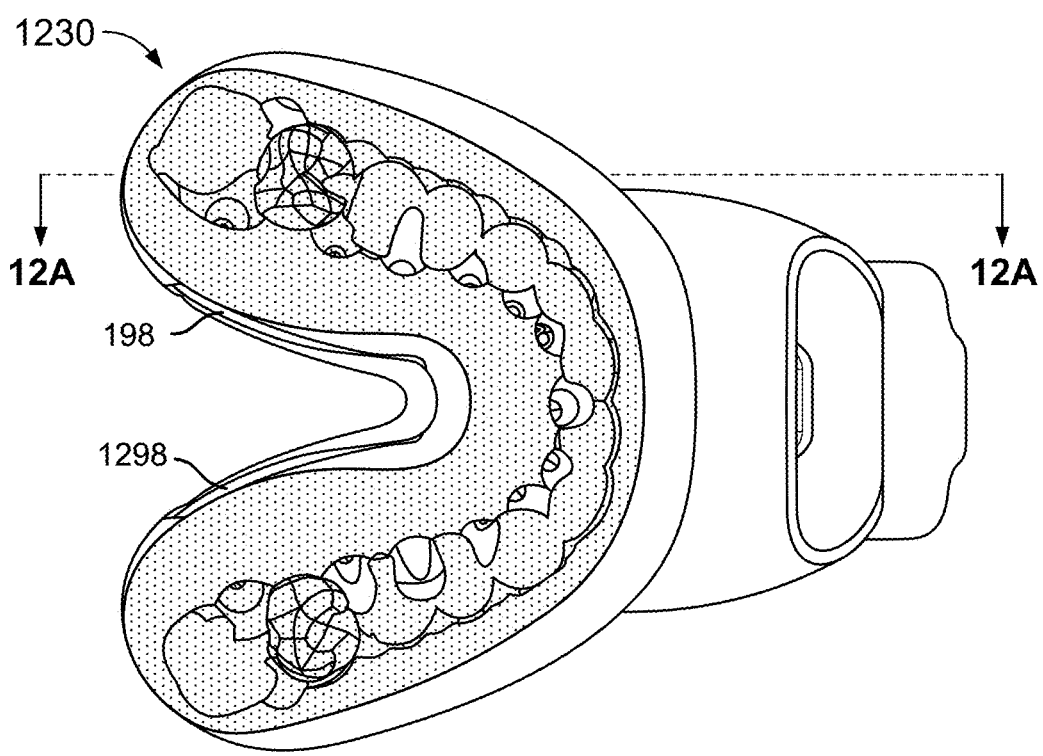
FIG. 12B depicts a top view of an oral insert in accordance with some embodiments.
Figure 12C:
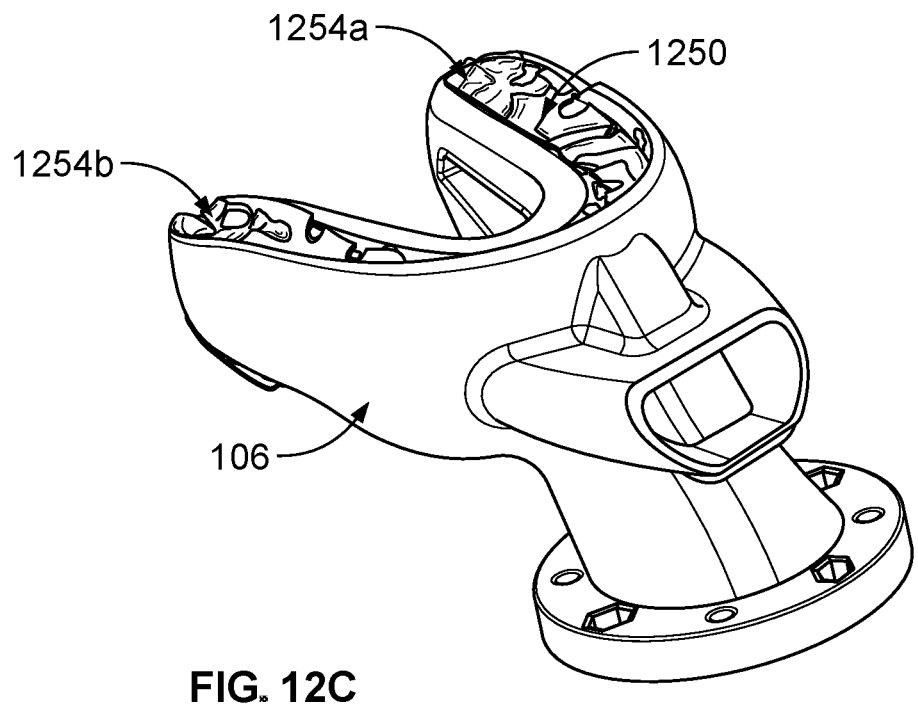
FIG. 12C depicts a perspective view of an oral insert with an elastomeric substrate in accordance with some embodiments.

FIGS. 12A and 12B are cross-sectional and top views, respectively, of an elastomeric substrate (1230) comprising a stand-off structure (1232) that spans between the upper trough/surface (1234) and the lower trough/surface (1236) of the elastomeric substrate elastomeric substrate. A second stand-off structure is located on the other side of the elastomeric substrate (not depicted), in a symmetric (or substantially symmetric) position with respect to a central axis of the oral insert. In some variations where the elastomeric substrate is configured to vibrate, the stand-off structures act as a compliant suspension system to help isolate the motion of the elastomeric substrate from the jaw structure. A stand-off structure may comprise a keying structure (1231) that is configured to couple the contours of the trough (which may correspond with the contours of a user's teeth) to the stand-off structure. For example, the portion of the upper trough (1234) that interfaces with the stand-off structure may comprise a groove or indentation having a shape that corresponds with a protrusion or raised region of the keying structure (1231). A stand-off structure may optionally comprise a chamber or cavity (1233) along its outer perimeter that may be configured to provide space or clearance to allow the oral insert to move independently of the stand-off structure. In some variations, the elastomeric substrate may have a posterior wall portion (1238) that wraps around the posterior teeth (e.g., the molars) so that the posterior portion of the rigid substrate does not directly contact the lingual structures of the oral cavity, which may promote a more comfortable and ergonomic fit. While the variation depicted in FIGS. 12A and 12B depicts two stand-off structures (one on the left and other on the right), it should be understood that in other variations, there could be a single stand-off structure, or more than two stand-off structures, e.g., 3, 4, 5, 6, 7, 8, 9, 10 more stand-off structures. In some variations, the elastomeric substrate may be over-molded or otherwise permanently affixed onto the rigid substrate such that it is not removable from the rigid substrate (without damaging or tearing it), while in other variations, the elastomeric substrate may be releasable attached to the rigid substrate. A releasable elastomeric substrate may be replaced when it wears out from contacting and/or vibrating against a user's teeth, and may help reduce the wear on the rigid substrate by acting as a buffer between the rigid substrate and the teeth. An elastomeric substrate may comprise an attachment mechanism that may comprise one or more of adhesives, magnetic components, interlocking features, fasteners, and the like. For example, the elastomeric substrate may be attached to the rigid substrate by one or more of the following mechanisms: bonding with adhesives, magnetic attachment, press-fit, snap-fit, any interlocking features (e.g., corresponding protrusions and grooves, hook-and-loop engagement), etc. The elastomeric substrate may alternatively or additionally be attached to the rigid substrate using pins, bolts, screws, and/or snaps. The oral insert includes a first posterior opening 198 and a second posterior opening 1298.

In some variations, an oral care system may comprise a vibration damper in the handle as well as an optional vibration damper that may be engaged with an oral insert (e.g., an elastomeric substrate as depicted in FIGS. 12C-12F and described below). Some oral care systems may only have a vibration damper in the handle and no vibration damper in the oral insert, while other oral care systems may only have a damper in the oral insert but none in the handle.

Figure 12D:
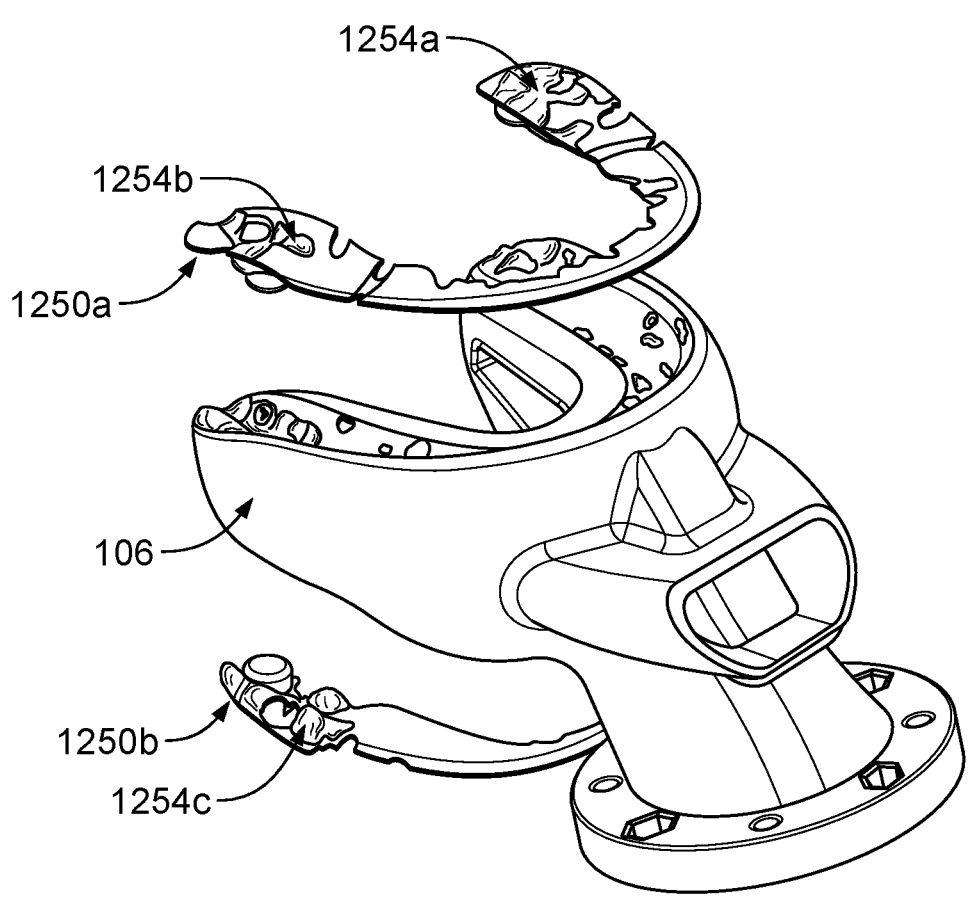
FIG. 12D depicts an exploded view of an oral insert with an elastomeric substrate in accordance with some embodiments.
Figure 12E:
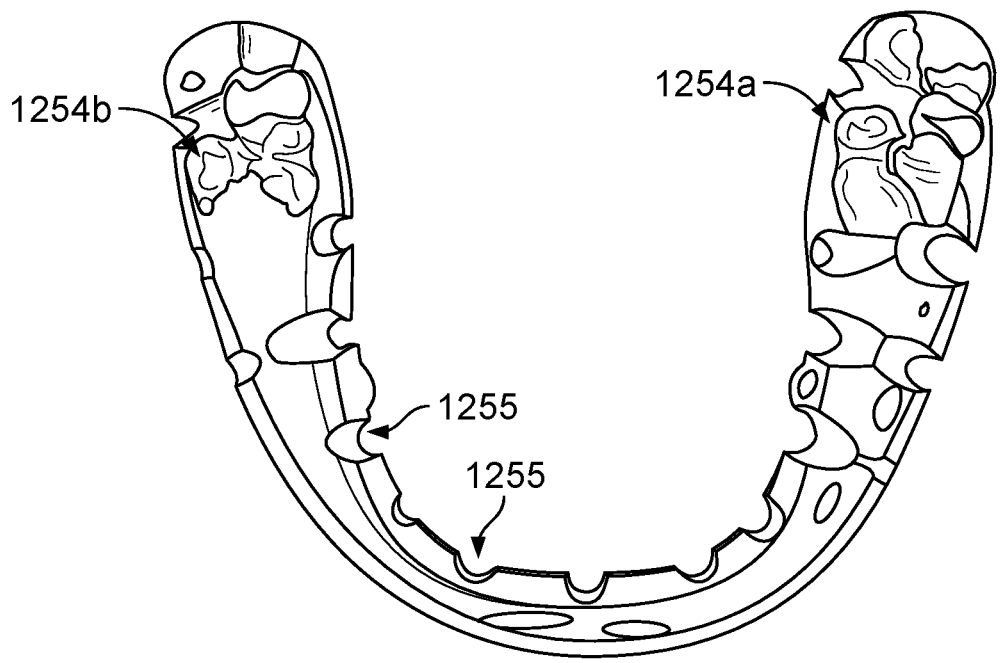
FIGS. 12E-12F depict variations of an elastomeric substrate that may be used
Figure 12F:
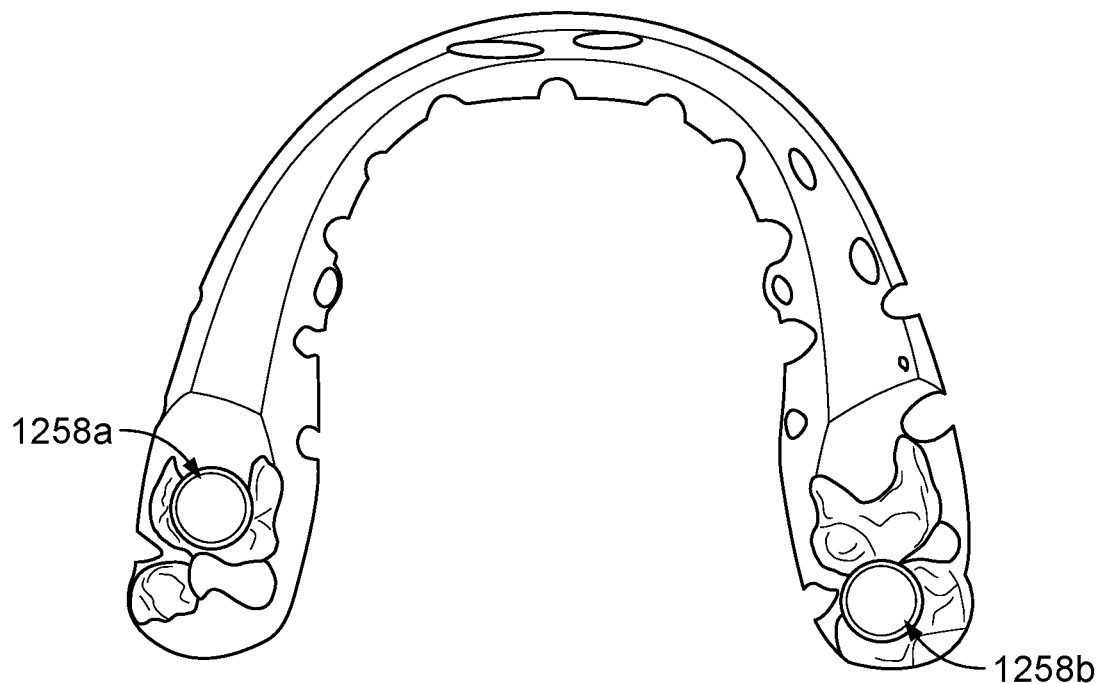

Turning to FIGS. 12C-12F, some variations of elastomeric substrates (1250) may comprise one or more keying features (1254a, 1254b, 1254c) that may include a plurality of protrusions and indentations that may correspond with the surface geometry of the surface of the user's teeth (e.g., contours of the occlusal surface of the back molars). The keying features (1254a, 1254b, 1254c) may help seat the elastomeric substrate within the teeth-retaining portions of the oral insert (106). The elastomeric substrate may comprise a pattern of apertures (1255) to correspond with the nozzle openings of the oral insert. In some variations, as depicted in FIG. 12D, the elastomeric substrate (1250) may comprise an upper substrate (1250a) and a lower substrate (1250b), for the upper and lower portions of the oral insert, respectively. Optionally, as depicted in FIG. 12F, the elastomeric substrate (1250) may comprise one or more interlocking features (1258a, 1258b) located on its underside (i.e., the side of the elastomeric substrate that contacts the oral insert) that may be configured to engage with a corresponding lock feature on the oral insert (not shown). In some variations, the interlocking feature (1258a, 1258b) may comprise a protrusion that is sized and shaped to mate with a corresponding recess in the oral insert. The thickness of the elastomeric substrate may be selected to provide tactile feedback as to how much biting force should be exerted onto the oral insert and/or to help the user correctly seat the oral insert in their mouth.

The location of the one or more keying features may be determined based on a software model that determines an intersection plane associated with a user's teeth. For the set of teeth associated with the maxilla or upper jaw, the portion of the user's teeth that is above the intersection plane corresponds to an undercut region. The one or more keying features for an oral insert corresponding to a user's upper jaw is based on a portion of the determined undercut region. For the set of teeth associated with the mandible or lower jaw, the portion of the user's teeth that is below the intersection plane corresponds to an undercut region. The one or more keying features for an oral insert corresponding to a user's lower jaw is based on a portion of the determined undercut region. The one or more alignment features correspond to some, but not all of the teeth associated with a user. When a user has inserted the oral insert into their mouth, some of their teeth (e.g., molars, premolars, canines, incisors) are in contact with the oral insert. Unlike a sports mouthguard where substantially all of the exterior and bottom surface of a user's teeth are in contact with the mouthguard, having some of the bottom surface area of the user's teeth in contact with the oral insert provides an opening for fluid within the oral insert to flow from a fluid nozzle to the effluence port. In some embodiments, the surface area of a bottom portion of a user's top teeth that contacts the oral insert is less than a particular percentage (e.g., less than 50%) or a particular amount. In some embodiments, the surface area of a top portion of a user's bottom teeth that contacts the oral insert is less than a particular percentage (e.g., less than 50%) or a particular amount.

Figure 13:
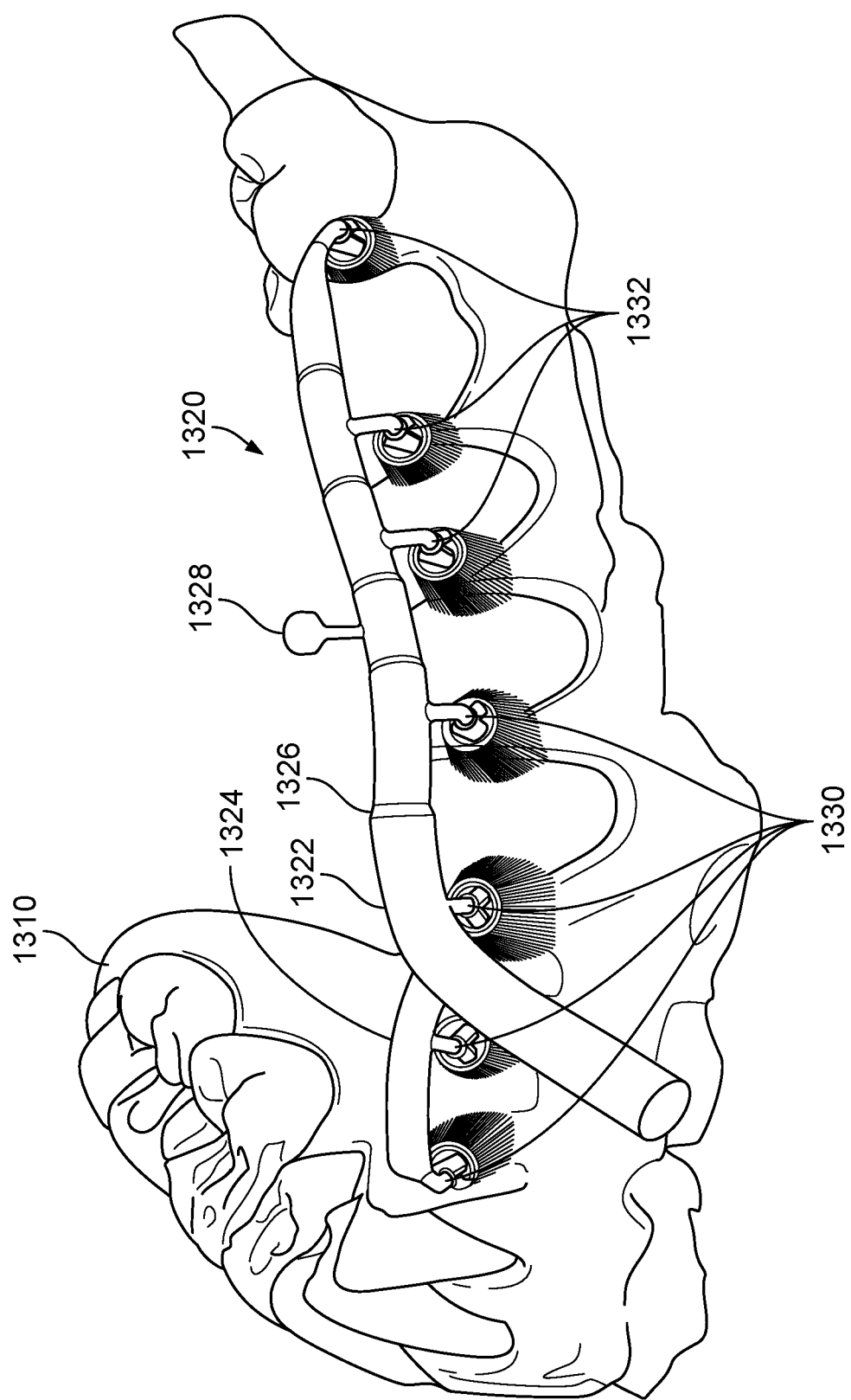
FIG. 13 depicts a schematic perspective view of a manifold relative to oral anatomy in accordance with some embodiments.

FIG. 13 depicts a schematic perspective view of a manifold relative to oral anatomy (1310). The manifold (1320) may be coupled to a set of fluid nozzles (1330) comprising a set of fluid clearance geometries (1332). The manifold (1320) may comprise one or more of a trunk (1322), branch (1324), step region (1326), and pressure port (1328). The trunk (1322) may be a primary fluid conduit coupled between a fluid inlet port (not shown) and each of a branch (1324), pressure port (1328), and fluid nozzle (1330). The trunk (1322) may comprise a larger diameter than any of the branch (1324), pressure port (1328), and fluid nozzles (1330). The branch (1324) may extend from the trunk (1322) and comprise a diameter smaller than the trunk (1322). The branch (1324) may serve as a secondary fluid conduit extending from a trunk (1322) for fluid nozzles (1330) not otherwise coupled to the trunk (1322). For example, a branch (1324) may extend from the trunk (1322) in FIG. 13 for fluid nozzles (1330) corresponding to a set of anterior teeth of a patient. Branches may be useful to reduce tortuosity (e.g., prevent kinks) in the manifold (1320) and improve hydraulic performance of the oral insert. In some variations, one or more pressure ports (1328) (e.g., pressure balancing port) may extend from one or more of trunks (1322) and branches (1324). A pressure port (1328) may be configured to release pressure as fluid flows through the manifold (1320). Without pressure ports (1328), the manifold (1320) and fluid nozzles (1330) may generate unbalanced pressure drops and uneven fluid flow from the fluid nozzles (1330). In some variations, a pressure port (1328) may be useful when a number of nozzles on all manifolds is not equal in order to maintain a predetermined range of hydraulic pressures. For example, a first manifold may include eight fluid nozzles and a second manifold may include seven fluid nozzles and one pressure port (e.g., flow balancing port). The location and size of the pressure port may be designed such that a flow rate of fluid exiting the eight fluid nozzles associated with the first manifold is the same flow rate of fluid exiting the seven fluid nozzles associated with the second manifold.

In some variations, a diameter of the manifold (1320) may decrease along a length of the manifold (1320) due to pressure relieved by a pressure port (1328) on the manifold (1320). In some embodiments, the diameter of the manifold (1320) decreases in a continuous manner. The diameter of the manifold (1320) may decrease at a particular angle. In some embodiments, the diameter of the manifold (1320) decreases in a stepped manner. For example, the diameter of the manifold (1320) may have a first diameter between a first fluid nozzle and a second nozzle and a second diameter between the second nozzle and a third nozzle. In some variations, the number, shape, size, and location of the pressure port (1328) may be configured to promote a predetermined range of pressures through at least a portion of the manifold (1320). For example, one or more pressure ports (1328) may be configured such that a fluid pressure within the manifold (1320) may be within a predetermined range (e.g., relatively constant) throughout a length of the manifold (1320). In some variations, a pressure port (1328) may be located downstream of a step region (1326) of the manifold (1320). In some embodiments, the length of at least one manifold is different than the other manifolds. However, the flow rate of fluid exiting a fluid nozzle on each of the plurality of manifolds should be the same within a predetermined threshold tolerance. One or more pressure ports may be added to a manifold to increase a flow rate associated with the fluid nozzles associated with the manifold to match the flow rate of the fluid nozzles associated with the other manifold(s).

Figure 14:
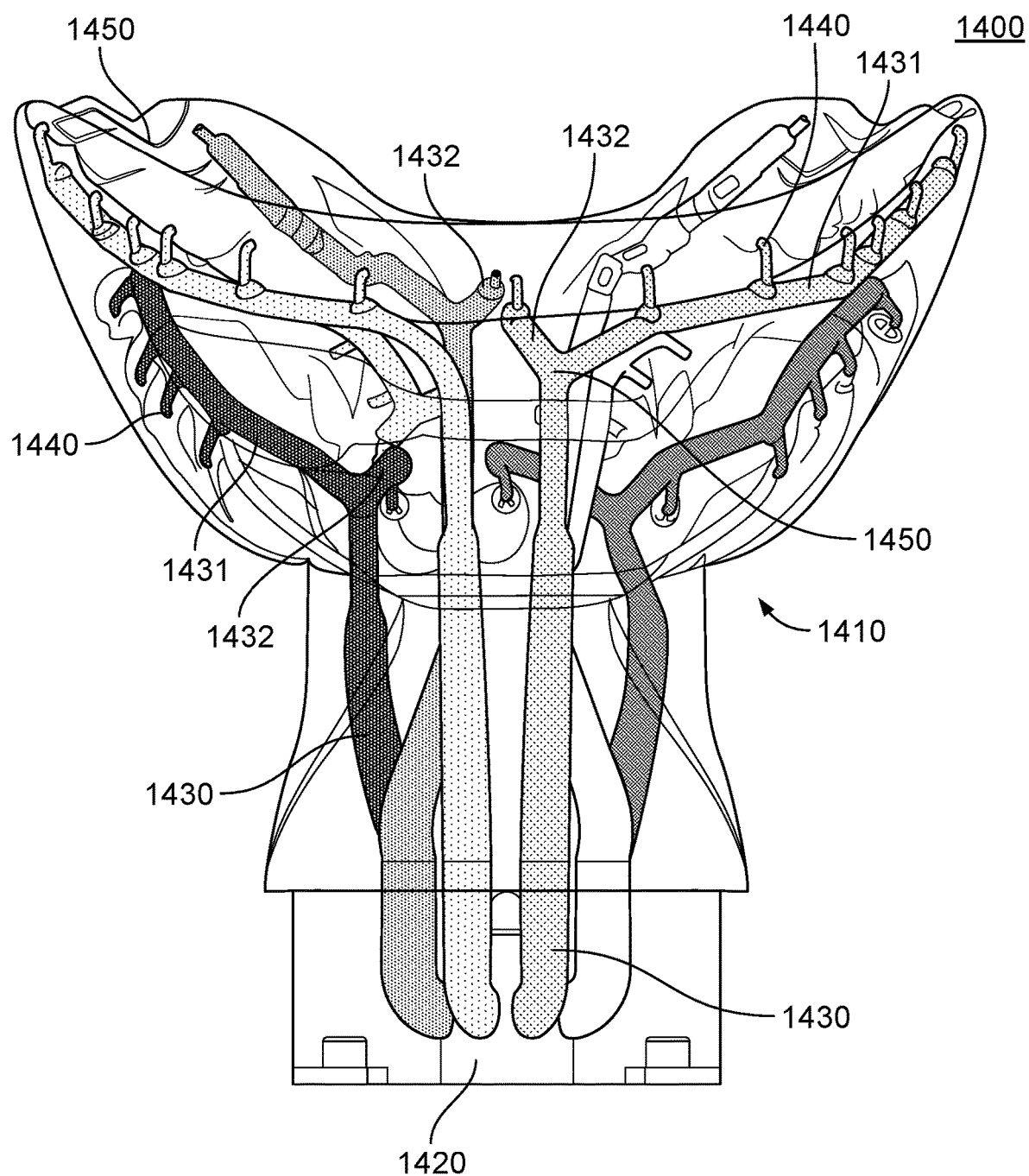
FIG. 14 depicts a schematic perspective view of a set of manifolds of an oral insert in accordance with some embodiments.

FIG. 14 depicts a schematic perspective view of a set of manifolds (1430) of an oral insert (1410). The oral insert (1400) may comprise a fluid inlet port (1420) configured to receive fluid and a tray surface (1450) configured to retain teeth (not shown). The set of manifolds (1430) may be configured to receive fluid from the fluid inlet port (1420). Each manifold (1430) may comprise one or more trunks (1431) and branches (1432) extending from a trunk (1431). Fluid nozzles (1440) may be coupled to respective trunks (1431) and branches (1432). In some variations, the set of manifolds (1430) may extend from the fluid inlet port (1420)

on either side of a lateral plane bisecting the central incisors (not shown). Directly connecting the trunk (1431) to the fluid nozzles (1440) corresponding to the central incisors may generate a hydraulically inefficient tortuous path for the trunk (1431). Therefore, in some variations, a branch (1432) may be used to couple one or more of the anterior fluid nozzles (1440) to the trunk (1431). In FIG. 14, branches (1432) extend toward fluid nozzles (1440) corresponding to the anterior teeth (e.g., central incisors).

Although the foregoing embodiments have been described in some detail for purposes of clarity of understanding, the invention is not limited to the details provided. There are many alternative ways of implementing the invention. The disclosed embodiments are illustrative and not restrictive.

What is claimed is:

1. A system, comprising:
an oral insert that includes a plurality of manifolds and a plurality of fluid nozzles, wherein the oral insert includes a fluid inlet port configured to receive fluid from a fluid source and an effluence conduit configured to enable the fluid to exit the oral insert, wherein the effluence conduit includes a central port configured to drain the fluid from a mouth of a user, a first posterior opening located on a first lingual surface of the oral insert and a second posterior opening located on a second lingual surface of the oral insert, wherein the first posterior opening is coupled to a first lateral channel and the second posterior opening is coupled to a second lateral channel, wherein the first lateral channel and the second lateral channel are coupled to the central port, wherein the first posterior opening and the second posterior opening are configured to receive the fluid from a posterior oral cavity region of the user, wherein the central port terminates at a single anterior opening located at a front portion of the oral insert, wherein the oral insert is customized to a user and includes a trough having one or more alignment features located within the trough to help seat some teeth of the user within the trough; and
a manifold switch coupled to the plurality of manifolds, wherein the manifold switch is configured to select which of the plurality of manifolds is to receive the fluid from the fluid source via a manifold connector located at a bottom portion of the oral insert.

2. The system of claim 1, wherein a first manifold of the plurality of manifolds includes one or more pressure ports.

3. The system of claim 2, wherein the first manifold includes a first number of fluid nozzles and a second manifold of the plurality of manifolds includes a second number of fluid nozzles, wherein the first number and the second number are different.

4. The system of claim 3, wherein a first flow rate of the fluid exiting from the fluid nozzles of the first manifold is within a predetermined tolerance of a second flow rate of the fluid exiting from the fluid nozzles of the second manifold.

5. The system of claim 4, wherein the first flow rate of the fluid exiting from the fluid nozzles of the first manifold is based on a location and size of the one or more pressure ports.

6. The system of claim 1, wherein the manifold switch is configured to sequentially output the fluid to the plurality of manifolds.

7. The system of claim 6, wherein the fluid is sequentially outputted to the plurality of manifolds in an overlapping manner.

8. The system of claim 1, wherein the manifold switch is configured to switch between the plurality of manifolds at a rate of 8 Hz to 30 Hz.

9. The system of claim 1, wherein the manifold switch is configured to provide a pulsatile flow of the fluid.

10. The system of claim 1, wherein a location of the one or more alignment features is based on an undercut region adapted to be associated with an oral anatomy of the user.

11. The system of claim 1, wherein the plurality of manifolds have a continuous taper.

12. The system of claim 1, wherein the central port is configured to have a cross-section area that causes the fluid exiting the oral insert to have a particular pressure.

13. The system of claim 12, wherein the particular pressure is 0.05 psi within a threshold amount.

14. The system of claim 1, wherein the plurality of fluid nozzles are V-shaped.

15. The system of claim 14, wherein a corresponding angle associated with each of the plurality of fluid nozzles is specific to the user.

16. The system of claim 1, further comprising a handle that includes the manifold switch.

17. The system of claim 16, wherein the handle further includes a pump that is configured to provide a particular flow rate of fluid having a particular amount of pressure.

* * * * *